United States Patent
Hiblot et al.

(10) Patent No.: US 12,371,676 B2
(45) Date of Patent: Jul. 29, 2025

(54) CIRCULARLY PERMUTATED HALOALKANE TRANSFERASE FUSION MOLECULES

(71) Applicant: MAX-PLANCK-GESELLSCHAFT ZUR FÖRDERUNG DER WISSENSCHAFTEN E. V., Munich (DE)

(72) Inventors: Julien Hiblot, Heidelberg (DE); Magnus Huppertz, Oldenburg (DE); Kai Johnsson, Heidelberg (DE); Wilhelm Jonas, Heidelberg (DE)

(73) Assignee: MAX-PLANCK-GESELLSCHAFT ZUR FÖRDERUNG DER WISSENSCHAFTEN E.V., Munich (DE)

( * ) Notice: Subject to any disclaimer, the term of this patent is extended or adjusted under 35 U.S.C. 154(b) by 774 days.

(21) Appl. No.: 17/604,417

(22) PCT Filed: Apr. 16, 2020

(86) PCT No.: PCT/EP2020/060785
§ 371 (c)(1),
(2) Date: Oct. 17, 2021

(87) PCT Pub. No.: WO2020/212537
PCT Pub. Date: Oct. 22, 2020

(65) Prior Publication Data
US 2022/0275350 A1    Sep. 1, 2022

(30) Foreign Application Priority Data

Apr. 16, 2019 (EP) .................................... 19169689
Oct. 31, 2019 (EP) .................................... 19206641

(51) Int. Cl.
*C12N 9/10* (2006.01)
*C07K 14/47* (2006.01)

(52) U.S. Cl.
CPC ............... *C12N 9/10* (2013.01); *C07K 14/47* (2013.01); *C12Y 308/01005* (2013.01); C07K 2319/70 (2013.01); C12N 2310/17 (2013.01); C12N 2320/50 (2013.01)

(58) Field of Classification Search
CPC .. C12N 9/10; C12N 2310/17; C12N 2320/50; C07K 14/47; C07K 2319/70; C12Y 308/01005
See application file for complete search history.

(56) References Cited

FOREIGN PATENT DOCUMENTS

| WO | 2008086035 | 7/2008 |
|----|------------|--------|
| WO | 2018219953 | 12/2018 |

*Primary Examiner* — Suzanne M Noakes
*Assistant Examiner* — Ciara A McKnight
(74) *Attorney, Agent, or Firm* — JMB Davis Ben-David

(57) ABSTRACT

The invention relates to a modular polypeptide comprising a first partial effector sequence comprising a first part of a circular permutated halotag protein connected to a sensor module sequence, which is connected to a second part of a circular permutated halotag protein. The sensor module is a single polypeptide or a polypeptide pair capable of undergoing conformational change from a first confirmation to a second confirmation depending on the presence or concentration of an analyte compound. The modular peptide is catalytically active in response to an environmental stimulus or in response to the sensor pair interacting.

The invention further relates to nucleic acid sequences encoding the modular polypeptide, and to kits comprising same.

23 Claims, 17 Drawing Sheets

Specification includes a Sequence Listing.

HaloTag™ 7 dead mutant [nM]

| Substrate | $K_d$ [μM] |
|---|---|
| CPY | 0.622 ± 0.0037 |
| TMR | 6.68 ± 0.16 |
| TMR-az | 4.40 ± 0.022 |
| OG | 39.6 ± 2.15 |
| Alexa 488 | 94.0 ± 2.01 |

HaloTag™ 7 dead mutant [nM]

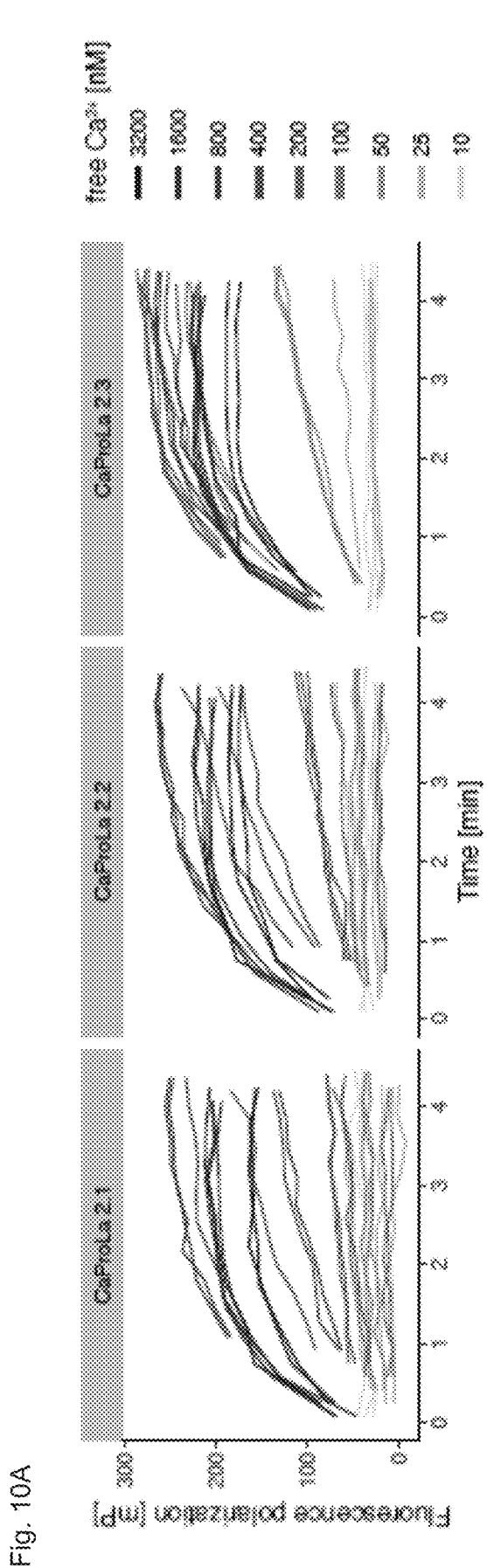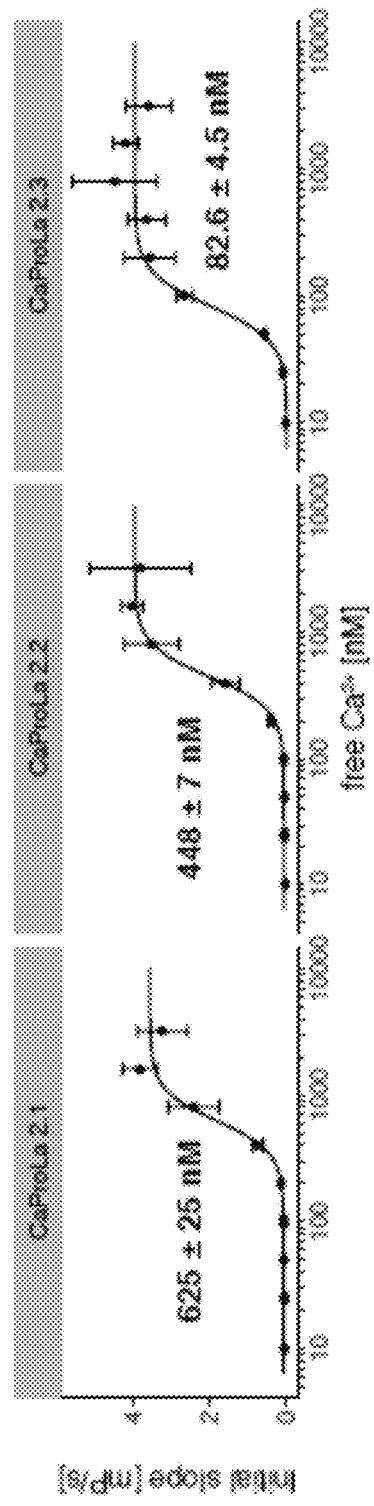
Fig. 10A
Fig. 10B

A

B

SEQUENCE LISTING

<160> NUMBER OF SEQ ID NOS: 29

<210> SEQ ID NO 1
<211> LENGTH: 305
<212> TYPE: PRT
<213> ORGANISM: Artificial Sequence
<220> FEATURE:
<223> OTHER INFORMATION: full sensor sequence

<400> SEQUENCE: 1

Phe Ala Arg Glu Thr Phe Gln Ala Phe Arg Thr Thr Asp Val Gly Arg
1               5                   10                  15

Lys Leu Ile Ile Asp Gln Asn Val Phe Ile Glu Gly Thr Leu Pro Met
            20                  25                  30

Gly Val Val Arg Pro Leu Thr Glu Val Glu Met Asp His Tyr Arg Glu
        35                  40                  45

Pro Phe Leu Asn Pro Val Asp Arg Glu Pro Leu Trp Arg Phe Pro Asn
    50                  55                  60

Glu Leu Pro Ile Ala Gly Glu Pro Ala Asn Ile Val Ala Leu Val Glu
65                  70                  75                  80

Glu Tyr Met Asp Trp Leu His Gln Ser Pro Val Pro Lys Leu Leu Phe
                85                  90                  95

Trp Gly Thr Pro Gly Val Leu Ile Pro Pro Ala Glu Ala Ala Arg Leu
            100                 105                 110

Ala Lys Ser Leu Pro Asn Cys Lys Ala Val Asp Ile Gly Pro Gly Leu
        115                 120                 125

Asn Leu Leu Gln Glu Asp Asn Pro Asp Leu Ile Gly Ser Glu Ile Ala
    130                 135                 140

Arg Trp Leu Ser Thr Leu Glu Ile Gly Gly Thr Gly Gly Ser Gly Gly
145                 150                 155                 160

Thr Gly Gly Ser Gly Gly Ser Ile Gly Thr Gly Phe Pro Phe Asp Pro
                165                 170                 175

His Tyr Val Glu Val Leu Gly Glu Arg Met His Tyr Val Asp Val Gly
            180                 185                 190

Pro Arg Asp Gly Thr Pro Val Leu Phe Leu His Gly Asn Pro Thr Ser
        195                 200                 205

Ser Tyr Val Trp Arg Asn Ile Ile Pro His Val Ala Pro Thr His Arg
    210                 215                 220

Cys Ile Ala Pro Asp Leu Ile Gly Met Gly Lys Ser Asp Lys Pro Asp
225                 230                 235                 240

```
Leu Gly Tyr Phe Phe Asp Asp His Val Arg Phe Met Asp Ala Phe Ile
            245                 250                 255

Glu Ala Leu Gly Leu Glu Glu Val Val Leu Val Ile His Asp Trp Gly
            260                 265                 270

Ser Ala Leu Gly Phe His Trp Ala Lys Arg Asn Pro Glu Arg Val Lys
            275                 280                 285

Gly Ile Ala Phe Met Glu Phe Ile Arg Pro Ile Pro Thr Trp Asp Glu
            290                 295                 300

Trp
305

<210> SEQ ID NO 2
<211> LENGTH: 140
<212> TYPE: PRT
<213> ORGANISM: Artificial Sequence
<220> FEATURE:
<223> OTHER INFORMATION: partial sensor sequence

<400> SEQUENCE: 2

Asp Val Gly Arg Lys Leu Ile Ile Asp Gln Asn Val Phe Ile Glu Gly
1               5                   10                  15

Thr Leu Pro Met Gly Val Val Arg Pro Leu Thr Glu Val Glu Met Asp
            20                  25                  30

His Tyr Arg Glu Pro Phe Leu Asn Pro Val Asp Arg Glu Pro Leu Trp
        35                  40                  45

Arg Phe Pro Asn Glu Leu Pro Ile Ala Gly Glu Pro Ala Asn Ile Val
    50                  55                  60

Ala Leu Val Glu Glu Tyr Met Asp Trp Leu His Gln Ser Pro Val Pro
65                  70                  75                  80

Lys Leu Leu Phe Trp Gly Thr Pro Gly Val Leu Ile Pro Pro Ala Glu
                85                  90                  95

Ala Ala Arg Leu Ala Lys Ser Leu Pro Asn Cys Lys Ala Val Asp Ile
            100                 105                 110

Gly Pro Gly Leu Asn Leu Leu Gln Glu Asp Asn Pro Asp Leu Ile Gly
        115                 120                 125

Ser Glu Ile Ala Arg Trp Leu Ser Thr Leu Glu Ile
    130                 135                 140

<210> SEQ ID NO 3
<211> LENGTH: 138
<212> TYPE: PRT
<213> ORGANISM: Artificial Sequence
<220> FEATURE:
<223> OTHER INFORMATION: partial sensor sequence

<400> SEQUENCE: 3

Ile Gly Thr Gly Phe Pro Phe Asp Pro His Tyr Val Glu Val Leu Gly
1               5                   10                  15

Glu Arg Met His Tyr Val Asp Val Gly Pro Arg Asp Gly Thr Pro Val
            20                  25                  30

Leu Phe Leu His Gly Asn Pro Thr Ser Ser Tyr Val Trp Arg Asn Ile
        35                  40                  45

Ile Pro His Val Ala Pro Thr His Arg Cys Ile Ala Pro Asp Leu Ile
    50                  55                  60

Gly Met Gly Lys Ser Asp Lys Pro Asp Leu Gly Tyr Phe Phe Asp Asp
65                  70                  75                  80

His Val Arg Phe Met Asp Ala Phe Ile Glu Ala Leu Gly Leu Glu Glu
                85                  90                  95
```

```
Val Val Leu Val Ile His Asp Trp Gly Ser Ala Leu Gly Phe His Trp
            100                 105                 110

Ala Lys Arg Asn Pro Glu Arg Val Lys Gly Ile Ala Phe Met Glu Phe
            115                 120                 125

Ile Arg Pro Ile Pro Thr Trp Asp Glu Trp
130                 135

<210> SEQ ID NO 4
<211> LENGTH: 293
<212> TYPE: PRT
<213> ORGANISM: Artificial Sequence
<220> FEATURE:
<223> OTHER INFORMATION: full sensor sequence

<400> SEQUENCE: 4

Asp Val Gly Arg Lys Leu Ile Ile Asp Gln Asn Val Phe Ile Glu Gly
1               5                   10                  15

Thr Leu Pro Met Gly Val Val Arg Pro Leu Thr Glu Val Glu Met Asp
            20                  25                  30

His Tyr Arg Glu Pro Phe Leu Asn Pro Val Asp Arg Glu Pro Leu Trp
        35                  40                  45

Arg Phe Pro Asn Glu Leu Pro Ile Ala Gly Glu Pro Ala Asn Ile Val
50                  55                  60

Ala Leu Val Glu Glu Tyr Met Asp Trp Leu His Gln Ser Pro Val Pro
65                  70                  75                  80

Lys Leu Leu Phe Trp Gly Thr Pro Gly Val Leu Ile Pro Pro Ala Glu
                85                  90                  95

Ala Ala Arg Leu Ala Lys Ser Leu Pro Asn Cys Lys Ala Val Asp Ile
            100                 105                 110

Gly Pro Gly Leu Asn Leu Leu Gln Glu Asp Asn Pro Asp Leu Ile Gly
            115                 120                 125

Ser Glu Ile Ala Arg Trp Leu Ser Thr Leu Glu Ile Gly Gly Thr Gly
            130                 135                 140

Gly Ser Gly Gly Thr Gly Gly Ser Gly Gly Ser Ile Gly Thr Gly Phe
145                 150                 155                 160

Pro Phe Asp Pro His Tyr Val Glu Val Leu Gly Glu Arg Met His Tyr
                165                 170                 175

Val Asp Val Gly Pro Arg Asp Gly Thr Pro Val Leu Phe Leu His Gly
            180                 185                 190

Asn Pro Thr Ser Ser Tyr Val Trp Arg Asn Ile Ile Pro His Val Ala
            195                 200                 205

Pro Thr His Arg Cys Ile Ala Pro Asp Leu Ile Gly Met Gly Lys Ser
        210                 215                 220

Asp Lys Pro Asp Leu Gly Tyr Phe Phe Asp Asp His Val Arg Phe Met
225                 230                 235                 240

Asp Ala Phe Ile Glu Ala Leu Gly Leu Glu Glu Val Val Leu Val Ile
                245                 250                 255

His Asp Trp Gly Ser Ala Leu Gly Phe His Trp Ala Lys Arg Asn Pro
            260                 265                 270

Glu Arg Val Lys Gly Ile Ala Phe Met Glu Phe Ile Arg Pro Ile Pro
            275                 280                 285

Thr Trp Asp Glu Trp
    290

<210> SEQ ID NO 5
```

-continued

```
<211> LENGTH: 15
<212> TYPE: PRT
<213> ORGANISM: Artificial Sequence
<220> FEATURE:
<223> OTHER INFORMATION: partial sensor sequence

<400> SEQUENCE: 5

Gly Gly Thr Gly Gly Ser Gly Gly Thr Gly Gly Ser Gly Gly Ser
1               5                   10                  15

<210> SEQ ID NO 6
<211> LENGTH: 9
<212> TYPE: PRT
<213> ORGANISM: Artificial Sequence
<220> FEATURE:
<223> OTHER INFORMATION: partial sensor sequence

<400> SEQUENCE: 6

Ala Arg Glu Thr Phe Gln Ala Phe Arg
1               5

<210> SEQ ID NO 7
<211> LENGTH: 10
<212> TYPE: PRT
<213> ORGANISM: Artificial Sequence
<220> FEATURE:
<223> OTHER INFORMATION: partial sensor sequence

<400> SEQUENCE: 7

Ala Arg Glu Thr Phe Gln Ala Phe Arg Thr
1               5                   10

<210> SEQ ID NO 8
<211> LENGTH: 26
<212> TYPE: PRT
<213> ORGANISM: Artificial Sequence
<220> FEATURE:
<223> OTHER INFORMATION: partial sensor sequence

<400> SEQUENCE: 8

Arg Val Asp Ser Ser Arg Arg Lys Phe Asn Lys Thr Gly Lys Ala Leu
1               5                   10                  15

Arg Ala Ile Gly Arg Leu Ser Ser Leu Glu
            20                  25

<210> SEQ ID NO 9
<211> LENGTH: 147
<212> TYPE: PRT
<213> ORGANISM: Artificial Sequence
<220> FEATURE:
<223> OTHER INFORMATION: full or partial sensor sequence

<400> SEQUENCE: 9

Asp Gln Leu Thr Glu Glu Gln Ile Ala Glu Phe Lys Glu Ala Phe Ser
1               5                   10                  15

Leu Phe Asp Lys Asp Gly Asp Gly Thr Ile Thr Thr Lys Glu Leu Gly
            20                  25                  30

Thr Val Met Arg Ser Leu Gly Gln Asn Pro Thr Glu Ala Glu Leu Gln
        35                  40                  45

Asp Met Ile Asn Glu Val Asp Ala Asp Gly Asp Gly Thr Ile Asp Phe
    50                  55                  60

Pro Glu Phe Leu Thr Met Met Ala Arg Lys Met Lys Asp Thr Asp Ser
65                  70                  75                  80

Glu Glu Glu Ile Arg Glu Ala Phe Arg Val Phe Asp Lys Asp Gly Asn
```

```
                    85                  90                  95
Gly Tyr Ile Ser Ala Ala Glu Leu Arg His Val Met Thr Asn Leu Gly
                100                 105                 110

Glu Lys Leu Thr Asp Glu Val Asp Glu Met Ile Arg Glu Ala Asp
            115                 120                 125

Ile Asp Gly Asp Gly Gln Val Asn Tyr Glu Glu Phe Val Val Met Met
130                 135                 140

Thr Ala Lys
145

<210> SEQ ID NO 10
<211> LENGTH: 322
<212> TYPE: PRT
<213> ORGANISM: Artificial Sequence
<220> FEATURE:
<223> OTHER INFORMATION: full or partial sensor sequence

<400> SEQUENCE: 10

Arg Val Asp Ser Ser Arg Arg Lys Phe Asn Lys Thr Gly Lys Ala Leu
1               5                   10                  15

Arg Ala Ile Gly Arg Leu Ser Ser Leu Glu Gly Gly Ser Asp Val Gly
                20                  25                  30

Arg Lys Leu Ile Ile Asp Gln Asn Val Phe Ile Glu Gly Thr Leu Pro
            35                  40                  45

Met Gly Val Val Arg Pro Leu Thr Glu Val Glu Met Asp His Tyr Arg
50                  55                  60

Glu Pro Phe Leu Asn Pro Val Asp Arg Glu Pro Leu Trp Arg Phe Pro
65                  70                  75                  80

Asn Glu Leu Pro Ile Ala Gly Glu Pro Ala Asn Ile Val Ala Leu Val
                85                  90                  95

Glu Glu Tyr Met Asp Trp Leu His Gln Ser Pro Val Pro Lys Leu Leu
                100                 105                 110

Phe Trp Gly Thr Pro Gly Val Leu Ile Pro Pro Ala Glu Ala Ala Arg
            115                 120                 125

Leu Ala Lys Ser Leu Pro Asn Cys Lys Ala Val Asp Ile Gly Pro Gly
            130                 135                 140

Leu Asn Leu Leu Gln Glu Asp Asn Pro Asp Leu Ile Gly Ser Glu Ile
145                 150                 155                 160

Ala Arg Trp Leu Ser Thr Leu Glu Ile Gly Gly Thr Gly Gly Ser Gly
                165                 170                 175

Gly Thr Gly Gly Ser Gly Gly Ser Ile Gly Thr Gly Phe Pro Phe Asp
            180                 185                 190

Pro His Tyr Val Glu Val Leu Gly Glu Arg Met His Tyr Val Asp Val
            195                 200                 205

Gly Pro Arg Asp Gly Thr Pro Val Leu Phe Leu His Gly Asn Pro Thr
210                 215                 220

Ser Ser Tyr Val Trp Arg Asn Ile Ile Pro His Val Ala Pro Thr His
225                 230                 235                 240

Arg Cys Ile Ala Pro Asp Leu Ile Gly Met Gly Lys Ser Asp Lys Pro
                245                 250                 255

Asp Leu Gly Tyr Phe Phe Asp Asp His Val Arg Phe Met Asp Ala Phe
            260                 265                 270

Ile Glu Ala Leu Gly Leu Glu Glu Val Val Leu Val Ile His Asp Trp
            275                 280                 285

Gly Ser Ala Leu Gly Phe His Trp Ala Lys Arg Asn Pro Glu Arg Val
```

```
              290                 295                 300

Lys Gly Ile Ala Phe Met Glu Phe Ile Arg Pro Ile Pro Thr Trp Asp
305                 310                 315                 320

Glu Trp

<210> SEQ ID NO 11
<211> LENGTH: 159
<212> TYPE: PRT
<213> ORGANISM: Artificial Sequence
<220> FEATURE:
<223> OTHER INFORMATION: full or partial sensor sequence

<400> SEQUENCE: 11

Ala Arg Glu Thr Phe Gln Ala Phe Arg Gly Gly Ser Asp Gln Leu Thr
1               5                   10                  15

Glu Glu Gln Ile Ala Glu Phe Lys Glu Ala Phe Ser Leu Phe Asp Lys
                20                  25                  30

Asp Gly Asp Gly Thr Ile Thr Thr Lys Glu Leu Gly Thr Val Met Arg
            35                  40                  45

Ser Leu Gly Gln Asn Pro Thr Glu Ala Glu Leu Gln Asp Met Ile Asn
        50                  55                  60

Glu Val Asp Ala Asp Gly Asp Gly Thr Ile Asp Phe Pro Glu Phe Leu
65                  70                  75                  80

Thr Met Met Ala Arg Lys Met Lys Asp Thr Asp Ser Glu Glu Glu Ile
                85                  90                  95

Arg Glu Ala Phe Arg Val Phe Asp Lys Asp Gly Asn Gly Tyr Ile Ser
            100                 105                 110

Ala Ala Glu Leu Arg His Val Met Thr Asn Leu Gly Glu Lys Leu Thr
        115                 120                 125

Asp Glu Glu Val Asp Glu Met Ile Arg Glu Ala Asp Ile Asp Gly Asp
    130                 135                 140

Gly Gln Val Asn Tyr Glu Glu Phe Val Val Met Met Thr Ala Lys
145                 150                 155

<210> SEQ ID NO 12
<211> LENGTH: 159
<212> TYPE: PRT
<213> ORGANISM: Artificial Sequence
<220> FEATURE:
<223> OTHER INFORMATION: full or partial sensor sequence

<400> SEQUENCE: 12

Ala Arg Glu Thr Phe Gln Ala Phe Arg Thr Gly Ser Asp Gln Leu Thr
1               5                   10                  15

Glu Glu Gln Ile Ala Glu Phe Lys Glu Ala Phe Ser Leu Phe Asp Lys
                20                  25                  30

Asp Gly Asp Gly Thr Ile Thr Thr Lys Glu Leu Gly Thr Val Met Arg
            35                  40                  45

Ser Leu Gly Gln Asn Pro Thr Glu Ala Glu Leu Gln Asp Met Ile Asn
        50                  55                  60

Glu Val Asp Ala Asp Gly Asp Gly Thr Ile Asp Phe Pro Glu Phe Leu
65                  70                  75                  80

Thr Met Met Ala Arg Lys Met Lys Asp Thr Asp Ser Glu Glu Glu Ile
                85                  90                  95

Arg Glu Ala Phe Arg Val Phe Asp Lys Asp Gly Asn Gly Tyr Ile Ser
            100                 105                 110

Ala Ala Glu Leu Arg His Val Met Thr Asn Leu Gly Glu Lys Leu Thr
```

```
            115                 120                 125

Asp Glu Glu Val Asp Glu Met Ile Arg Glu Ala Asp Ile Asp Gly Asp
    130                 135                 140

Gly Gln Val Asn Tyr Glu Glu Phe Val Val Met Met Thr Ala Lys
145                 150                 155

<210> SEQ ID NO 13
<211> LENGTH: 516
<212> TYPE: PRT
<213> ORGANISM: Artificial Sequence
<220> FEATURE:
<223> OTHER INFORMATION: full or partial sensor sequence

<400> SEQUENCE: 13

Ala Arg Glu Thr Phe Gln Ala Phe Arg Gly Gly Ser Asp Gln Leu Thr
1               5                   10                  15

Glu Glu Gln Ile Ala Glu Phe Lys Glu Ala Phe Ser Leu Phe Asp Lys
                20                  25                  30

Asp Gly Asp Gly Thr Ile Thr Thr Lys Glu Leu Gly Thr Val Met Arg
            35                  40                  45

Ser Leu Gly Gln Asn Pro Thr Glu Ala Glu Leu Gln Asp Met Ile Asn
50                  55                  60

Glu Val Asp Ala Asp Gly Asp Gly Thr Ile Asp Phe Pro Glu Phe Leu
65                  70                  75                  80

Thr Met Met Ala Arg Lys Met Lys Asp Thr Asp Ser Glu Glu Glu Ile
                85                  90                  95

Arg Glu Ala Phe Arg Val Phe Asp Lys Asp Gly Asn Gly Tyr Ile Ser
            100                 105                 110

Ala Ala Glu Leu Arg His Val Met Thr Asn Leu Gly Glu Lys Leu Thr
        115                 120                 125

Asp Glu Glu Val Asp Glu Met Ile Arg Glu Ala Asp Ile Asp Gly Asp
    130                 135                 140

Gly Gln Val Asn Tyr Glu Glu Phe Val Val Met Met Thr Ala Lys Glu
145                 150                 155                 160

Phe Pro Pro Pro Pro Pro Pro Pro Pro Pro Pro Pro Pro Pro Pro Pro
                165                 170                 175

Pro Pro Pro Pro Pro Pro Pro Pro Pro Pro Pro Pro Pro Pro Pro Gly
            180                 185                 190

Gly Ser Arg Val Asp Ser Ser Arg Arg Lys Phe Asn Lys Thr Gly Lys
        195                 200                 205

Ala Leu Arg Ala Ile Gly Arg Leu Ser Ser Leu Glu Gly Gly Ser Asp
    210                 215                 220

Val Gly Arg Lys Leu Ile Ile Asp Gln Asn Val Phe Ile Glu Gly Thr
225                 230                 235                 240

Leu Pro Met Gly Val Val Arg Pro Leu Thr Glu Val Glu Met Asp His
                245                 250                 255

Tyr Arg Glu Pro Phe Leu Asn Pro Val Asp Arg Glu Pro Leu Trp Arg
            260                 265                 270

Phe Pro Asn Glu Leu Pro Ile Ala Gly Glu Pro Ala Asn Ile Val Ala
        275                 280                 285

Leu Val Glu Glu Tyr Met Asp Trp Leu His Gln Ser Pro Val Pro Lys
    290                 295                 300

Leu Leu Phe Trp Gly Thr Pro Gly Val Leu Ile Pro Pro Ala Glu Ala
305                 310                 315                 320

Ala Arg Leu Ala Lys Ser Leu Pro Asn Cys Lys Ala Val Asp Ile Gly
```

```
                    325                 330                 335
Pro Gly Leu Asn Leu Leu Gln Glu Asp Asn Pro Asp Leu Ile Gly Ser
                340                 345                 350
Glu Ile Ala Arg Trp Leu Ser Thr Leu Glu Ile Gly Gly Thr Gly Gly
            355                 360                 365
Ser Gly Gly Thr Gly Gly Ser Gly Gly Ser Ile Gly Thr Gly Phe Pro
        370                 375                 380
Phe Asp Pro His Tyr Val Glu Val Leu Gly Glu Arg Met His Tyr Val
385                 390                 395                 400
Asp Val Gly Pro Arg Asp Gly Thr Pro Val Leu Phe Leu His Gly Asn
                405                 410                 415
Pro Thr Ser Ser Tyr Val Trp Arg Asn Ile Ile Pro His Val Ala Pro
                420                 425                 430
Thr His Arg Cys Ile Ala Pro Asp Leu Ile Gly Met Gly Lys Ser Asp
                435                 440                 445
Lys Pro Asp Leu Gly Tyr Phe Phe Asp Asp His Val Arg Phe Met Asp
            450                 455                 460
Ala Phe Ile Glu Ala Leu Gly Leu Glu Glu Val Val Leu Val Ile His
465                 470                 475                 480
Asp Trp Gly Ser Ala Leu Gly Phe His Trp Ala Lys Arg Asn Pro Glu
                485                 490                 495
Arg Val Lys Gly Ile Ala Phe Met Glu Phe Ile Arg Pro Ile Pro Thr
                500                 505                 510
Trp Asp Glu Trp
        515

<210> SEQ ID NO 14
<211> LENGTH: 516
<212> TYPE: PRT
<213> ORGANISM: Artificial Sequence
<220> FEATURE:
<223> OTHER INFORMATION: full or partial sensor sequence

<400> SEQUENCE: 14

Ala Arg Glu Thr Phe Gln Ala Phe Arg Thr Gly Ser Asp Gln Leu Thr
1               5                  10                  15
Glu Glu Gln Ile Ala Glu Phe Lys Glu Ala Phe Ser Leu Phe Asp Lys
                20                  25                  30
Asp Gly Asp Gly Thr Ile Thr Thr Lys Glu Leu Gly Thr Val Met Arg
            35                  40                  45
Ser Leu Gly Gln Asn Pro Thr Glu Ala Glu Leu Gln Asp Met Ile Asn
        50                  55                  60
Glu Val Asp Ala Asp Gly Asp Gly Thr Ile Asp Phe Pro Glu Phe Leu
65                  70                  75                  80
Thr Met Met Ala Arg Lys Met Lys Asp Thr Asp Ser Glu Glu Glu Ile
                85                  90                  95
Arg Glu Ala Phe Arg Val Phe Asp Lys Asp Gly Asn Gly Tyr Ile Ser
                100                 105                 110
Ala Ala Glu Leu Arg His Val Met Thr Asn Leu Gly Glu Lys Leu Thr
            115                 120                 125
Asp Glu Glu Val Asp Glu Met Ile Arg Glu Ala Asp Ile Asp Gly Asp
        130                 135                 140
Gly Gln Val Asn Tyr Glu Glu Phe Val Val Met Met Thr Ala Lys Glu
145                 150                 155                 160
Phe Pro Pro Pro Pro Pro Pro Pro Pro Pro Pro Pro Pro Pro Pro Pro
```

```
                    165                 170                 175
Pro Pro Pro Pro Pro Pro Pro Pro Pro Pro Pro Pro Pro Pro Gly
            180                 185                 190
Gly Ser Arg Val Asp Ser Ser Arg Arg Lys Phe Asn Lys Thr Gly Lys
        195                 200                 205
Ala Leu Arg Ala Ile Gly Arg Leu Ser Ser Leu Glu Gly Gly Ser Asp
        210                 215                 220
Val Gly Arg Lys Leu Ile Ile Asp Gln Asn Val Phe Ile Glu Gly Thr
225                 230                 235                 240
Leu Pro Met Gly Val Val Arg Pro Leu Thr Glu Val Glu Met Asp His
            245                 250                 255
Tyr Arg Glu Pro Phe Leu Asn Pro Val Asp Arg Glu Pro Leu Trp Arg
            260                 265                 270
Phe Pro Asn Glu Leu Pro Ile Ala Gly Glu Pro Ala Asn Ile Val Ala
            275                 280                 285
Leu Val Glu Glu Tyr Met Asp Trp Leu His Gln Ser Pro Val Pro Lys
        290                 295                 300
Leu Leu Phe Trp Gly Thr Pro Gly Val Leu Ile Pro Pro Ala Glu Ala
305                 310                 315                 320
Ala Arg Leu Ala Lys Ser Leu Pro Asn Cys Lys Ala Val Asp Ile Gly
            325                 330                 335
Pro Gly Leu Asn Leu Leu Gln Glu Asp Asn Pro Asp Leu Ile Gly Ser
        340                 345                 350
Glu Ile Ala Arg Trp Leu Ser Thr Leu Glu Ile Gly Gly Thr Gly Gly
            355                 360                 365
Ser Gly Gly Thr Gly Gly Ser Gly Gly Ser Ile Gly Thr Gly Phe Pro
    370                 375                 380
Phe Asp Pro His Tyr Val Glu Val Leu Gly Glu Arg Met His Tyr Val
385                 390                 395                 400
Asp Val Gly Pro Arg Asp Gly Thr Pro Val Leu Phe Leu His Gly Asn
            405                 410                 415
Pro Thr Ser Ser Tyr Val Trp Arg Asn Ile Ile Pro His Val Ala Pro
            420                 425                 430
Thr His Arg Cys Ile Ala Pro Asp Leu Ile Gly Met Gly Lys Ser Asp
        435                 440                 445
Lys Pro Asp Leu Gly Tyr Phe Phe Asp Asp His Val Arg Phe Met Asp
    450                 455                 460
Ala Phe Ile Glu Ala Leu Gly Leu Glu Val Val Leu Val Ile His
465                 470                 475                 480
Asp Trp Gly Ser Ala Leu Gly Phe His Trp Ala Lys Arg Asn Pro Glu
            485                 490                 495
Arg Val Lys Gly Ile Ala Phe Met Glu Phe Ile Arg Pro Ile Pro Thr
            500                 505                 510
Trp Asp Glu Trp
        515

<210> SEQ ID NO 15
<211> LENGTH: 108
<212> TYPE: PRT
<213> ORGANISM: Artificial Sequence
<220> FEATURE:
<223> OTHER INFORMATION: full or partial sensor sequence

<400> SEQUENCE: 15

Met Gly Val Gln Val Glu Thr Ile Ser Pro Gly Asp Gly Arg Thr Phe
```

```
                1               5                  10                 15
            Pro Lys Arg Gly Gln Thr Cys Val Val His Tyr Thr Gly Met Leu Glu
                           20                  25                 30

Asp Gly Lys Lys Phe Asp Ser Ser Arg Asp Arg Asn Lys Pro Phe Lys
                           35                  40                 45

Phe Met Leu Gly Lys Gln Glu Val Ile Arg Gly Trp Glu Glu Gly Val
                50                  55                 60

Ala Gln Met Ser Val Gly Gln Arg Ala Lys Leu Thr Ile Ser Pro Asp
            65                  70                  75                 80

Tyr Ala Tyr Gly Ala Thr Gly His Pro Gly Ile Ile Pro Pro His Ala
                           85                  90                 95

Thr Leu Val Phe Asp Val Glu Leu Leu Lys Leu Glu
                           100                 105

<210> SEQ ID NO 16
<211> LENGTH: 94
<212> TYPE: PRT
<213> ORGANISM: Artificial Sequence
<220> FEATURE:
<223> OTHER INFORMATION: full or partial sensor sequence

<400> SEQUENCE: 16

Ala Ile Leu Trp His Glu Met Trp His Glu Gly Leu Glu Glu Ala Ser
            1               5                  10                 15

Arg Leu Tyr Phe Gly Glu Arg Asn Val Lys Gly Met Phe Glu Val Leu
                           20                  25                 30

Glu Pro Leu His Ala Met Met Glu Arg Gly Pro Gln Thr Leu Lys Glu
                           35                  40                 45

Thr Ser Phe Asn Gln Ala Tyr Gly Arg Asp Leu Met Glu Ala Gln Glu
                50                  55                 60

Trp Cys Arg Lys Tyr Met Lys Ser Gly Asn Val Lys Asp Leu Leu Gln
            65                  70                  75                 80

Ala Trp Asp Leu Tyr Tyr His Val Phe Arg Arg Ile Ser Lys
                           85                  90

<210> SEQ ID NO 17
<211> LENGTH: 410
<212> TYPE: PRT
<213> ORGANISM: Artificial Sequence
<220> FEATURE:
<223> OTHER INFORMATION: full or partial sensor sequence

<400> SEQUENCE: 17

Met Gly Val Gln Val Glu Thr Ile Ser Pro Gly Asp Gly Arg Thr Phe
            1               5                  10                 15

Pro Lys Arg Gly Gln Thr Cys Val Val His Tyr Thr Gly Met Leu Glu
                           20                  25                 30

Asp Gly Lys Lys Phe Asp Ser Ser Arg Asp Arg Asn Lys Pro Phe Lys
                           35                  40                 45

Phe Met Leu Gly Lys Gln Glu Val Ile Arg Gly Trp Glu Glu Gly Val
                50                  55                 60

Ala Gln Met Ser Val Gly Gln Arg Ala Lys Leu Thr Ile Ser Pro Asp
            65                  70                  75                 80

Tyr Ala Tyr Gly Ala Thr Gly His Pro Gly Ile Ile Pro Pro His Ala
                           85                  90                 95

Thr Leu Val Phe Asp Val Glu Leu Leu Lys Leu Glu Gly Ser Gly Gly
                           100                 105                110
```

```
Thr Gly Gly Ser Gly Asp Val Gly Arg Lys Leu Ile Ile Asp Gln Asn
            115                 120                 125

Val Phe Ile Glu Gly Thr Leu Pro Met Gly Val Val Arg Pro Leu Thr
130                 135                 140

Glu Val Glu Met Asp His Tyr Arg Glu Pro Phe Leu Asn Pro Val Asp
145                 150                 155                 160

Arg Glu Pro Leu Trp Arg Phe Pro Asn Glu Leu Pro Ile Ala Gly Glu
                165                 170                 175

Pro Ala Asn Ile Val Ala Leu Val Glu Glu Tyr Met Asp Trp Leu His
            180                 185                 190

Gln Ser Pro Val Pro Lys Leu Leu Phe Trp Gly Thr Pro Gly Val Leu
            195                 200                 205

Ile Pro Pro Ala Glu Ala Ala Arg Leu Ala Lys Ser Leu Pro Asn Cys
210                 215                 220

Lys Ala Val Asp Ile Gly Pro Gly Leu Asn Leu Leu Gln Glu Asp Asn
225                 230                 235                 240

Pro Asp Leu Ile Gly Ser Glu Ile Ala Arg Trp Leu Ser Thr Leu Glu
                245                 250                 255

Ile Gly Gly Thr Gly Gly Ser Gly Gly Thr Gly Gly Ser Gly Gly Ser
            260                 265                 270

Ile Gly Thr Gly Phe Pro Phe Asp Pro His Tyr Val Glu Val Leu Gly
            275                 280                 285

Glu Arg Met His Tyr Val Asp Val Gly Pro Arg Asp Gly Thr Pro Val
290                 295                 300

Leu Phe Leu His Gly Asn Pro Thr Ser Ser Tyr Val Trp Arg Asn Ile
305                 310                 315                 320

Ile Pro His Val Ala Pro Thr His Arg Cys Ile Ala Pro Asp Leu Ile
                325                 330                 335

Gly Met Gly Lys Ser Asp Lys Pro Asp Leu Gly Tyr Phe Phe Asp Asp
            340                 345                 350

His Val Arg Phe Met Asp Ala Phe Ile Glu Ala Leu Gly Leu Glu Glu
            355                 360                 365

Val Val Leu Val Ile His Asp Trp Gly Ser Ala Leu Gly Phe His Trp
370                 375                 380

Ala Lys Arg Asn Pro Glu Arg Val Lys Gly Ile Ala Phe Met Glu Phe
385                 390                 395                 400

Ile Arg Pro Ile Pro Thr Trp Asp Glu Trp
                405                 410

<210> SEQ ID NO 18
<211> LENGTH: 106
<212> TYPE: PRT
<213> ORGANISM: Artificial Sequence
<220> FEATURE:
<223> OTHER INFORMATION: full or partial sensor sequence

<400> SEQUENCE: 18

Ala Arg Glu Thr Phe Gln Ala Phe Arg Gly Gly Ser Ala Ile Leu Trp
1               5                   10                  15

His Glu Met Trp His Glu Gly Leu Glu Glu Ala Ser Arg Leu Tyr Phe
            20                  25                  30

Gly Glu Arg Asn Val Lys Gly Met Phe Glu Val Leu Glu Pro Leu His
        35                  40                  45

Ala Met Met Glu Arg Gly Pro Gln Thr Leu Lys Glu Thr Ser Phe Asn
50                  55                  60
```

```
Gln Ala Tyr Gly Arg Asp Leu Met Glu Ala Gln Glu Trp Cys Arg Lys
 65                  70                  75                  80

Tyr Met Lys Ser Gly Asn Val Lys Asp Leu Leu Gln Ala Trp Asp Leu
                 85                  90                  95

Tyr Tyr His Val Phe Arg Arg Ile Ser Lys
            100                 105

<210> SEQ ID NO 19
<211> LENGTH: 106
<212> TYPE: PRT
<213> ORGANISM: Artificial Sequence
<220> FEATURE:
<223> OTHER INFORMATION: full or partial sensor sequence

<400> SEQUENCE: 19

Ala Arg Glu Thr Phe Gln Ala Phe Arg Thr Gly Ser Ala Ile Leu Trp
 1               5                  10                  15

His Glu Met Trp His Glu Gly Leu Glu Glu Ala Ser Arg Leu Tyr Phe
                20                  25                  30

Gly Glu Arg Asn Val Lys Gly Met Phe Glu Val Leu Glu Pro Leu His
             35                  40                  45

Ala Met Met Glu Arg Gly Pro Gln Thr Leu Lys Glu Thr Ser Phe Asn
 50                  55                  60

Gln Ala Tyr Gly Arg Asp Leu Met Glu Ala Gln Glu Trp Cys Arg Lys
 65                  70                  75                  80

Tyr Met Lys Ser Gly Asn Val Lys Asp Leu Leu Gln Ala Trp Asp Leu
                 85                  90                  95

Tyr Tyr His Val Phe Arg Arg Ile Ser Lys
            100                 105

<210> SEQ ID NO 20
<211> LENGTH: 249
<212> TYPE: PRT
<213> ORGANISM: Artificial Sequence
<220> FEATURE:
<223> OTHER INFORMATION: full or partial sensor sequence

<400> SEQUENCE: 20

Ala Ala Gly Ser Thr Leu Asp Lys Ile Ala Lys Asn Gly Val Ile Val
 1               5                  10                  15

Val Gly His Arg Glu Ser Ser Val Pro Phe Ser Tyr Tyr Asp Asn Gln
                20                  25                  30

Gln Lys Val Val Gly Tyr Ser Gln Asp Tyr Ser Asn Ala Ile Val Glu
             35                  40                  45

Ala Val Lys Lys Lys Leu Asn Lys Pro Asp Leu Gln Val Lys Leu Ile
 50                  55                  60

Pro Ile Thr Ser Gln Asn Arg Ile Pro Leu Leu Gln Asn Gly Thr Phe
 65                  70                  75                  80

Asp Phe Glu Cys Gly Ser Thr Thr Asn Asn Val Glu Arg Gln Lys Gln
                 85                  90                  95

Ala Ala Phe Ser Asp Thr Ile Phe Val Val Gly Thr Arg Leu Leu Thr
            100                 105                 110

Lys Lys Gly Gly Asp Ile Lys Asp Phe Ala Asn Leu Lys Asp Lys Ala
            115                 120                 125

Val Val Val Thr Ser Gly Thr Thr Ser Glu Val Leu Leu Asn Lys Leu
        130                 135                 140

Asn Glu Glu Gln Lys Met Asn Met Arg Ile Ile Ser Ala Lys Asp His
145                 150                 155                 160
```

```
Gly Asp Ser Phe Arg Thr Leu Glu Ser Gly Arg Ala Val Ala Phe Met
                165                 170                 175

Met Asp Asp Val Leu Leu Ala Gly Glu Arg Ala Lys Ala Lys Lys Pro
            180                 185                 190

Asp Asn Trp Glu Ile Val Gly Lys Pro Gln Ser Gln Glu Ala Tyr Gly
        195                 200                 205

Cys Met Leu Arg Lys Asp Asp Pro Gln Phe Lys Lys Leu Met Asp Asp
    210                 215                 220

Thr Ile Ala Gln Val Gln Thr Ser Gly Glu Ala Glu Lys Trp Phe Asp
225                 230                 235                 240

Lys Trp Phe Lys Asn Pro Ile Leu Val
                245

<210> SEQ ID NO 21
<211> LENGTH: 26
<212> TYPE: PRT
<213> ORGANISM: Artificial Sequence
<220> FEATURE:
<223> OTHER INFORMATION: full or partial sensor sequence

<400> SEQUENCE: 21

Asn Pro Leu Asn Met Asn Phe Glu Leu Ser Asp Glu Met Lys Ala Leu
1               5                   10                  15

Phe Lys Glu Pro Asn Asp Lys Ala Leu Lys
            20                  25

<210> SEQ ID NO 22
<211> LENGTH: 520
<212> TYPE: PRT
<213> ORGANISM: Artificial Sequence
<220> FEATURE:
<223> OTHER INFORMATION: full or partial sensor sequence

<400> SEQUENCE: 22

Ala Ala Gly Ser Thr Leu Asp Lys Ile Ala Lys Asn Gly Val Ile Val
1               5                   10                  15

Val Gly His Arg Glu Ser Ser Val Pro Phe Ser Tyr Tyr Asp Asn Gln
            20                  25                  30

Gln Lys Val Val Gly Tyr Ser Gln Asp Tyr Ser Asn Ala Ile Val Glu
        35                  40                  45

Ala Val Lys Lys Lys Leu Asn Lys Pro Asp Leu Gln Val Lys Leu Ile
    50                  55                  60

Pro Ile Thr Ser Gln Asn Arg Ile Pro Leu Leu Gln Asn Gly Thr Phe
65                  70                  75                  80

Asp Phe Glu Cys Gly Ser Thr Thr Asn Asn Val Glu Arg Gln Lys Gln
                85                  90                  95

Ala Ala Phe Ser Asp Thr Ile Phe Val Val Gly Thr Arg Leu Leu Thr
            100                 105                 110

Lys Lys Gly Gly Asp Ile Lys Asp Phe Ala Asn Leu Lys Asp Lys Ala
        115                 120                 125

Val Val Val Thr Ser Gly Thr Thr Ser Glu Val Leu Leu Asn Lys Leu
    130                 135                 140

Asn Glu Glu Gln Lys Met Asn Met Arg Ile Ile Ser Ala Lys Asp His
145                 150                 155                 160

Gly Asp Ser Phe Arg Thr Leu Glu Ser Gly Arg Ala Val Ala Phe Met
                165                 170                 175

Met Asp Asp Val Leu Leu Ala Gly Glu Arg Ala Lys Ala Lys Lys Pro
            180                 185                 190
```

```
            180                 185                 190
Asp Asn Trp Glu Ile Val Gly Lys Pro Gln Ser Gln Glu Ala Tyr Gly
        195                 200                 205

Cys Met Leu Arg Lys Asp Asp Pro Gln Phe Lys Lys Leu Met Asp Asp
    210                 215                 220

Thr Ile Ala Gln Val Gln Thr Ser Gly Glu Ala Glu Lys Trp Phe Asp
225                 230                 235                 240

Lys Trp Phe Lys Asn Pro Ile Leu Val Ser His Asn Val Tyr Ile Met
                245                 250                 255

Ala Asp Lys Gln Arg Asn Gly Ile Lys Ala Asn Phe Lys Ile Arg His
            260                 265                 270

Asn Ile Glu Asp Gly Gly Val Gln Leu Ala Tyr His Tyr Gln Gln Asn
        275                 280                 285

Thr Pro Ile Gly Asp Gly Pro Val Leu Leu Pro Asp Asn His Tyr Leu
    290                 295                 300

Ser Thr Gln Ser Lys Leu Ser Lys Asp Pro Asn Glu Lys Arg Asp His
305                 310                 315                 320

Met Val Leu Leu Glu Phe Val Thr Ala Ala Gly Ile Thr Leu Gly Met
                325                 330                 335

Asp Glu Leu Tyr Lys Gly Gly Thr Gly Gly Ser Met Val Ser Lys Gly
            340                 345                 350

Glu Glu Leu Phe Thr Gly Val Val Pro Ile Leu Val Glu Leu Asp Gly
        355                 360                 365

Asp Val Asn Gly His Lys Phe Ser Val Ser Gly Glu Gly Glu Gly Asp
    370                 375                 380

Ala Thr Tyr Gly Lys Leu Thr Leu Lys Phe Ile Cys Thr Thr Gly Lys
385                 390                 395                 400

Leu Pro Val Pro Trp Pro Thr Leu Val Thr Thr Leu Thr Tyr Gly Val
                405                 410                 415

Gln Cys Phe Ser Arg Tyr Pro Asp His Met Lys Gln His Asp Phe Phe
            420                 425                 430

Lys Ser Ala Met Pro Glu Gly Tyr Ile Gln Glu Arg Thr Ile Phe Phe
        435                 440                 445

Lys Asp Asp Gly Asn Tyr Lys Thr Arg Ala Glu Val Lys Phe Glu Gly
    450                 455                 460

Asp Thr Leu Val Asn Arg Ile Glu Leu Lys Gly Ile Asp Phe Lys Glu
465                 470                 475                 480

Asp Gly Asn Ile Leu Gly His Lys Leu Glu Tyr Asn Phe Asn Asn Pro
                485                 490                 495

Leu Asn Met Asn Phe Glu Leu Ser Asp Glu Met Lys Ala Leu Phe Lys
            500                 505                 510

Glu Pro Asn Asp Lys Ala Leu Lys
        515                 520

<210> SEQ ID NO 23
<211> LENGTH: 265
<212> TYPE: PRT
<213> ORGANISM: Artificial Sequence
<220> FEATURE:
<223> OTHER INFORMATION: full or partial sensor sequence

<400> SEQUENCE: 23

Ala Arg Glu Thr Phe Gln Ala Phe Arg Thr Gly Gly Thr Gly Gly Ser
1               5                   10                  15

Ala Ala Gly Ser Thr Leu Asp Lys Ile Ala Lys Asn Gly Val Ile Val
```

```
                20                  25                  30
Val Gly His Arg Glu Ser Ser Val Pro Phe Ser Tyr Tyr Asp Asn Gln
            35                  40                  45

Gln Lys Val Val Gly Tyr Ser Gln Asp Tyr Ser Asn Ala Ile Val Glu
    50                  55                  60

Ala Val Lys Lys Lys Leu Asn Lys Pro Asp Leu Gln Val Lys Leu Ile
65                  70                  75                  80

Pro Ile Thr Ser Gln Asn Arg Ile Pro Leu Leu Gln Asn Gly Thr Phe
                85                  90                  95

Asp Phe Glu Cys Gly Ser Thr Thr Asn Asn Val Glu Arg Gln Lys Gln
            100                 105                 110

Ala Ala Phe Ser Asp Thr Ile Phe Val Val Gly Thr Arg Leu Leu Thr
        115                 120                 125

Lys Lys Gly Gly Asp Ile Lys Asp Phe Ala Asn Leu Lys Asp Lys Ala
    130                 135                 140

Val Val Val Thr Ser Gly Thr Thr Ser Glu Val Leu Leu Asn Lys Leu
145                 150                 155                 160

Asn Glu Glu Gln Lys Met Asn Met Arg Ile Ile Ser Ala Lys Asp His
                165                 170                 175

Gly Asp Ser Phe Arg Thr Leu Glu Ser Gly Arg Ala Val Ala Phe Met
            180                 185                 190

Met Asp Asp Val Leu Leu Ala Gly Glu Arg Ala Lys Ala Lys Lys Pro
        195                 200                 205

Asp Asn Trp Glu Ile Val Gly Lys Pro Gln Ser Gln Glu Ala Tyr Gly
    210                 215                 220

Cys Met Leu Arg Lys Asp Pro Gln Phe Lys Lys Leu Met Asp Asp
225                 230                 235                 240

Thr Ile Ala Gln Val Gln Thr Ser Gly Glu Ala Glu Lys Trp Phe Asp
                245                 250                 255

Lys Trp Phe Lys Asn Pro Ile Leu Val
            260                 265

<210> SEQ ID NO 24
<211> LENGTH: 325
<212> TYPE: PRT
<213> ORGANISM: Artificial Sequence
<220> FEATURE:
<223> OTHER INFORMATION: full or partial sonsor sequence

<400> SEQUENCE: 24

Asn Pro Leu Asn Met Asn Phe Glu Leu Ser Asp Glu Met Lys Ala Leu
1               5                   10                  15

Phe Lys Glu Pro Asn Asp Lys Ala Leu Lys Gly Gly Thr Gly Gly Ser
                20                  25                  30

Asp Val Gly Arg Lys Leu Ile Ile Asp Gln Asn Val Phe Ile Glu Gly
            35                  40                  45

Thr Leu Pro Met Gly Val Val Arg Pro Leu Thr Glu Val Glu Met Asp
        50                  55                  60

His Tyr Arg Glu Pro Phe Leu Asn Pro Val Asp Arg Glu Pro Leu Trp
65                  70                  75                  80

Arg Phe Pro Asn Glu Leu Pro Ile Ala Gly Glu Pro Ala Asn Ile Val
                85                  90                  95

Ala Leu Val Glu Glu Tyr Met Asp Trp Leu His Gln Ser Pro Val Pro
            100                 105                 110

Lys Leu Leu Phe Trp Gly Thr Pro Gly Val Leu Ile Pro Pro Ala Glu
```

-continued

```
                115                 120                 125
Ala Ala Arg Leu Ala Lys Ser Leu Pro Asn Cys Lys Ala Val Asp Ile
    130                 135                 140

Gly Pro Gly Leu Asn Leu Leu Gln Glu Asp Asn Pro Asp Leu Ile Gly
145                 150                 155                 160

Ser Glu Ile Ala Arg Trp Leu Ser Thr Leu Ile Gly Gly Thr Gly
                165                 170                 175

Gly Ser Gly Gly Thr Gly Gly Ser Gly Gly Ser Ile Gly Thr Gly Phe
            180                 185                 190

Pro Phe Asp Pro His Tyr Val Glu Val Leu Gly Glu Arg Met His Tyr
                195                 200                 205

Val Asp Val Gly Pro Arg Asp Gly Thr Pro Val Leu Phe Leu His Gly
    210                 215                 220

Asn Pro Thr Ser Ser Tyr Val Trp Arg Asn Ile Ile Pro His Val Ala
225                 230                 235                 240

Pro Thr His Arg Cys Ile Ala Pro Asp Leu Ile Gly Met Gly Lys Ser
                245                 250                 255

Asp Lys Pro Asp Leu Gly Tyr Phe Phe Asp Asp His Val Arg Phe Met
            260                 265                 270

Asp Ala Phe Ile Glu Ala Leu Gly Leu Glu Val Val Leu Val Ile
                275                 280                 285

His Asp Trp Gly Ser Ala Leu Gly Phe His Trp Ala Lys Arg Asn Pro
    290                 295                 300

Glu Arg Val Lys Gly Ile Ala Phe Met Glu Phe Ile Arg Pro Ile Pro
305                 310                 315                 320

Thr Trp Asp Glu Trp
                325

<210> SEQ ID NO 25
<211> LENGTH: 835
<212> TYPE: PRT
<213> ORGANISM: Artificial Sequence
<220> FEATURE:
<223> OTHER INFORMATION: full or partial sensor sequence

<400> SEQUENCE: 25

Ala Arg Glu Thr Phe Gln Ala Phe Arg Thr Gly Gly Thr Gly Gly Ser
1               5                   10                  15

Ala Ala Gly Ser Thr Leu Asp Lys Ile Ala Lys Asn Gly Val Ile Val
                20                  25                  30

Val Gly His Arg Glu Ser Ser Val Pro Phe Ser Tyr Tyr Asp Asn Gln
            35                  40                  45

Gln Lys Val Val Gly Tyr Ser Gln Asp Tyr Ser Asn Ala Ile Val Glu
        50                  55                  60

Ala Val Lys Lys Lys Leu Asn Lys Pro Asp Leu Gln Val Lys Leu Ile
65                  70                  75                  80

Pro Ile Thr Ser Gln Asn Arg Ile Pro Leu Leu Gln Asn Gly Thr Phe
                85                  90                  95

Asp Phe Glu Cys Gly Ser Thr Thr Asn Asn Val Glu Arg Gln Lys Gln
            100                 105                 110

Ala Ala Phe Ser Asp Thr Ile Phe Val Val Gly Thr Arg Leu Leu Thr
        115                 120                 125

Lys Lys Gly Gly Asp Ile Lys Asp Phe Ala Asn Leu Lys Asp Lys Ala
    130                 135                 140

Val Val Val Thr Ser Gly Thr Thr Ser Glu Val Leu Leu Asn Lys Leu
```

```
            145                 150                 155                 160
Asn Glu Glu Gln Lys Met Asn Met Arg Ile Ile Ser Ala Lys Asp His
                165                 170                 175

Gly Asp Ser Phe Arg Thr Leu Glu Ser Gly Arg Ala Val Ala Phe Met
            180                 185                 190

Met Asp Asp Val Leu Leu Ala Gly Glu Arg Ala Lys Ala Lys Lys Pro
            195                 200                 205

Asp Asn Trp Glu Ile Val Gly Lys Pro Gln Ser Gln Glu Ala Tyr Gly
            210                 215                 220

Cys Met Leu Arg Lys Asp Asp Pro Gln Phe Lys Lys Leu Met Asp Asp
225                 230                 235                 240

Thr Ile Ala Gln Val Gln Thr Ser Gly Glu Ala Glu Lys Trp Phe Asp
            245                 250                 255

Lys Trp Phe Lys Asn Pro Ile Leu Val Ser His Asn Val Tyr Ile Met
            260                 265                 270

Ala Asp Lys Gln Arg Asn Gly Ile Lys Ala Asn Phe Lys Ile Arg His
            275                 280                 285

Asn Ile Glu Asp Gly Gly Val Gln Leu Ala Tyr His Tyr Gln Gln Asn
            290                 295                 300

Thr Pro Ile Gly Asp Gly Pro Val Leu Leu Pro Asp Asn His Tyr Leu
305                 310                 315                 320

Ser Thr Gln Ser Lys Leu Ser Lys Asp Pro Asn Glu Lys Arg Asp His
            325                 330                 335

Met Val Leu Leu Glu Phe Val Thr Ala Ala Gly Ile Thr Leu Gly Met
            340                 345                 350

Asp Glu Leu Tyr Lys Gly Gly Thr Gly Gly Ser Met Val Ser Lys Gly
            355                 360                 365

Glu Glu Leu Phe Thr Gly Val Val Pro Ile Leu Val Glu Leu Asp Gly
            370                 375                 380

Asp Val Asn Gly His Lys Phe Ser Val Ser Gly Glu Gly Glu Gly Asp
385                 390                 395                 400

Ala Thr Tyr Gly Lys Leu Thr Leu Lys Phe Ile Cys Thr Thr Gly Lys
            405                 410                 415

Leu Pro Val Pro Trp Pro Thr Leu Val Thr Thr Leu Thr Tyr Gly Val
            420                 425                 430

Gln Cys Phe Ser Arg Tyr Pro Asp His Met Lys Gln His Asp Phe Phe
            435                 440                 445

Lys Ser Ala Met Pro Glu Gly Tyr Ile Gln Glu Arg Thr Ile Phe Phe
            450                 455                 460

Lys Asp Asp Gly Asn Tyr Lys Thr Arg Ala Glu Val Lys Phe Glu Gly
465                 470                 475                 480

Asp Thr Leu Val Asn Arg Ile Glu Leu Lys Gly Ile Asp Phe Lys Glu
            485                 490                 495

Asp Gly Asn Ile Leu Gly His Lys Leu Glu Tyr Asn Phe Asn Asn Pro
            500                 505                 510

Leu Asn Met Asn Phe Glu Leu Ser Asp Glu Met Lys Ala Leu Phe Lys
            515                 520                 525

Glu Pro Asn Asp Lys Ala Leu Lys Gly Gly Thr Gly Gly Ser Asp Val
            530                 535                 540

Gly Arg Lys Leu Ile Ile Asp Gln Asn Val Phe Ile Glu Gly Thr Leu
545                 550                 555                 560

Pro Met Gly Val Val Arg Pro Leu Thr Glu Val Glu Met Asp His Tyr
            565                 570                 575
```

```
Arg Glu Pro Phe Leu Asn Pro Val Asp Arg Glu Pro Leu Trp Arg Phe
                580                 585                 590

Pro Asn Glu Leu Pro Ile Ala Gly Glu Pro Ala Asn Ile Val Ala Leu
            595                 600                 605

Val Glu Glu Tyr Met Asp Trp Leu His Gln Ser Pro Val Pro Lys Leu
        610                 615                 620

Leu Phe Trp Gly Thr Pro Gly Val Leu Ile Pro Pro Ala Glu Ala Ala
625                 630                 635                 640

Arg Leu Ala Lys Ser Leu Pro Asn Cys Lys Ala Val Asp Ile Gly Pro
                645                 650                 655

Gly Leu Asn Leu Leu Gln Glu Asp Asn Pro Asp Leu Ile Gly Ser Glu
            660                 665                 670

Ile Ala Arg Trp Leu Ser Thr Leu Glu Ile Gly Gly Thr Gly Gly Ser
        675                 680                 685

Gly Gly Thr Gly Gly Ser Gly Gly Ser Ile Gly Thr Gly Phe Pro Phe
690                 695                 700

Asp Pro His Tyr Val Glu Val Leu Gly Glu Arg Met His Tyr Val Asp
705                 710                 715                 720

Val Gly Pro Arg Asp Gly Thr Pro Val Leu Phe Leu His Gly Asn Pro
                725                 730                 735

Thr Ser Ser Tyr Val Trp Arg Asn Ile Ile Pro His Val Ala Pro Thr
            740                 745                 750

His Arg Cys Ile Ala Pro Asp Leu Ile Gly Met Gly Lys Ser Asp Lys
        755                 760                 765

Pro Asp Leu Gly Tyr Phe Phe Asp Asp His Val Arg Phe Met Asp Ala
770                 775                 780

Phe Ile Glu Ala Leu Gly Leu Glu Glu Val Val Leu Val Ile His Asp
785                 790                 795                 800

Trp Gly Ser Ala Leu Gly Phe His Trp Ala Lys Arg Asn Pro Glu Arg
                805                 810                 815

Val Lys Gly Ile Ala Phe Met Glu Phe Ile Arg Pro Ile Pro Thr Trp
            820                 825                 830

Asp Glu Trp
        835

<210> SEQ ID NO 26
<211> LENGTH: 6
<212> TYPE: PRT
<213> ORGANISM: Artificial Sequence
<220> FEATURE:
<223> OTHER INFORMATION: partial linker sequence

<400> SEQUENCE: 26

Gly Gly Thr Gly Gly Ser
1               5

<210> SEQ ID NO 27
<211> LENGTH: 6
<212> TYPE: PRT
<213> ORGANISM: Artificial Sequence
<220> FEATURE:
<223> OTHER INFORMATION: linker sequence

<400> SEQUENCE: 27

Gly Gly Thr Gly Gly Ser
1               5
```

```
<210> SEQ ID NO 28
<211> LENGTH: 6
<212> TYPE: PRT
<213> ORGANISM: Artificial Sequence
<220> FEATURE:
<223> OTHER INFORMATION: linker sequence

<400> SEQUENCE: 28

Gly Gly Ser Gly Gly Thr
1               5

<210> SEQ ID NO 29
<211> LENGTH: 10
<212> TYPE: PRT
<213> ORGANISM: Artificial Sequence
<220> FEATURE:
<223> OTHER INFORMATION: full or partial sensor sequence

<400> SEQUENCE: 29

Ala Arg Glu Thr Phe Gln Ala Phe Arg Thr
1               5                   10
```

CIRCULARLY PERMUTATED HALOALKANE TRANSFERASE FUSION MOLECULES

CROSS-REFERENCE TO RELATED APPLICATIONS

This is the U.S. National Stage of International Patent Application No. PCT/EP2020/060785 filed on Apr. 16, 2020, which claims priority to European Patent Application No. 19169689.7 filed on Apr. 16, 2019, and European Patent Application No. 19206641.3 filed on Oct. 31, 2019.

The present invention relates to polypeptide sequences comprising a haloalkane transferase enzymatic activity, which are capable of modulating this enzymatic activity in response to an environmental stimulus.

Methods for integrating biochemical processes over time are of great scientific interest. These biochemical processes encompass, for example, protein-protein interactions, changes in metabolite concentration or protein sub-cellular (re) localization. Currently, these biochemical processes are mainly studied employing real time fluorescence microscopy using tailor-made biosensors. However, these approaches suffer from several drawbacks. Notably in neurobiology, experimental setups required for fluorescence imaging in vivo restrict animal movement and affect the studied behaviours. Biochemical processes occurring in organs such as the intestines or the heart are complex to resolve at the cellular level due to their inherent physiological movements. More generally, fluorescence microscopy is restricted to confined fields of view and tissue depth. Despite great improvements in equipment, image processing and biosensor designs, it remains impossible to study fundamental events in complete rodent organs in vivo by fluorescence microscopy.

An alternative approach consists in the recording of biochemical processes that can be read out at a later time point. This recording process is defined as integration. It leads to an irreversible mark being accumulated over time in response to the biochemical process under investigation.

The post hoc evaluation of experiments is not only valuable for in vivo studies, but can also be beneficial for cell-based assays. Especially in the case of rarely occurring biochemical processes, the signal integration over time can improve the readout due to an enhanced signal to noise ratio. In high throughput screenings, signal integration could offer a snapshot of the studied phenomenon, thereby increasing multiplexing and reducing costs by replacing lengthy recordings via real-time microscopy. Finally, using fluorescent substrates, cell populations can be identified, and eventually sorted, based on their metabolic/signalling profile for downstream analysis and/or treatments.

Based on the above-mentioned state of the art, the objective of the present invention is to provide means and methods for integrating biochemical processes over time. This objective is attained by the subject-matter of the independent claims of the present specification.

Based on the self-labelling protein HaloTag™ 7 (PDB 6Y7A), the inventors provide a chemogenetic integrator family of proteins that have been engineered to irreversibly react with chloroalkane substrates in response to a given biochemical process. These integrators consist of split circular permutants of HaloTag™ 7 (PDB 6Y7A) that change conformation in response to a biochemical process and invoke labelling activity. In a typical experiment, the recording window is defined by the time presence of the chloroalkane substrate that can (covalently) label the chemogenetic integrator. Different labelling substrates can be employed sequentially in pulse-chase experiments offering the possibility to study different successive phenomena with the same biological sample.

SUMMARY OF THE INVENTION

The invention relates to fusion proteins comprising a circularly permutated haloalkane transferase split into two parts, which are catalytically active when brought into close spatial proximity by a sensor polypeptide module but are otherwise catalytically inactive.

Specifically, the invention relates to a modular polypeptide system comprising a first partial effector sequence comprising
- an N-terminal first effector sequence part characterized by SEQ ID NO 002 or by a sequence ≥90% identical to SEQ ID NO 002,
- a C-terminal first effector sequence part characterized by SEQ ID NO 003 or by a sequence ≥90% identical to SEQ ID NO 003,
- an internal cpHalo linker consisting of 10 to 35 amino acids, wherein the internal cpHalo linker connects the C-terminus of the N-terminal first effector sequence part to the N-terminus of the C-terminal first effector sequence part;

connected to a sensor module sequence, which is connected to a second partial effector sequence comprising or essentially consisting of a sequence selected from SEQ ID NO 006 (PEP1) and 007 (PEP2) or a sequence ≥75% identical to SEQ ID NO 007 (PEP2),
wherein
the first and second partial effector sequences together constitute a circularly permuted haloalkane dehalogenase, and are capable, when brought into close proximity of each other, to effect covalent attachment of a halogen alkane moiety, and wherein the sensor module is selected from a. a single sensor polypeptide capable of undergoing conformational change from a first confirmation to a second confirmation depending on the presence or concentration of an analyte compound, wherein
  in the first conformation, the first and second partial effector sequences are in close proximity (which leads to the first and second partial effector sequences constituting a catalytically active entity), and
  in the second conformation, the first and second partial effector sequences are not in close proximity (which leads to the first and second partial effector sequences constituting a catalytically inactive entity),
when the first partial effector sequence is attached to the C-terminus of the sensor module (the single sensor polypeptide) and the second partial effector sequence is attached to the N-terminus of the sensor module (the single sensor polypeptide)
and b. a sensor polypeptide pair comprising a first sensor polypeptide and a second sensor polypeptide, wherein the first sensor polypeptide is covalently attached through a peptide bond to the first partial effector sequence and the second sensor polypeptide is covalently attached to the second partial effector sequence, the first sensor polypeptide and the second sensor polypeptide are capable of specific molecular interaction (protein-protein binding), and the first and second sensor polypeptides are part of separate polypeptide chains.

A second aspect of the invention relates to nucleic acids encoding the fusion protein of the invention. Alternatively, nucleic acids are provided that encode the two parts of the circularly permutated haloalkane transferase (the first partial effector sequence and the second partial effector sequence). These nucleic acid sequences encoding the first and second partial effectors are useful for making other fusion proteins capable of sensing analyte concentrations or protein-protein interactions with yet unexplored interaction partners or sensor modules.

Furthermore, the invention provides expression systems, cells and transgenic non-human animals comprising the fusion proteins or encoding nucleic acids of the invention. Similarly, kits providing the nucleic acids for rapid construction of transgenic expression constructs and suitable substrate compounds are encompassed by the invention.

DETAILED DESCRIPTION OF THE INVENTION

Terms and Definitions

The term fluorescent dye in the context of the present specification relates to a small molecule capable of fluorescence in the visible or near infrared spectrum. Examples for fluorescent labels or labels presenting a visible colour include, without being restricted to, fluorescein isothiocyanate (FITC), rhodamine, allophycocyanine (APC), peridinin chlorophyll (PerCP), phycoerithrin (PE), Alexa Fluors™ (Life Technologies™, Carlsbad, CA, USA), DYLIGHT™ fluors™ (Thermo Fisher™ Scientific, Waltham, MA, USA) ATTO Dyes (ATTO-TEC GmbH, Siegen, Germany), BODIPY™ Dyes (4,4-difluoro-4-bora-3a,4a-diaza-s-indacene based dyes) and the like.

Amino acid sequences are given from amino to carboxyl terminus. Capital letters for sequence positions refer to L-amino acids in the one-letter code (Stryer, Biochemistry, 3$^{rd}$ ed. p. 21). Lower case letters for amino acid sequence positions refer to the corresponding D- or (2R)-amino acids.

J is isoleucine or leucine.

The term polypeptide in the context of the present specification relates to a molecule consisting of 50 or more amino acids that form a linear chain wherein the amino acids are connected by peptide bonds. The amino acid sequence of a polypeptide may represent the amino acid sequence of a whole (as found physiologically) protein or fragments thereof.

The term peptide in the context of the present specification relates to a molecule consisting of up to 50 amino acids, in particular 8 to 30 amino acids, more particularly 8 to 15 amino acids, that form a linear chain wherein the amino acids are connected by peptide bonds.

In the context of the present specifications the terms sequence identity and percentage of sequence identity refer to the values determined by comparing two aligned sequences. Methods for alignment of sequences for comparison are well-known in the art. Alignment of sequences for comparison may be conducted by the local homology algorithm of Smith and Waterman, Adv. Appl. Math. 2:482 (1981), by the global alignment algorithm of Needleman and Wunsch, J. Mol. Biol. 48:443 (1970), by the search for similarity method of Pearson and Lipman, Proc. Nat. Acad. Sci. 85:2444 (1988) or by computerized implementations of these algorithms, including, but not limited to: CLUSTAL, GAP, BESTFIT, BLAST, FASTA and TFASTA. Software for performing BLAST analyses is publicly available, e.g., through the National Center for Biotechnology-Information (blast.ncbi.nlm.nih.gov/).

One example for comparison of amino acid sequences is the BLASTP algorithm that uses the default settings: Expect threshold: 10; Word size: 3; Max matches in a query range: 0; Matrix: BLOSUM62; Gap Costs: Existence 11, Extension 1; Compositional adjustments: Conditional compositional score matrix adjustment. One such example for comparison of nucleic acid sequences is the BLASTN algorithm that uses the default settings: Expect threshold: 10; Word size: 28; Max matches in a query range: 0; Match/Mismatch Scores: 1.-2; Gap costs: Linear. Unless stated otherwise, sequence identity values provided herein refer to the value obtained using the BLAST suite of programs (Altschul et al., J. Mol. Biol. 215:403-410 (1990)) using the above identified default parameters for protein and nucleic acid comparison, respectively.

The term having substantially the same activity in the context of the present specification relates to the activity of an effector polypeptide pair, particularly SEQ ID NO:004 and SEQ ID NO 007 (PEP2), i.e. haloalkane transferase activity. A polypeptide qualified as having substantially the same activity does not necessarily show the same quantity of activity as the reference polypeptide; in the particular case of the present invention, a reduction of enzymatic turnover with respect to the reference peptide cpHalo might indeed be desirable for certain applications. As laid out below, for purposes of distinguishing polypeptides covered by the present inventions from those that are not covered, the inventors propose a threshold of activity of $10^2$ s$^{-1}$M$^{-1}$ in the standard assay as laid out in Example 9, with Halo-CPY as the substrate.

For purposes wherein the above definition of activity is not applicable, 3 standard deviations above background with regard to haloalkane transferase activity shall be taken as the reference threshold for having substantially the same activity. In certain embodiments, at least 5 standard deviations are used as the reference threshold. In certain particular embodiments, at least 10 standard deviations are used as the reference threshold.

In the context of the present specification, the term amino acid linker refers to a polypeptide of variable length that is used to connect two polypeptides in order to generate a single chain polypeptide. Unless specified otherwise, exemplary embodiments of linkers useful for practicing the invention specified herein are oligopeptide chains consisting of 1, 2, 3, 4, 5, 10, 20, 30, 40 or 50 amino acids.

In the context of the present specification, the term Gltl is an abbreviation for bacterial periplasmic glutamate binding protein (Uni-Prot-ID: H4UFY3).

A first aspect of the invention relates to a modular analyte sensor polypeptide system (also named modular polypeptide herein) that comprises, or essentially consists of, a split effector polypeptide sequence having HaloTag™ 7 activity, which is reconstituted by a sensor polypeptide module.

The modular analyte sensor polypeptide system that comprises, or essentially consists of, a first partial effector polypeptide sequence (cpHaloA) comprising or essentially consisting of an N-terminal first effector sequence part characterized by SEQ ID NO 002, or by a sequence at least (≥) 90% identical (particularly ≥93%, 95%, 97% or ≥98% identical) to SEQ ID NO 002, a C-terminal first effector sequence part characterized by SEQ ID NO 003, or by a sequence at least (≥) 90% identical (particularly ≥93%, 95%, 97% or ≥98% identical) to SEQ ID NO 003, and an internal cpHalo linker consisting of 10 to 35 amino acids.

The internal cpHalo linker connects the C-terminus of the N-terminal first effector sequence part to the N-terminus of the C-terminal first effector sequence part.

In certain embodiments, the cpHalo linker consists of 12 to 20 amino acids. In certain particular embodiments, the cpHalo linker consists particularly of ca. 15 amino acids.

The first partial effector polypeptide sequence is covalently connected as part of a peptide chain via its N-terminus to a sensor module polypeptide sequence, which is connected as part of a peptide chain to a second partial effector peptide sequence, which complements the cpHaloA sequence and reconstitutes the haloalkane transferase activity. It comprises or essentially consists of a sequence selected from SEQ ID NO 006 (PEP1) and 007 (PEP2) or a sequence at least (≥) 75% identical (particularly ≥80%, 85%, 90% or ≥95% identical) to SEQ ID NO 007 (PEP2).

The first and second partial effector sequences together constitute a circularly permuted haloalkane dehalogenase, and are capable, when brought into close proximity of each other, to effect covalent attachment of a halogen alkane moiety to the first effector sequence.

Certain variations of the modular analyte sensor polypeptide system of the invention may be designed to show significantly less activity than the examples provided herein. The native HaloTag™ 7 (PDB 6Y7A) and its circularly permutated form are very active and for some applications, a lower/slower activity may be desirable. One example is the recording of neuronal activity over a long period of time, where highly active systems may be prone to oversaturate the system rapidly and prevent the recording of events unfolding over long periods.

The threshold for the combination of split effector modules with a sensor module sequence as defined herein, is to provide a minimal activity of $10^2$ $s^{-1}M^{-1}$ in the standard assay as laid out in Example 9.

In certain embodiments, the combination of split effector modules consisting of a first effector sequence ≥90% identical to SEQ ID NO 004, or to a construct consisting of SEQ ID NO 002 and SEQ ID NO 003 joined by a linker, and a second partial effector sequence, are characterized by at least 3 standard deviation (≥3 σ) values above background signal, particularly ≥5 σ or even ≥10 σ values above background signal, when the variant of SEQ ID NO 004 is brought into close spatial proximity with SEQ ID NO 007 (PEP2).

It is understood that for purposes of computing sequence identity, the contributions of SEQ ID NO 002 and SEQ ID NO 003 should be weighed, while the linker molecule joining the two sequences can vary substantially without affecting the function of the resulting construct.

In certain embodiments, the combination of split effector modules consisting of a first effector sequence ≥90% identical to SEQ ID NO 004, or to a construct consisting of SEQ ID NO 002 and SEQ ID NO 003 joined by a linker, and a second partial effector sequence are characterized by at least 0.5%, particularly ≥1% or ≥2% of the activity of SEQ ID NO 004 when brought into close spatial proximity with SEQ ID NO 007 (PEP2).

In certain embodiments, the combination of split effector modules consisting of a first effector sequence ≥90% identical to SEQ ID NO 004, or to a construct consisting of SEQ ID NO 002 and SEQ ID NO 003 joined by a linker, and a second partial effector sequence are characterized by at least 5% of the activity of SEQ ID NO 004 when SEQ ID NO 004 is brought into close spatial proximity with SEQ ID NO 007 (PEP2).

In certain embodiments, the combination of split effector modules consisting of a first effector sequence ≥90% identical to SEQ ID NO 004, or to a construct consisting of SEQ ID NO 002 and SEQ ID NO 003 joined by a linker, and a second partial effector sequence are characterized by at least 15%, 25%, 40% or even 50% of the activity of SEQ ID NO 004 when brought into close spatial proximity with SEQ ID NO 007 (PEP2).

The sensor module (also named sensor module sequence herein) is selected from a single sensor polypeptide and a sensor polypeptide pair.

The sensor module can be a single sensor polypeptide capable of undergoing conformational change from a first confirmation to a second confirmation depending on the presence or concentration of an analyte compound in the vicinity of the sensor module sequence. The conformational change may also be effected by the absence of an analyte, or its removal from the environment. In the first conformation, the first and second partial effector sequences are in close proximity when the first partial effector sequence is attached to the C-terminus of the sensor module (the single sensor polypeptide) and the second partial effector sequence is attached to the N-terminus of the sensor module (the single sensor polypeptide), in other words their proximity leads to the first and second partial effector sequences constituting a catalytically active entity.

In contrast, in the second conformation, the first and second partial effector sequences are not in close proximity and thus lead to the first and second partial effector sequences constituting a catalytically inactive entity when the first partial effector sequence is attached to the C-terminus of the sensor module and the second partial effector sequence is attached to the N-terminus of the sensor module sequence.

The C-terminus of the single sensor polypeptide is covalently attached, directly through a peptide bond or through a linker peptide, to the N-terminus of the first partial effector sequence and the N-terminus of the single sensor polypeptide is covalently attached to the C-terminus of the second partial effector sequence.

Alternatively, the sensor module can be a sensor polypeptide pair comprising a first sensor polypeptide and a second sensor polypeptide, wherein the C-terminus of the first sensor polypeptide is covalently attached, directly through a peptide bond or through a linker peptide, to the N-terminus of the first partial effector sequence and the N-terminus of the second sensor polypeptide is covalently attached to the C-terminus of the second partial effector sequence, wherein the first sensor polypeptide and the second sensor polypeptide are capable of specific molecular interaction (protein-protein binding). In this alternative, the first and second sensor polypeptides are part of separate polypeptide chains.

The second partial effector sequence complements the first partial effector sequence when brought into close proximity. The inventors have found that SEQ ID NO 006 (PEP1) and 007 (PEP2), which differ by a C-terminal threonine residue, are the most effective in doing so. This does not preclude further future evolution of the peptide for the purpose of increasing the affinity of the partial sequences to one another, or for other purposes. The one extra threonine in the PEP2 sequence leads to a significant increase in the reaction speed in combination with the calmodulin/M13 sensor system, but when employed in combination with a FKPB/FRB sensor system, it does not have much effect.

The skilled artisan will realize that variations in the second partial effector sequence may also be tolerated depending on the contribution of the individual position to the structure. Ala145, Arg146, Thr148, Phe149, Phe152 and Arg153, which are known to interact with the protein, are less likely to be replaceable with residues of similar chemical properties (or even less similar ones). Amino acids that are more solvent exposed (i.e. Glu147, Gln150, Ala151 and Thr154) would a priori be less essential to maintain as exactly the same. In the hands of the inventors, mutation studies confirmed these statements. The position Ala150 revealed tolerant for modification and positions Arg146 and Thr148 revealed important for the integrator function (in the context of calcium signal integration).

A table of AA with alpha helix propensity may be used to hierarchize the AA since the peptide has to fold to alpha-helical structure. Such table can be found in Pace et al., Biophysical Journal. 75. pp. 422-427. doi: 10.1016/s0006-3495 (98) 77529-0.

In certain embodiments, the first partial effector polypeptide sequence and the second partial effector sequence, when brought into close proximity of each other, together have at least 0.5%, particularly ≥1% or ≥2% of the biological activity of SEQ ID NO 001. In certain embodiments, the first partial effector polypeptide sequence and the second partial effector sequence, when brought into close proximity of each other, together have at least an activity of $10^2$ $s^{-1}M^{-1}$ in the standard assay as laid out in Example 9.

The activity of SEQ ID NO 001, for the purposes of defining which sequences are encompassed by the definition of the previous sentence and other such definitions contained within this specification, is performance of the sequence in the fluorescence polarization assay of Example 9. If not otherwise specified, the activity is measured according to the protocol given in Example 9 using Halo-CPY (see the substrate table below) for purposes of comparison of biological activities.

In certain embodiments, the internal cpHalo linker comprises or consists of the amino acids G, A, J, S, T, P, C, V, M, particularly wherein the cpHalo linker comprises or consists of the amino acids G, S, A and T.

In particular embodiments, the cpHalo linker is $(GG\Sigma)_n$ with n being an integer and n≥3 (particularly n is 4, 5, 6, 7 or 8), and with Σ selected from S and T.

In particular embodiments, the cpHalo linker is $(GGS)_n$ with n being an integer and n≥3 (particularly n is 4, 5, 6, 7 or 8).

In particular embodiments, the cpHalo linker is $(GGT)_n$ with n being an integer and n≥3 (particularly n is 4, 5, 6, 7 or 8).

In particular embodiments, the cpHalo linker is $(G\Sigma G)_n$ or $(GG\Sigma)_n$ with n being an integer and n≥3 (particularly n is 4, 5, 6, 7 or 8), and with each Σ independently selected from S and T.

In particular embodiments, the cpHalo linker is $(TT\Sigma)_n$ with n being an integer and n≥3 (particularly n is 4, 5, 6, 7 or 8), and with each Γ independently from any other Γ being selected being from A, G and V, and each Σ independently being selected from S and T.

With regard to the length and sequence composition of the cpHalo linker, the inventors' results indicate that any linker having an equivalent length of 10, optimally 12 amino acids is expected to function. Exceptions are linkers that, because of their predicted structure, are expected to interfere with the solubility of the resulting protein. The inventors have decided not to pursue exploration of linkers longer than 25 amino acids but see no reason why such lengths should not be expected to function.

Important considerations at the time of choosing the linker sequence have been solubility and flexibility. The actual cpHalo linker sequence chosen for the examples disclosed herein is GGTGGSGGTGGSGGS (SEQ ID NO:005), but the skilled person will readily be able to vary this sequence in composition and length based on the teaching herein and the knowledge available on linker design, as exemplified by Chen et al., Advanced Drug Delivery Reviews 65 (2013), 1357-1369 and Evers et al., Biochemistry 2006, 45, 13183-13192.

In certain embodiments, the first partial effector polypeptide sequence comprises or essentially consists of SEQ ID NO 004, or a sequence at least (≥) 90% identical (particularly ≥93%, 95%, 97% or ≥98% identical) to SEQ ID NO 004, wherein the first and second partial effector sequences together are characterized by at least 1% of the activity of SEQ ID NO 004 being in close spatial proximity with SEQ ID NO 007 (PEP2).

In certain particular embodiments, the first partial effector polypeptide sequence comprises or essentially consists of a sequence at least (≥) 90% identical (particularly ≥93%, 95%, 97% or ≥98% identical) to SEQ ID NO 004, and the first and second partial effector sequences together are characterized by ≥5%, 10%, 17% or 33% of the activity of SEQ ID NO 004 being in close spatial proximity with SEQ ID NO 007 (PEP2).

The sensor and effector modules may be connected directly to one another, but in order to allow some adjustment of structure, the skilled artisan is aware that linker sequences can be employed to connect the modules.

In certain embodiments, the first partial effector polypeptide sequence is connected to the sensor module polypeptide sequence (also named sensor module sequence herein) by a first intermodular linker peptide sequence, and/or the second partial effector polypeptide sequence is connected to the sensor module polypeptide sequence by a second intermodular linker polypeptide sequence.

The inventors found particularly useful first intermodular linker sequences characterized by $(GGY')_n$ with n being an integer and n≤4 (particularly n is 1, 2 or 3), with Y' selected from G, S and T.

Similarly, the inventors found particularly useful second intermodular linker sequences characterized by $(GG'Y)_n$ with n being an integer and n≤4 (particularly n is 1, 2 or 3), with Y selected from G, S and T.

In particular embodiments, the first and/or second intermodular linker can be a one or two amino acid linker GY, YG, Y, G or Y alone, with Y selected from G, S and T. Alanine is one example of an amino acid that can substitute one of G, S and T in the above sequences.

Particular importance should be given to the absence of background labeling and a noticeable signal over background once reconstituted in the presence of the analyte of interest. Depending on the sensor module, the skilled person will be able to vary intermodular linker sequences to test which length will give the best results for a given combination of modules.

The sequence alternatives exemplarily laid out for the cpHalo linker above, as regards sequence composition, not linker length, apply to the intermodular linkers also.

In certain embodiments, the sensor module sequence is a single sensor polypeptide that consists of an N-terminal first partial sensor sequence and a C-terminal second sensor sequence connected by a sensor linker sequence.

In certain embodiments, the sensor module sequence is a single sensor polypeptide that consists of an N-terminal first partial sensor sequence and a C-terminal second sensor sequence connected by a rigid sensor linker sequence such as can be attained by an oligoproline sequence, particularly by a $P_n$ sequence with n being an integer between 15 and 35.

In certain embodiments, the sensor linker sequence is a polyproline sequence such as exemplified in the previous paragraph, but contains short inserts of flexible motifs such as exemplified (but not limited to) (GGΨ)$_n$ with n being an integer and n selected from 1, 2 and 3, and with Ψ selected from G, S and T. Similarly, the inserted linker may have a shorter period such as GΨ, ΨG, ΨΨ, G or Ψ alone. One example that has worked well in the inventors' hands is a fifteen-proline stretch followed by two repeats of GGS, followed again by 15 prolines. Such design can facilitate a hinge in the spring formed by the prolines. The inventors have observed that a linker, which is mostly rigid, offers certain advantages but the linker sequence can be varied across a broad spectrum of sequences without abrogating activity of the final construct. Again, it should be remembered that in certain applications, a lower activity which still is clearly distinguishable from background noise, may actually be preferable over highly active constructs. Brun et al. (J Am Chem Soc 2011, 133 (40) 16235-16242) teaches linker variation that can be adapted to the present invention. Reference is made again to Chen et al., (ibid.) and Evers et al. (ibid.) mentioned above.

In certain embodiments, the first partial sensor sequence and the second partial sensor sequence are selected from a calmodulin-binding peptide and a calmodulin polypeptide.

In certain particular embodiments, the first partial sensor sequence is a calmodulin polypeptide and the second partial sensor sequence is a calmodulin-binding peptide.

A great number of different calmodulin variants and binding peptides exist, as have been described, inter alia, in Zhao et al., Science 2011 vol 333 (6051) 1888-91 doi: 10.1126/science.1208592; Wu et al., 2013 ACS Chemical Neuroscience vol 4 (6) 963-972 doi: 10.1021/cn400012b; Horikawa et al, 2010 Nat Methods. 2010 September;7 (9): 729-32 doi: 10.1038/nmeth.1488; Chen et al. Nature. 2013 Jul. 18;499 (7458): 295-300. doi: 10.1038/nature12354; Moeyaert et al. Nat Commun. 2018 Oct. 25;9 (1): 4440. doi: 10.1038/s41467-018-06935-2; Dana et al., 2018 bioRxiv 434589; Gao et al., 2015 doi: 10.1038/nn.4016; Lee et al., 2017 doi: 10.1038/nbt.3902; Minderer et al., 2012 doi: 10.1113/jphysiol.2011.219014; De Juan-Sanz et al., 2017 doi: 10.1016/j.neuron.2017.01.010; Ding et al., 2015 doi: 10.1038/nmeth.3261 and Akerboom et al 2011., doi: 10.1523/JNEUROSCI.2601-12.2012.

In certain embodiments, the calmodulin polypeptide is or comprises SEQ ID NO 009 (CaM), or a sequence at least 90% identical to SEQ ID NO 009 (CaM) and having substantially the same biological activity, and the calmodulin-binding peptide is or comprises SEQ ID NO 008 (M13).

In certain embodiments, the sensor module is constituted by a sensor polypeptide pair comprising a first sensor peptide that is or comprises a calmodulin binding peptide, exemplified by SEQ ID NO 008 (M13), and a second sensor polypeptide that is or comprises a calmodulin polypeptide, particularly SEQ ID NO 009 (CaM), or a sequence at least 90% identical to SEQ ID NO 009 (CaM) and having substantially the same activity. The first sensor peptide is covalently attached through a peptide bond to the first partial effector sequence and the second sensor polypeptide is covalently attached to the second partial effector sequence, and the first and second sensor polypeptides are part of separate polypeptide chains.

In particular embodiments, the calmodulin binding peptide is selected from any of the calmodulin binding peptides known in the art. Longer variants have been reported that will work in the same fashion, see the quoted references above.

In certain particular embodiments, the first partial effector sequence is connected to the C-terminus of the first sensor peptide by a first intermodular linker sequence having 2 to 6 amino acids, and/or the second partial effector sequence is connected to the N-terminus of the second sensor polypeptide by a second intermodular linker having 2 to 6 amino acids.

In certain more particular embodiments, the first intermodular linker sequence and the second intermodular linker sequence are dipeptides or tripeptides, the amino acid constituents of which are each independently selected from G, S and T residues.

In certain embodiments, the modular polypeptide is characterized by a first polypeptide sequence consisting or comprising SEQ ID NO 010 (SPLT1) or a sequence at least 90% identical to SEQ ID NO 010 (SPLT1), and a second polypeptide sequence SEQ ID NO 011 (SPLT2) or a sequence at least 90% identical to SEQ ID NO 011 (SPLT2), wherein the first and the second polypeptide sequence together have at least 0.5%, particularly ≥1% or ≥2% of the activity of the combination of SEQ ID NO 010 (SPLT1) and SEQ ID NO 011 (SPLT2). In certain embodiments, the sensor module is constituted by a single sensor polypeptide, comprising, from N to C-terminus,

- a calmodulin polypeptide, particularly SEQ ID NO 009 (CaM), or a sequence at least 90% identical to SEQ ID NO 009 (CaM) and having substantially the same activity;
- a peptide sensor linker sequence, particularly a polyproline-type rigid helix, more particularly a $P_n$ proline polypeptide wherein n is selected from an integer from 15 to 35, optionally flanked by 1-4 amino acids, or a polyproline sequence interrupted by a short flexible stretch of 1 to 10 residues selected from G, T, S, A;
- a calmodulin binding peptide (second partial sensor sequence), particularly a sequence comprising or consisting of SEQ ID NO 008 (M13).

In certain embodiments, the modular polypeptide of the invention comprises or consists of a sequence selected from SEQ ID NO 013 (CONF1) and SEQ ID NO 014 (CONF2), or a sequence at least 90% identical to SEQ ID NO 013 (CONF1) or SEQ ID NO 014 (CONF2) having at least 0.5%, particularly ≥1% or ≥2% of the activity of SEQ ID NO 013 (CONF1).

In certain embodiments, the sensor module sequence comprises or essentially consists of a. an N-terminal part of a glutamate binding protein, particularly wherein the first sensor polypeptide is or comprises SEQ ID NO 020 (GLT1), or a sequence at least 90% identical to SEQ ID NO 020 (GLT1), and a C-terminal part of a glutamate binding protein, particularly wherein the second sensor polypeptide is or comprises SEQ ID NO 021 (GLT2), or a sequence at least 90% identical to SEQ ID NO 021 (GLT2) and having substantially the same biological activity, particularly a bacterial periplasmic glutamate binding protein, more particularly from Gltl;

wherein the combination of the first sensor polypeptide and the second sensor polypeptide and have substantially the same biological activity as a combination of SEQ ID NO 020 (GLT1) and SEQ ID NO 021 (GLT2);

or b. a sequence at least (2) 90% identical to construct consisting of SEQ ID NO 020 (GLT1) joined by a polypeptide linker to SEQ ID NO 021 (GLT2), particularly wherein the sensor module sequence is or comprises SEQ ID NO 022 (GLT3), or a sequence at least 90% identical to SEQ ID NO 022 (GLT3) and having substantially the same biological activity.

In certain embodiments, the modular polypeptide is characterized by a first polypeptide sequence consisting of or comprising SEQ ID NO 023 (GLTIND1), or a sequence at least 90% identical to SEQ ID NO 023 (GLTIND1), and a second polypeptide sequence SEQ ID NO 024 (GLTIND2) or a sequence at least 90% identical to SEQ ID NO 024 (GLTIND2), wherein the first polypeptide sequence and the second polypeptide sequence together have at least 0.5%, particularly ≥1% or ≥2% of the activity of SEQ ID NO 025 (GLTIND3).

In certain embodiments, the sensor module is constituted by a sensor polypeptide pair comprising:
a first sensor polypeptide that is or comprises an FKBP12 polypeptide, particularly wherein the FKBP12 polypeptide is or comprises SEQ ID NO 015 (FKBP), or a sequence at least 90% identical to SEQ ID NO 015 (FKBP) and having substantially the same biological activity,
and a second sensor polypeptide that is or comprises an FRB peptide, particularly wherein the FRB peptide is or comprises SEQ ID NO 016 (FRB), or a sequence at least 90% identical to SEQ ID NO 016 (FRB) and having substantially the same biological activity,
wherein the first sensor polypeptide is covalently attached through a peptide bond to the first partial effector sequence and the second sensor polypeptide is covalently attached to the second partial effector sequence, and the first and second sensor polypeptides are part of separate polypeptide chains.

In certain particular embodiments, the first partial effector sequence is connected to the C-terminus of the first sensor polypeptide by a first intermodular linker sequence having 2 to 9 amino acids, and/or the second partial effector sequence is connected to the N-terminus of the second sensor polypeptide by a second intermodular linker having 2 to 9 amino acids.

In certain more particular embodiments, the first intermodular linker sequence and the second intermodular linker sequence are tripeptides, the amino acid constituents are each independently selected from G, S and T residues.

In certain embodiments, the modular polypeptide is characterized by a first polypeptide sequence consisting or comprising SEQ ID NO 017 (RAPIND1) or a sequence at least 90% identical to SEQ ID NO 017 (RAPIND1) and a second polypeptide sequence selected from SEQ ID NO 018 (RAPIND2) and SEQ ID NO 019 (RAPIND3) or a sequence at least 90% identical to SEQ ID NO 018 (RAPIND2), wherein the first and the second polypeptide sequence together have at least 0.5%, particularly ≥1% or ≥2% of the activity of the combination of SEQ ID NO 017 (RAPIND1) and SEQ ID NO 018 (RAPIND2). In certain particular embodiments, the first and the second polypeptide sequence together have at least 5%, 10%, 15%, 20% or 33% of the activity of the combination of SEQ ID NO 017 (RAPIND1) and SEQ ID NO 018 (RAPIND2).

Another aspect of the invention relates to nucleic acid sequence, or a plurality of nucleic acid sequences, encoding a modular analyte sensor polypeptide according to the invention as described in any of the aspects, embodiments or examples herein.

The invention may be similarly embodied by a combination of nucleic acid sequences comprising
a first nucleic acid sequence encoding a first partial effector polypeptide sequence, wherein the encoded first partial effector sequence comprises, from N to C-terminus, SEQ ID NO 002, or a sequence at least (≥) 90% identical (particularly ≥93%, 95%, 97% or ≥98% identical) to SEQ ID NO 002,
a polypeptide linker sequence having 10-35 (particularly approx. 15) amino acids, more particularly 12-20 amino acids selected from G, A, J, S, T,
SEQ ID NO 003 or a sequence at least (≥) 90% identical (particularly ≥93%, 95%, 97% or ≥98% identical) to SEQ ID NO 003;
a second nucleic acid sequence encoding a second partial effector peptide sequence characterized by SEQ ID NO 006 (PEP1), 007 (PEP2) or encoding a sequence at least (≥) 95% identical (particularly ≥96%, 97%, 98% or ≥99% identical) to SEQ ID NO 006 (PEP1),
wherein the first and second partial effector polypeptide sequences together constitute a circularly permuted haloalkane dehalogenase, and are capable, when brought into close proximity of each other, to effect covalent attachment of a halogen alkane moiety. Again, for the purpose of defining sequence variants deemed to be encompassed by the invention, the threshold for the combination of split effector modules combinable with a sensor module sequence is an activity of $10^2$ $s^{-1}M^{-1}$ in the standard assay as laid out in Example 9.

In certain embodiments, the split effector modules, when combined under conditions that favour spatial proximity as in the examples and embodiments given above, show at least 0.5%, particularly ≥1% or ≥2% of the activity of SEQ ID NO 001. In certain embodiments, the split effector modules, when combined under conditions that favour spatial proximity as in the examples and embodiments given above, together have at least an activity of $10^2$ $s^{-1}M^{-1}$ in the standard assay as laid out in Example 9.

This combination may be provided for example as nucleic acid vectors ready for insertion of a nucleic acid encoding an experimental sensor module, or for fusion to a pair of encoded peptides the interaction of which is to be interrogated by the complemented activity of the effector module.

Another aspect of the invention relates to a nucleic acid expression system comprising the nucleic acid sequence according to the previously described aspect, or a combination of nucleic acids encoding the effector module pair of sequences as described herein, each nucleic acid sequence being under control of a promoter sequence.

Another aspect of the invention relates to an isolated cell or a transgenic non-primate animal comprising the nucleic acid expression system or the nucleic acid sequences as disclosed herein, particularly wherein the promoter is operable in said cell.

Likewise, the invention may be embodied by a kit comprising a nucleic acid sequence or a nucleic acid expression system as disclosed herein, and a HaloTag™ 7 substrate, particularly a haloalkane moiety covalently linked to a fluorescent dye.

The halotag™ system was first published by Los et al. (ACS Chemical Biology 2008 Vo. 3 (6) 373-382; AQS79242). It is reviewed by England et al. Bioconjugate Chemistry 2015, 26, 975-986. Patent documents showing general aspects of the halotag™ system and substrate molecules useful therein include U.S. Pat. No. 8,202,700B2, U.S. Pat. No. 7,867,726, PCT/US2013/074756, U.S. Pat. No. 9,927,430B2, U.S. Pat. No. 10,168,323B2 and US2014322738, all of which are incorporated herein by reference.

Exemplary fluorophore substrates that can be employed with the present invention include, but are not limited to, the fluorophore substrate compounds given in the following table:

| Code | IUPAC Name; Source/DOI |
| --- | --- |
| Halo-TMR | N-(9-(2-carboxy-5-((2-(2-((6-chlorohexyl)oxy) ethoxy)ethyl)carbamoyl)phenyl)-6-(dimethylamino)-3H-xanthen-3-ylidene)-N-methylmethanaminium; Promega Corp. #G8251 |
| Halo-TMR-az | 1-(6-(azetidin-1-yl)-9-(2-carboxy-5-((2-(2-((6-chlorohexyl)oxy)ethoxy)ethyl)carbamoyl)-phenyl)-3H-xanthen-3-ylidene)azetidin-1-ium; DOI:10.1038/nmeth.3256 |
| Halo-TMR-az-F2 | 1-(9-(2-carboxy-5-((2-(2-((6-chlorohexyl)oxy) ethoxy)ethyl)carbamoyl)phenyl)-6-(3-fluoroazetidin-1-yl)-3H-xanthen-3-ylidene)-3-fluoroazetidin-1-ium; DOI: 10zz.1038/nmeth.4403 |
| Halo-TMR-az-F4 | 1-(9-(2-carboxy-5-((2-(2-((6-chlorohexyl)oxy) ethoxy)ethyl)carbamoyl)phenyl)-6-(3,3-difluoroazetidin-1-yl)-3H-xanthen-3-ylidene)-3,3-difluoroazetidin-1-ium; DOI: 10zz.1038/nmeth.4403 |
| Halo-CPY | N-(10-(2-carboxy-5-((2-(2-((6-chlorohexyl) oxy)ethoxy)ethyl)carbamoyl)phenyl)-7-(dimethylamino)-9,9-dimethylanthracen-2(9H)-ylidene)-N-methylmethanaminium; DOI: 10.1002/anie.201511018 |
| Halo-CPY-az | 1-(7-(azetidin-1-yl)-10-(2-carboxy-5-((2-(2-((6-chloro-hexyl)oxy)ethoxy)ethyl) carbamoyl)phenyl)-9,9-dimethylanthracen-2(9H)-ylidene)azetidin-1-ium; DOI: 10.1038/nmeth.3256 |
| Halo-CPY-az-F2 | 1-(10-(2-carboxy-5-((2-(2-((6-chlorohexyl)oxy) ethoxy)ethyl)carbamoyl)phenyl)-7-(3-fluoroazetidin-1-yl)-9,9-dimethylanthracen-2(9H)-ylidene)-3-fluoroazetidin-1-ium; DOI: 10zz.1038/nmeth.4403 |
| Halo-CPY-az-F4 | 1-(10-(2-carboxy-5-((2-(2-((6-chlorohexyl)oxy) ethoxy)ethyl)carbamoyl)phenyl)-7-(3,3-difluoroazetidin-1-yl)-9,9-dimethylanthracen-2(9H)-ylidene)-3,3-difluoroazetidin-1-ium; DOI: 10zz.1038/nmeth.4403 |
| Halo-SiR | N-(10-(2-carboxy-5-((2-(2-((6-chlorohexyl)oxy) ethoxy)ethyl)carbamoyl)phenyl)-7-(dimethylamino)-5,5-dimethyldibenzo[b,e]silin-3(5H)-ylidene)-N-methylmethanaminium; DOI: 10.1038/nchem.1546 |
| Halo-SiR-az | 1-(7-(azetidin-1-yl)-10-(2-carboxy-5-((2-(2-((6-chlorohexyl)oxy)ethoxy)ethyl)-carbamoyl) phenyl)-5,5-dimethyldibenzo [b,e]silin-3(5H)-ylidene) azetidin-1-ium; DOI: 10.1038/nmeth.3256 |
| Halo-SiR-az-F2 | 1-(10-(2-carboxy-5-((2-(2-((6-chlorohexyl)oxy)ethoxy) ethyl)carbamoyl)phenyl)-7-(3-fluoroazetidin-1-yl)-5,5-dimethyldibenzo[b,e]silin-3(5H)-ylidene)-3-fluoroazetidin-1-ium; DOI: 10zz.1038/nmeth.4403 |
| Halo-500R | (E)-N-(9-(2-carboxy-5-((2-(2-((6-chlorohexyl) oxy)ethoxy)ethyl)carbamoyl)phenyl)-6-((2,2,2-trifluoroethyl)amino)-3H-xanthen-3-ylidene)-2,2,2-trifluoroethan-1-aminium; DOI: 10.1002/anie.201511018 |
| Halo-560CP | (E)-N-(10-(2-carboxy-5-((2-(2-((6-chlorohexyl)oxy) ethoxy)ethyl)carbamoyl)phenyl)-9,9-dimethyl-7-((2,2,2-trifluoroethyl)amino)anthracen-2(9H)-ylidene)-2,2,2-trifluoroethan-1-aminium; DOI: 10.1002/chem.201701216 |
| Halo-580CP | (E)-N-(10-(2-carboxy-5-((2-(2-((6-chlorohexyl) oxy)ethoxy)ethyl)carbamoyl)phenyl)-9,9-dimethyl-7-(methylamino)anthracen-2(9H)-ylidene) methanaminium; DOI: 10.1002/anie.201511018 |
| Halo-515R | (Z)-N-(9-(2-carboxy-5-((2-(2-((6-chlorohexyl)oxy) ethoxy)ethyl)carbamoyl)phenyl)-2,7-difluoro-6-(methylamino)-3H-xanthen-3-ylidene)methanaminium; DOI: 10.1002/anie.201511018 |
| Halo-510R | (Z)-N-(9-(2-carboxy-5-((2-(2-((6-chlorohexyl)oxy) ethoxy)ethyl)carbamoyl)phenyl)-2,7-difluoro-6-((2,2,2-trifluoroethyl)amino)-3H-xanthen-3-ylidene)-2,2,2-trifluoroethan-1-aminium; DOI: 10.1039/c7sc05334g |
| Halo-JF669 | 1-(7-(azetidin-1-yl)-10-(2-carboxy-5-((2-(2-((6-chlorohexyl)oxy)ethoxy)ethyl)thio)-3,4,6-trifluorophenyl)-5,5-dimethyldibenzo[b,e]silin-3(5H)-ylidene) azetidin-1-ium; DOI: 10.1021/acscentsci.7b00247 |
| Halo-Cy3 | 1-(6-((2-(2-((6-chlorohexyl)oxy) ethoxy)ethyl)amino)-6-oxohexyl)-2-((E)-3-((E)-3,3-dimethylindolin-2-ylidene)prop-1-en-1-yl)-3,3-dimethyl-3H-indol-1-ium; Lumiprobe Corp. #11090 (carboxylic acid precursor) |
| Halo-Cy5 | 1-(6-((2-(2-((6-chlorohexyl)oxy) ethoxy)ethyl)amino)-6-oxohexyl)-2-((1E,3E)-5-((E)-3,3-dimethylindolin-2-ylidene)penta-1,3-dien-1-yl)-3,3-dimethyl-3H-indol-1-ium; Lumiprobe Corp. #13090 (carboxylic acid precursor) |
| Halo Fluorescein (diAc) | 6-((2-(2-((6-chlorohexyl)oxy)ethoxy)ethyl) carbamoyl)-3-oxo-3H-spiro [isobenzofuran-1, 9'-xanthene]-3', '-diyl diacetate; Promega Corp. #G8272 (double acetylated) |
| Halo-OregonGreen (diAc) | 6-((2-(2-((6-chlorohexyl)oxy) ethoxy)ethyl)carbamoyl)-2',7'-difluoro-3-oxo-3H-spiro[iso-benzofuran-1,9'-xanthene]-3',6'-diyl diacetate; Promega Corp. #G2801 (double acetylated) |
| Halo-Fluorescein | 4-((2-(2-((6-chlorohexyl)oxy) ethoxy)ethyl)carbamoyl)-2-(6-hydroxy-3-oxo-3H-xanthen-9-yl)benzoic acid Promega Corp. #G8272 hydrolysis prodct |
| Halo-OregonGreen | 4-((2-(2-((6-chlorohexyl)oxy) ethoxy)ethyl)carbamoyl)-2-(2,7-difluoro-6-hydroxy-3-oxo-3H-xanthen-9-yl)benzoic acid Promega Corp. #G2801 hydrolysis product |
| Halo-Alexa488 | 6-amino-9-(2-carboxy-5-((2-(2-((6-chlorohexyl)oxy) ethoxy)ethyl)carbamoyl)phenyl)-3-iminio-3H-xanthene-4,5-disulfonate Promega Corp. #G1001 |
| Halo-Abberior580LIVE JF503 aka JF505 | NA Abberior GmbH #1-0001-014-5 (carboxylic acid precursor) 4-((2-(2-((6-chlorohexyl)oxy) ethoxy)ethyl)carbamoyl)-2-(6-(3,3-difluoroazetidin-1-yl)-3-oxo-3H-xanthen-9-yl) benzoic acid; DOI: 10zz.1038/nmeth.4403 |

Wherever alternatives for single separable features, it is to be understood that such alternatives may be combined freely to form discrete embodiments of the invention disclosed herein.

The invention is further illustrated by the following examples and figures, from which further embodiments and advantages can be drawn. These examples are meant to illustrate the invention but not to limit its scope.

BRIEF DESCRIPTION OF THE FIGURES

FIG. 10 $EC_{50}$ of second generation CaProLa constructs: (A) The labelling reactions of CaProLa 2.1-2.3 were obtained via FP at free calcium concentrations ranging from 10 nM to 3.2 μM. Curves were fitted to a second order rate equation and initial reaction rates were calculated from the fits. (B) Initial rates were plotted against the free calcium concentrations and a four-parameter logistic model was fitted to the data to determine the $EC_{50}$ for each construct. All experiments were performed in triplicate, error bars and uncertainties represent standard deviations.

BRIEF DESCRIPTION OF THE DESCRIBED SEQUENCES

The nucleic and/or amino acid sequences provided herewith are shown using standard letter abbreviations for nucleotide bases, and three letter code for amino acids, as defined in 37 C.F.R. 1.822. Only one strand of each nucleic acid sequence is shown, but the complementary strand is understood as included by any reference to the displayed strand. The Sequence Listing is submitted as an ASCII text file named 95083_381_2_ST25.txt, created Apr. 3, 2022, about 53 KB, which is incorporated by reference herein.

EXAMPLES

Example 1: Design of a Calcium Signal Integrator Based on Split Halo Tag™ 7

HaloTag™ 7 (PDB 6Y7A) is a self-labelling protein derived from the haloalkane dehydrogenase DhaA of *Rhodococcus rhodochrous* that specifically reacts with and covalently binds a synthetic chloroalkane ligand. A split system was generated, wherein the original termini of HaloTag™ 7 were connected via a (GGS/T)$_5$ linker and a peptide was excised from the Halo Tag™ 7 protein in between the CP sites of cpHalo141-145 (cpHaloTag™ 7 with new termini at position 141 and 145) and cpHalo 156-154. The part between those positions was excised to generate a split consisting of cpHalo 156-141 and the short 9mer peptide from position 145 to 153/154.

Since the cpHaloΔ9mer—9merPeptide couple showed promising preliminary results, a first version of a calcium integrator was designed by fusing them via GGS linkers to an M13 peptide and a calmodulin protein, respectively. At elevated calcium concentration, calmodulin binds up to four calcium ions resulting in a large conformational change that strongly increases its affinity to the M13 recognition peptide. The resulting association of calmodulin and M13 leads to the complementation of cpHaloΔ9mer by the 9mer peptide. Upon complementation, the enzyme regains its activity and is able to react with fluorescent HaloTag™ substrates, leaving a permanent mark and thus integrating the signal.

Example 2: Affinity Between cpHaloΔ9Mer and the 9Mer Peptide

Isothermal Titration Calorimetry

The affinity between cpHalo_9mer and the 9mer peptide was measured via a label free approach using isothermal titration calorimetry (ITC).

Figure 1:
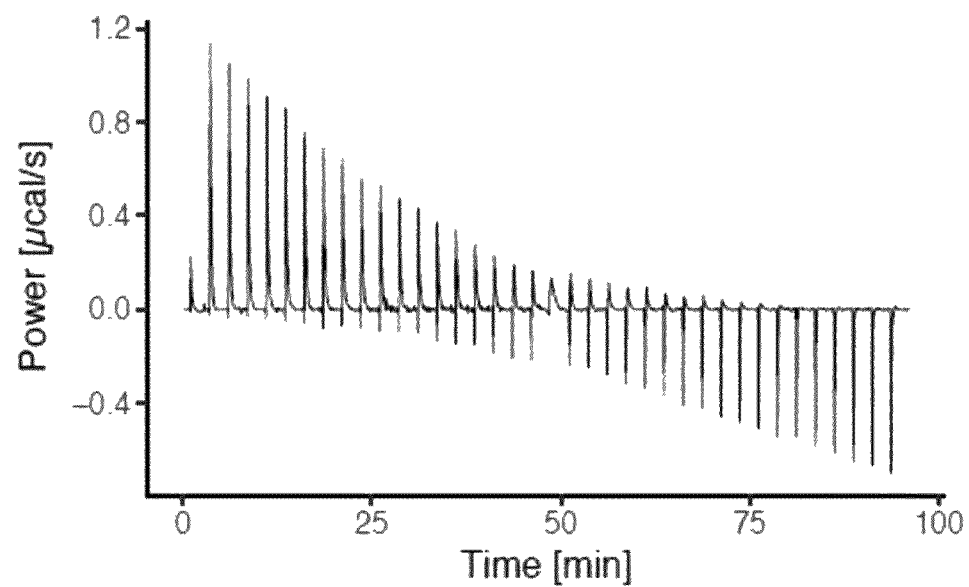
FIG. 1 ITC assay to measure the affinity between cpHaloΔ9mer and the 9mer peptide: Representative measurement of 9mer peptide (30 mM) titrated into cpHaloΔ9mer (0.6 mM) solution. Upper row: Raw ITC data after baseline subtraction of two concatenated measurements. Lower row: ΔH plotted against molar ratio of 9mer to cpHaloΔ9mer (points) and fit to one site binding model (line). Heat of dilution of the peptide was subtracted prior to the analysis. $K_d$ was calculated from three independent measurements, error represents standard deviation.
Figure 1:
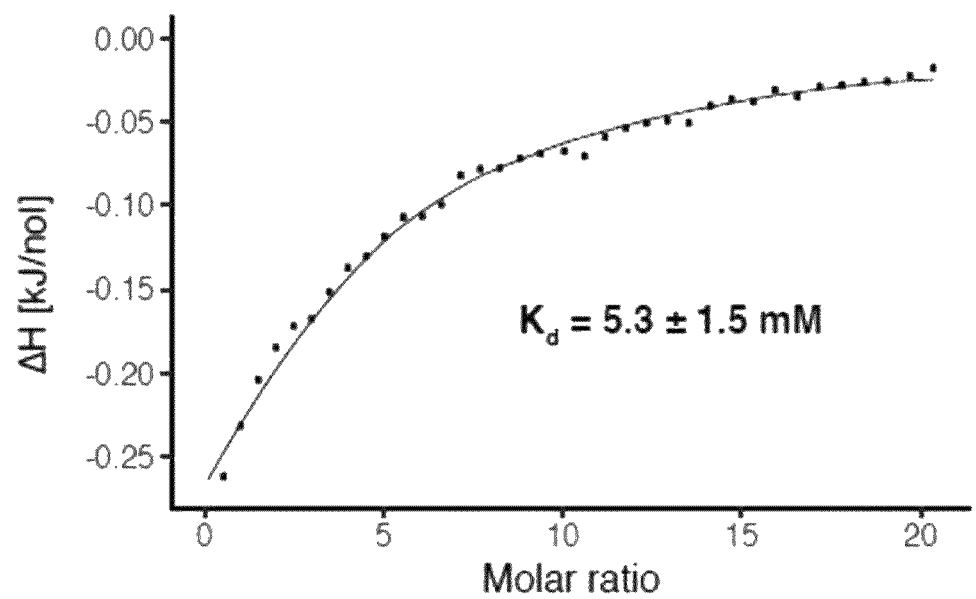

The 9mer peptide is soluble at ~30 mM in activity buffer (HEPES 50 mM pH 7.3-NaCl 50 mM) and forms a gel at higher concentrations in a strongly temperature dependent manner. This maximal concentration of peptide was titrated against a 0.6 mM cpHaloΔ9mer (FIG. 1). To verify the unusually high $K_d$, the experiment was repeated three times with different batches of cpHaloΔ9mer. A $K_d$ value of 5.3+/−1.5 mM could be calculated from the three independent measurements.

Example 3: Affinities of Fluorescent Ligands to HaloTag™ 7 and cpHaloΔ9Mer

The inventors decided to perform the experiment with some representative fluorescent HaloTag™ substrates. An exchange of the aspartate106 residue in the active site by an alanine, removes the nucleophile responsible for the self labeling reaction and eliminates the catalytic activity of the protein. Catalytically dead mutants of HaloTag™ 7 (HaloTag™ 7D106A) and cpHaloΔ9mer (cpHalo_9merD106A) were generated to measure substrate affinities without displacement of the equilibrium by the enzymatic reaction.

Figure 2:
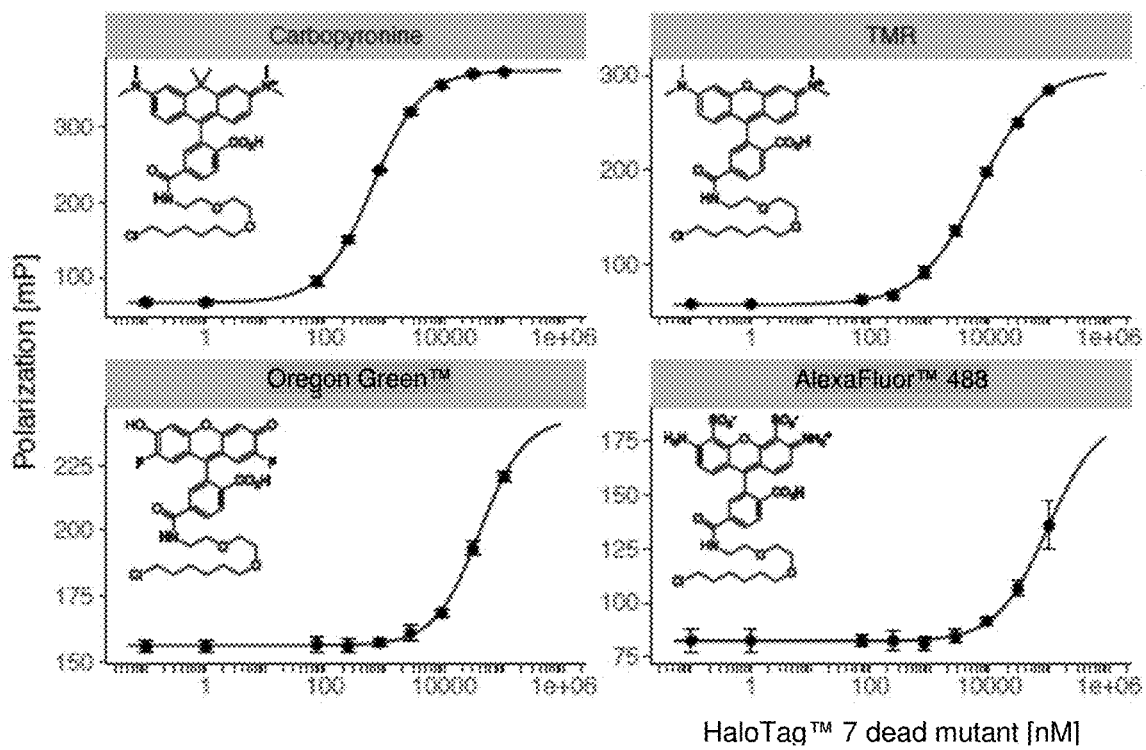
FIG. 2 Affinities of fluorescent Halo Tag™ ligands to HaloTag7D106A: The catalytically dead variant HaloTag7D106A was titrated against 5 different fluorescent HaloTag™ ligands at 25 nM in an FP binding assay (Halo-carbopyronine, Halo-TMR, Halo-TMR-azetidine, Halo-Oregon Green™, Halo Alexa Fluor™ 488). Structures of the fluorescent ligands are shown in each graph. Data were fitted to a one-site binding model and derived $K_d$ values are summarized in the table. Data points at 0.1 nM and 1 nM correspond to values without any protein added, but were placed at low concentrations to appear on the logarithmic scale. All experiments were performed in triplicates, error bars and annotated uncertainties represent standard deviations.
Figure 2:
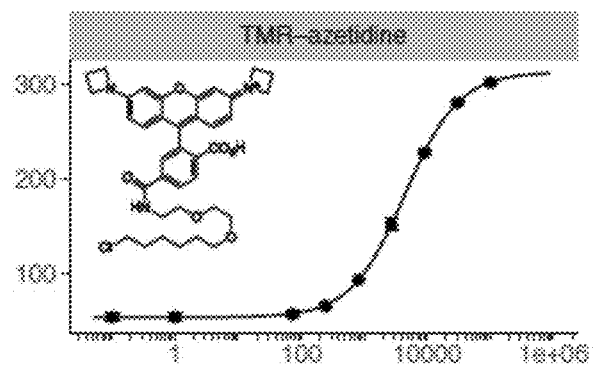
Figure 3:
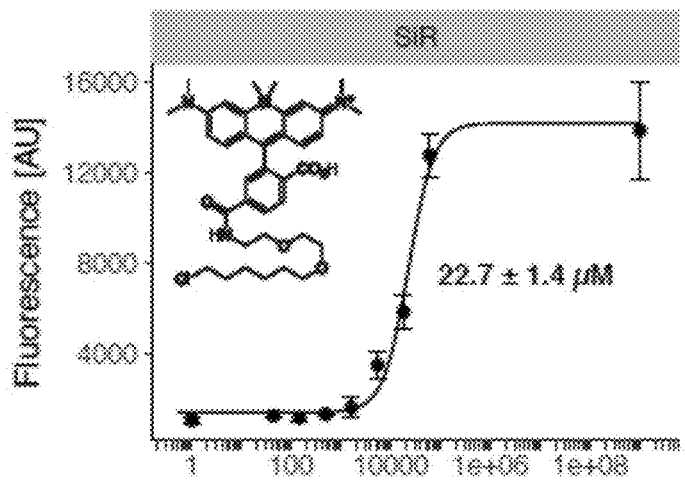
FIG. 3 Affinities of fluorogenic HaloTag™ ligands to HaloTag7D106A: The catalytically dead variant HaloTag7D106A was titrated against 3 different fluorogenic HaloTag™ ligands at 25 nM in a fluorescence intensity based binding assay (Halo-Siliconrhodamine, Halo-Janelia Fluor 646 and Halo-Janelia Fluor 635). Structures of the fluorogenic ligands are shown in each graph. Data were fitted to a one-site binding model and derived $K_d$ values are shown in the graph. Due to the low affinity of the fluorogenic substrates, data points at 109 nM were extrapolated based on fully labelled Halo Tag™ 7 (resembling complete binding) to improve fitting. Data points at 1 nM correspond to values without any protein added, but were placed at low concentrations to appear on the logarithmic scale. All experiments were performed in triplicates, error bars and annotated uncertainties represent standard deviations.
Figure 3:
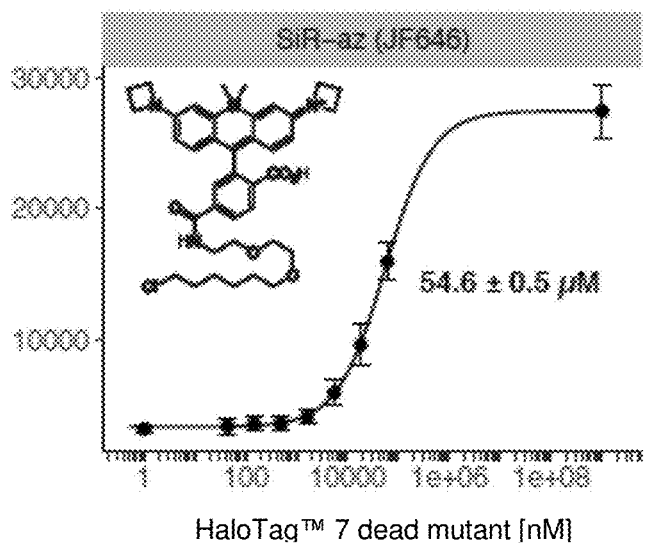
Figure 3:
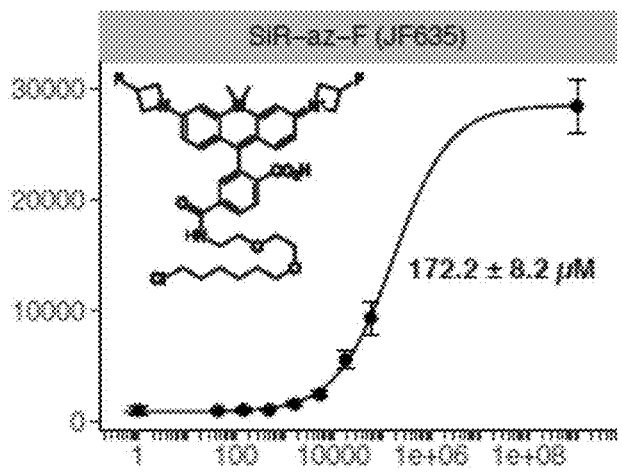
Figure 4:
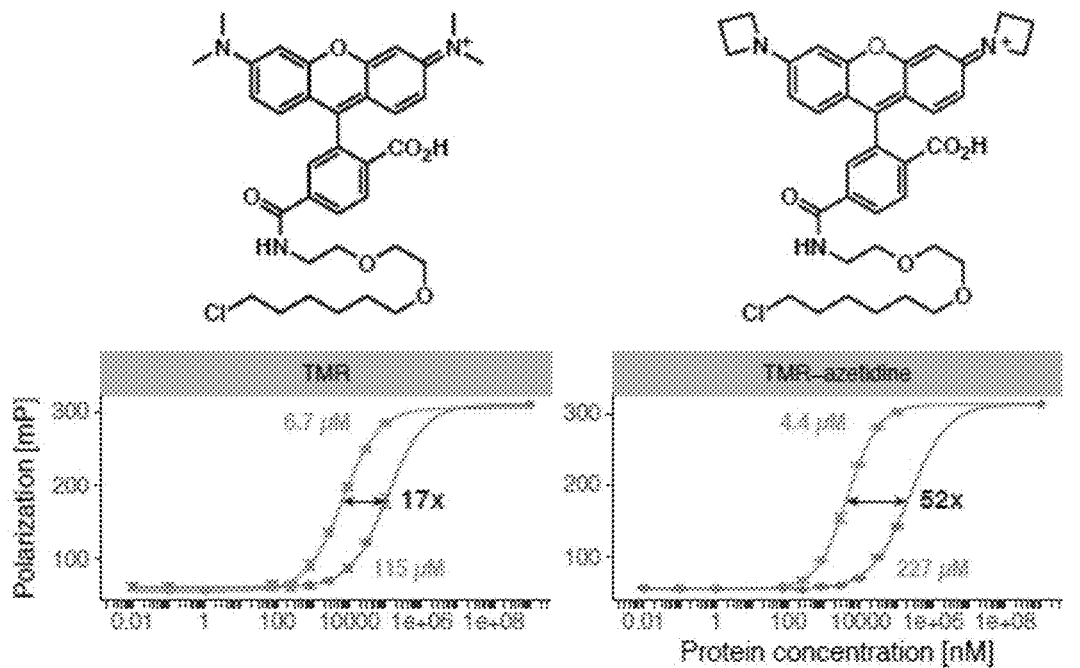
FIG. 4 Comparison of HaloTag™ 7D106A and cpHaloΔ9merD106A fluorescent substrate binding: The catalytically dead variant Halo Tag™ 7Δ9merD106A (blue) was titrated against 3 different fluorescent Halo Tag™ ligands at 25 nM in an FP binding assay (Halo-TMR, Halo-TMR-azetidine and Halo-carbopyronine). Structures of the respective fluorescent ligands are shown above each graph. Data were fitted to a one-site binding model and derived $K_d$ values are shown in the graphs. Data points at 0.01 nM and 0.1 nM correspond to values without any protein added, but were placed at low concentrations to appear on the logarithmic scale. Data were compared to HaloTag™ 7D106A binding of the same fluorophores (red). Differences in binding affinity are indicated by the relative fold change of $K_d$ values. All experiments were performed in triplicate, error bars represent standard deviations.
Figure 4:
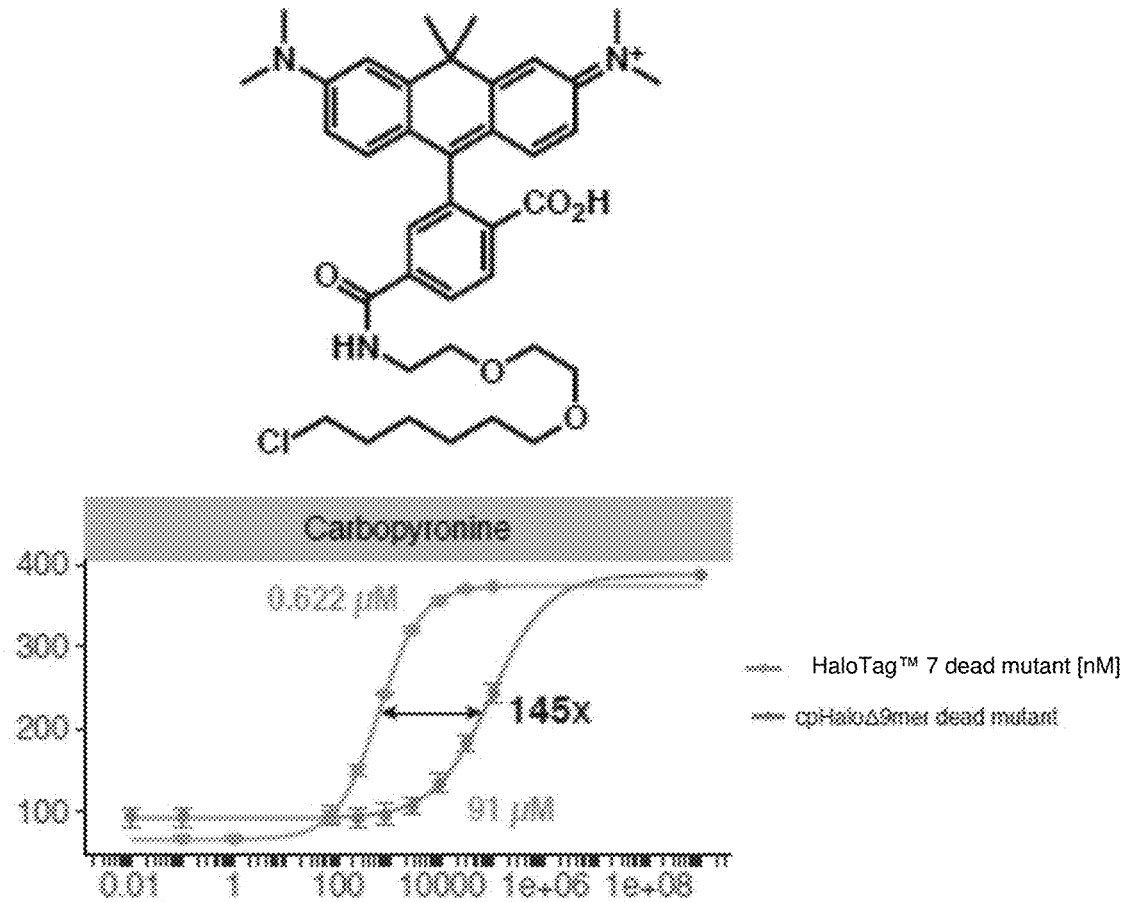

Affinities for the different fluorescent substrates towards HaloTag™ 7D106A were determined in an FP binding assay (FIG. 2), while affinities of fluorogenic silcon-rhodamine derived substrates were measured by a fluorescence intensity based binding assay (FIG. 3), since binding of the fluorogenic ligands by HaloTag™ 7 engenders a strong increase of fluorescence. In both cases Halo Tag7D106A concentrations ranging from 0 μM to 100 μM were titrated against 25 nM of dye. HaloTag7D106A binds its ligands with affinities ranging from 622 +/−3.7 nM for Halo carbopyronine (Halo-CPY) to 172.2+/−8.2 μM for Halo-Janelia Fluor 635 (table 1). The observed affinities are in agreement with labelling kinetics recorded with different substrates (data not shown). In general, fluorogenic substrates have lower affinities to HaloTag7D106A than non-fluorogenic substrates, except for Halo-Alexa Fluor™ 488 that features an affinity in the same range. Additionally, within the Silicon rhodamine derivatives the presence of an azetidine or 3-fluoroazetidine moiety has an influence on the binding affinity which is more pronounced compared to the rhodamine structure. Affinities of fluorescent HaloTag™ ligands presenting the best affinities for HaloTag™ 7 were tested with cpHaloΔ9merD106A in an FP binding assay and results were compared to the measurements with HaloTag7D106A (FIG. 4, table 1).

Example 4: Background Labelling of cpHaloΔ9Mer

A well performing protein complementation assay requires a low background. The inventors thus measured the extent of background labelling of cpHaloΔ9mer with different fluorophores (Halo-TMR, Halo-CPY and Halo-SiR). Therefore, cpHaloΔ9mer was incubated with an excess of the different fluorescent ligands.

Figure 5:
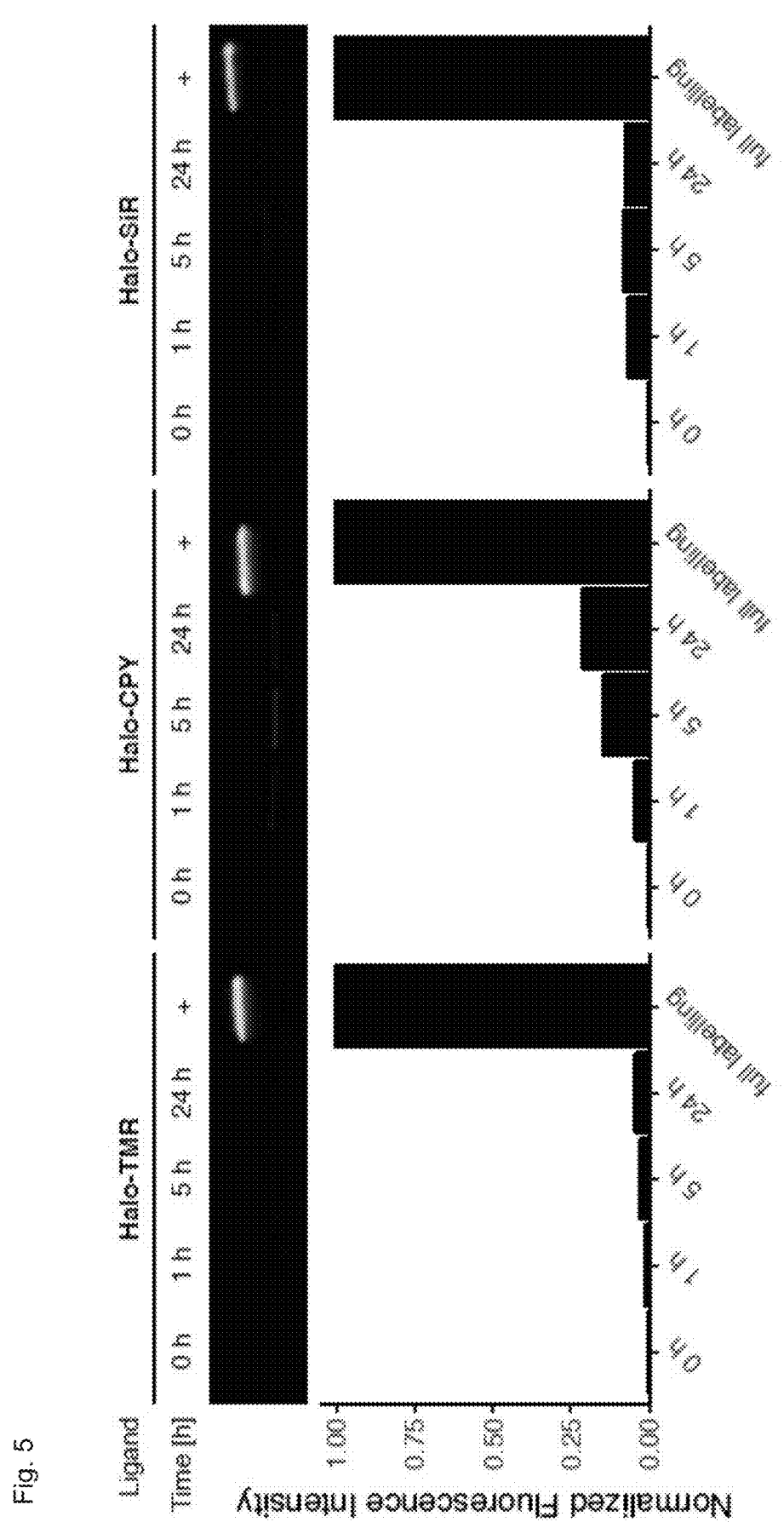
FIG. 5 Background labeling of cpHaloΔ9mer: Background labeling of cpHaloΔ9mer (1 μM) in presence of 2 μM fluorescent ligands (at 37° C.) was determined via in gel fluorescence measurements. Samples were denatured and analysed via SDS-PAGE followed by in gel fluorescence scanning (top; gel is represented in false colors to highlight dim bands). Intensities were normalized to Halo Tag™ 7 labeled with the respective fluorophore (bottom).

The labelling efficiency at 37° C. and at different time points was determined via in gel fluorescence measurements (FIG. 5). Very low background labelling was observed for Halo-TMR and Halo-SiR. Halo-CPY showed slightly stronger background labelling, eventually reaching 20% after 24 h. These findings are in accordance to fluorescent ligand affinities (FIG. 4). Indeed, Halo-CPY has the highest affinity to cpHaloΔ9mer and already presents some affinity for the ligand at 2 µM engendering a labelling which still remains marginal considering the experimental setup.

Example 5: Characterization and Optimization of a Calcium Signal Integrator Based on Split HaloTag™ 7: Linker Optimization The initial design of a calcium integrator consisted of the fusion of cpHaloΔ9mer to an M13 peptide and the 9mer peptide to calmodulin. Both fusion partners were taken from the calcium sensing domain of GCaMP6f. Kinetics by fluorescence polarization using Halo-TMR as a substrate revealed no background in the absence of calcium and a second order rate constant for the labelling of $6.7+/-0.5*10^3$ $s^{-1}M^{-1}$ in presence of calcium.

Figure 6:
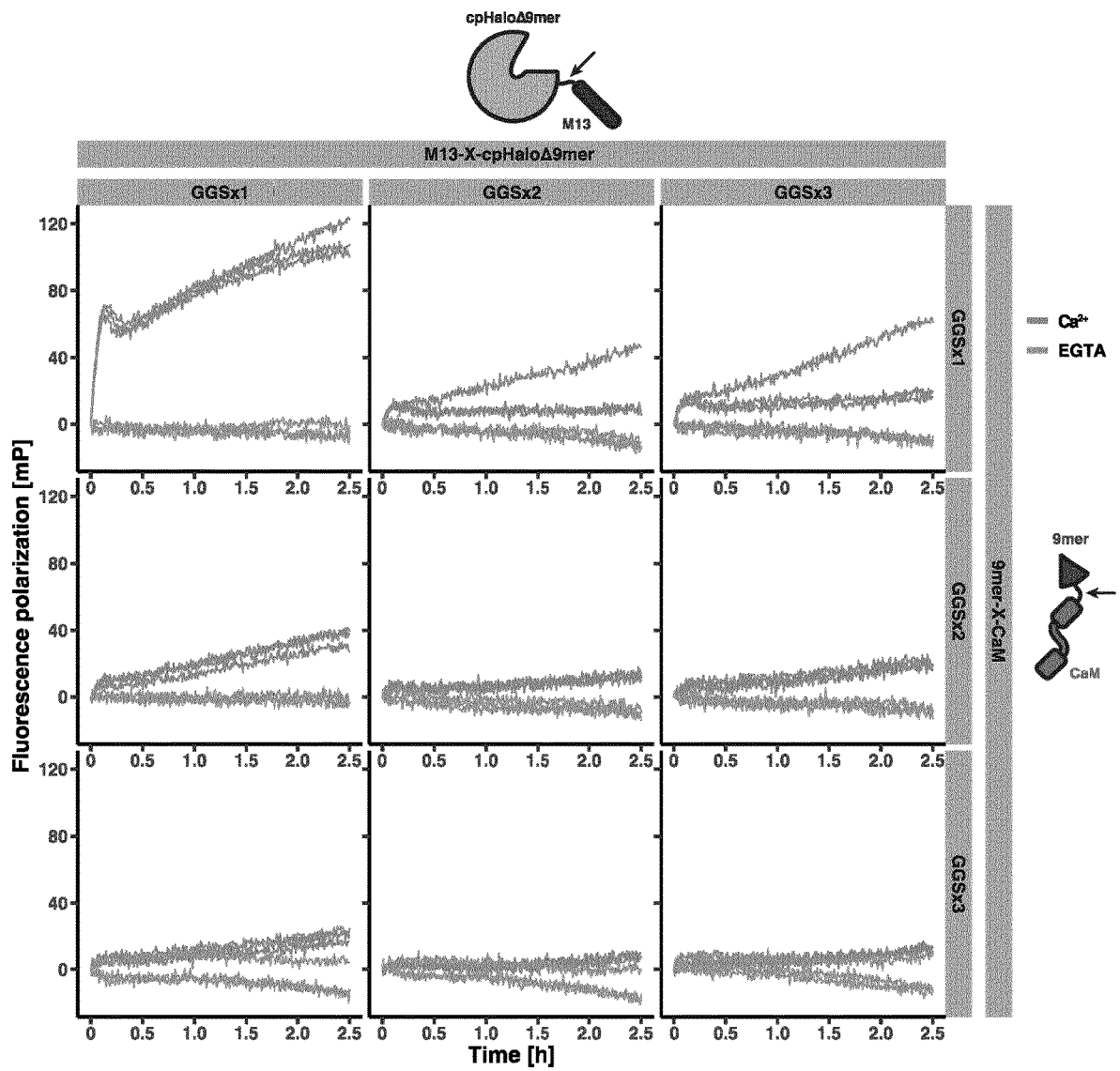
FIG. 6 M13—cpHaloΔ9mer and 9mer—CaM linker length optimization: All combinations of split integrators composed of M13—(GGS)$_{1-3}$—cpHaloΔ9mer and 9mer—(GGS)$_{1-3}$—CaM were tested in an FP kinetic assay in the presence of calcium or EGTA.

Optimal linkers should assist the placement of the 9mer peptide at a good distance and proper orientation to complement cpHaloΔ9mer. Therefore, three variants of each part of the split were produced with varying linker lengths ($(GGS)_{1-3}$). These constructs allowed to screen all combinations of linker lengths in order to work with the optimal combination. For both, the M13-cpHaloΔ9mer linker and the 9mer-calmodulin linker, it was observed that increment of linker length leads to a significant loss in calcium induced activity. Interestingly, the initially chosen single GGS linkers clearly performed best since they showed the fastest labelling kinetic with calcium and no detectable background after 2.5 h (FIG. 6).

Example 6: Design and Testing of an Intramolecular Calcium Integrator Based on Split Halo Tag™ 7

Figure 7A:
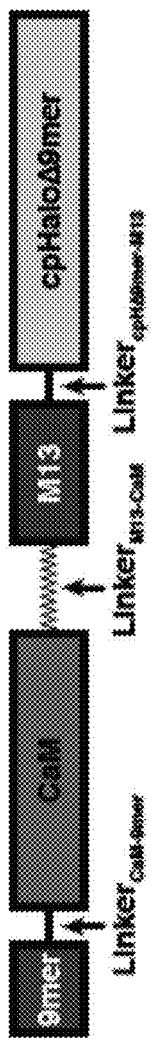
FIG. 7 General concept of an intramolecular calcium integrator based on split Halo Tag™ 7 (CaProLa): (A): Schematic representation (N to C-terminus) of the primary structure of the intramolecular calcium integrator CaProLa. (B): The two parts of the split calcium integrator were combined by connecting CaM and M13 with a linker domain to create a single chain sensor. (C): Modelled structure of CaProLa: crystal structures of HaloTag™ 7 (PDB 4KAF) and the CaM—M13 domains of GCaMP3 (PDB 3SG3) were modified and arranged to resemble the CaProLa architecture.
Figure 7B:
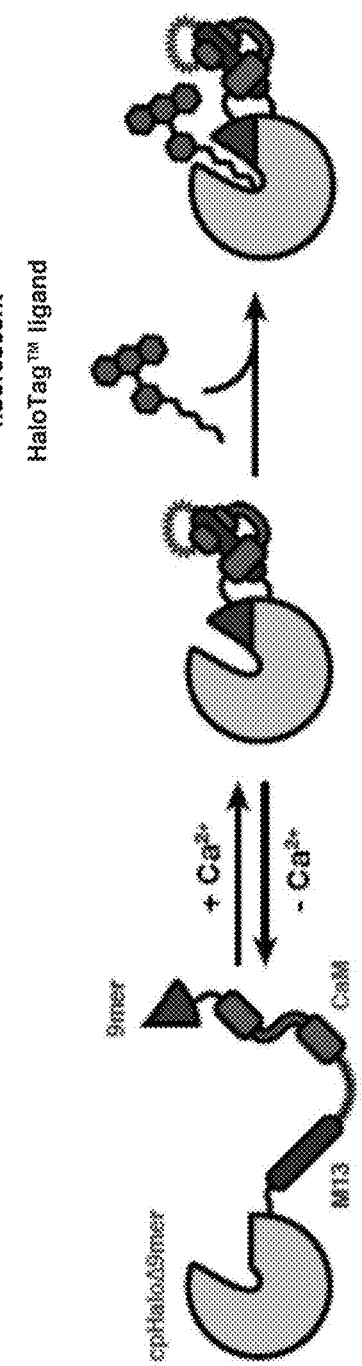
Figure 7C:
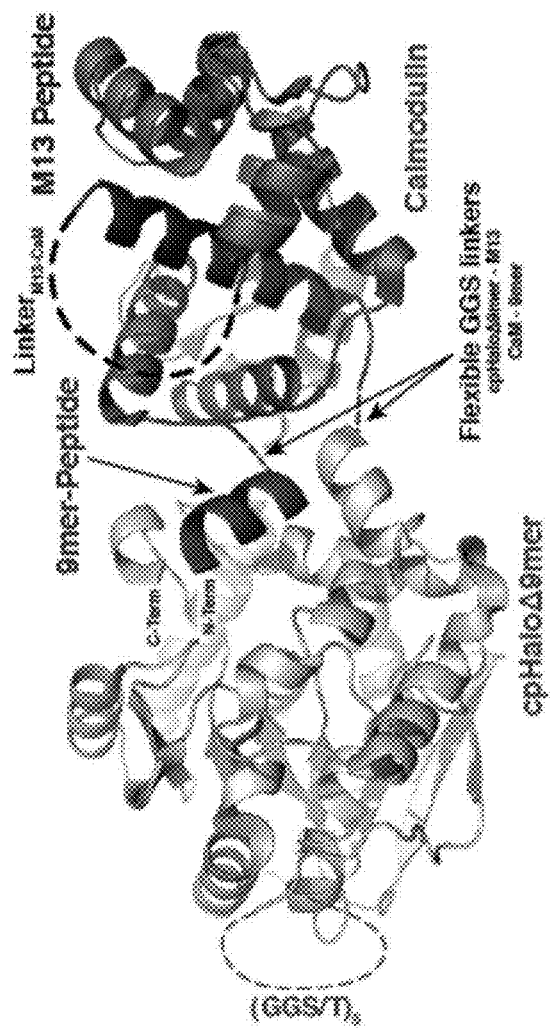

The inventors designed a simplified intramolecular calcium integrator that they refer to as "CaProLa" (calcium dependent protein labeling) by fusing the two integrator compartments between calmodulin and M13 using different linker domains (FIG. 7). The following calmodulin—M13 linkers were tested for this first generation of CaProLa constructs:
a flexible GGTGGS (SEQ ID NO 026) linker-(CaProLa 1.1)
a partly flexible, partly rigid Pro15-$(GGS)_2$-$Pro_{15}$ linker—(CaProLa 1.2)·
a rigid Pro30 linker—(CaProLa 1.3)·
a SNAP-tag™ domain flanked by Pro15 linkers—(CaProLa 1.4)

Figure 8:
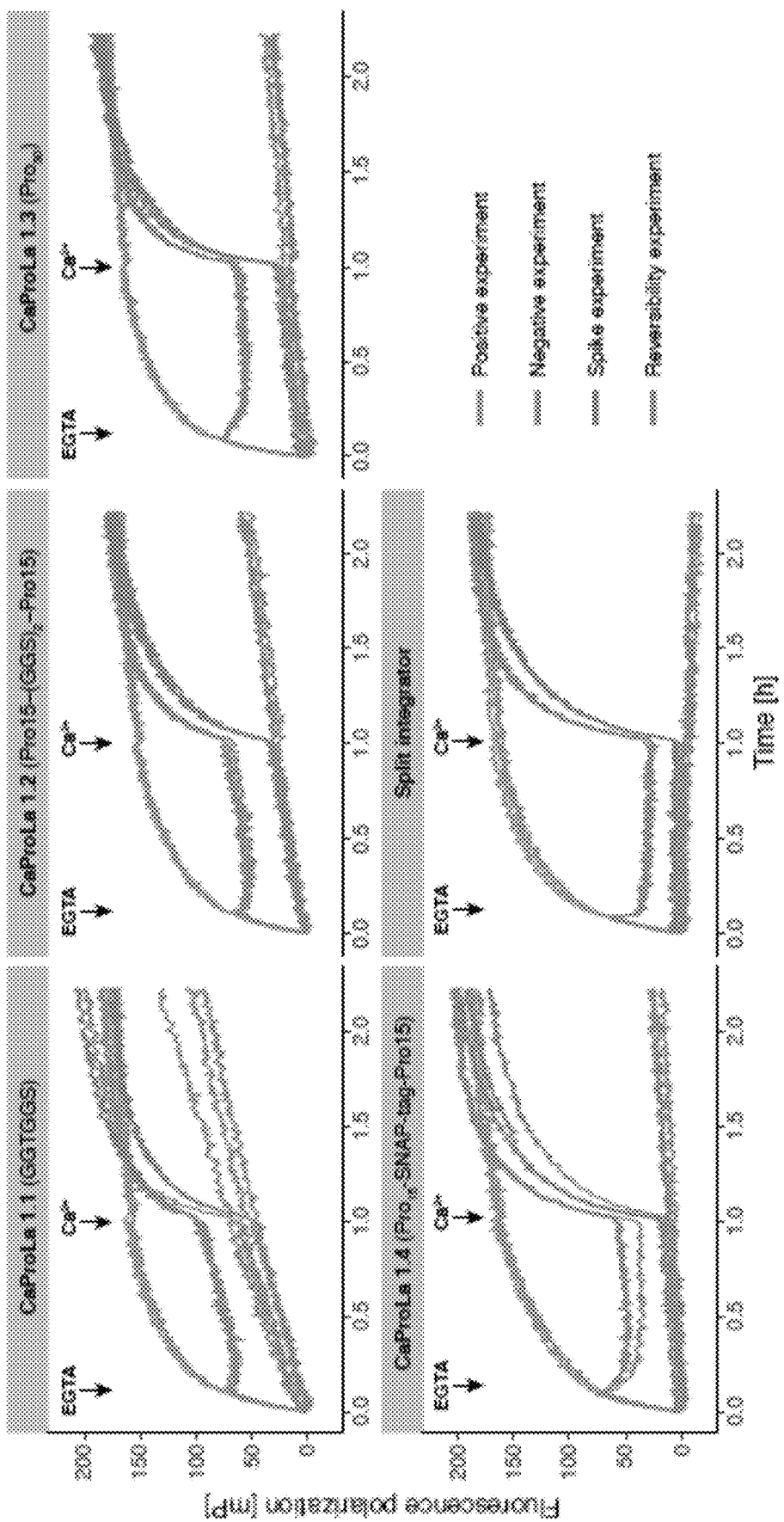
FIG. 8 Performance of CaProLa constructs with different M13—CaM linkers: FP kinetics of different CaProLa constructs and the split integrator under four conditions: in the presence of calcium (red), in the absence of calcium (purple), in the absence of calcium but spiked with calcium after 1 h (cyan), in the presence of calcium, followed by an EGTA spike to stop the reaction, followed by a calcium spike to restart the reaction (green). Small arrows indicate the EGTA and calcium spikes. Curves in the presence of calcium (red) were fitted to a second order reaction rate equation to determine the rate constants. All experiments were performed in triplicates. GGTGGS: SEQ ID NO 027.

Each construct as well as the split system were tested in an FP kinetic assay using Halo-TMR as a substrate in four different conditions (FIG. 8):
in the presence of calcium to determine the labelling kinetic and rate constant (positive experiment)
in the absence of calcium, ensured by addition of EGTA to assay background labelling (negative experiment)
in the absence of calcium but spiked with calcium after 1 h to show activation after prolonged incubation with the substrate (spike experiment)
in the presence of calcium, followed by an EGTA spike to stop the reaction, then followed by a calcium spike to restart the reaction in order to show reversibility of the sensor (reversibility experiment)

All tested variants showed similar rate constants ranging between $3*10^3$ $s^{-1}M^{-1}$ and $5*10^3$ $s^{-1}M^{-1}$ in the presence of calcium. Furthermore, induction via calcium spiking after one hour and the reversibility experiments were successful, suggesting that once the 9mer peptide has bound to the cpHaloΔ9mer structure, it is able to unbind (even in an intramolecular system) offering a good dynamic.

However, differences can be seen in the background labelling of the sensors. The split integrator showed no detectable background over 2 h, while the CaProLa constructs exhibited background labelling of varying extent, correlating with the M13-CaM linker rigidity. The least background was observed with the $Pro_{30}$ linker and the $Pro_{15}$-SNAP-$Pro_{15}$ domain.

Example 7: Calcium Responsivity of the Different CaProLa Constructs

The calmodulin-M13 pair chosen for the first design of CaProLa was taken from GCaMP6f. Depending on the structural context, the responsivity of the pair toward calcium can vary. The calmodulin moiety binds up to four calcium atoms with a very complex allosteric behaviour. However, if incorporated in a sensor, a simple titration of the sensor activity to the free calcium concentration leads to the identification of an EC50 that represents the response range of the sensor.

Figures 9A, 9B:
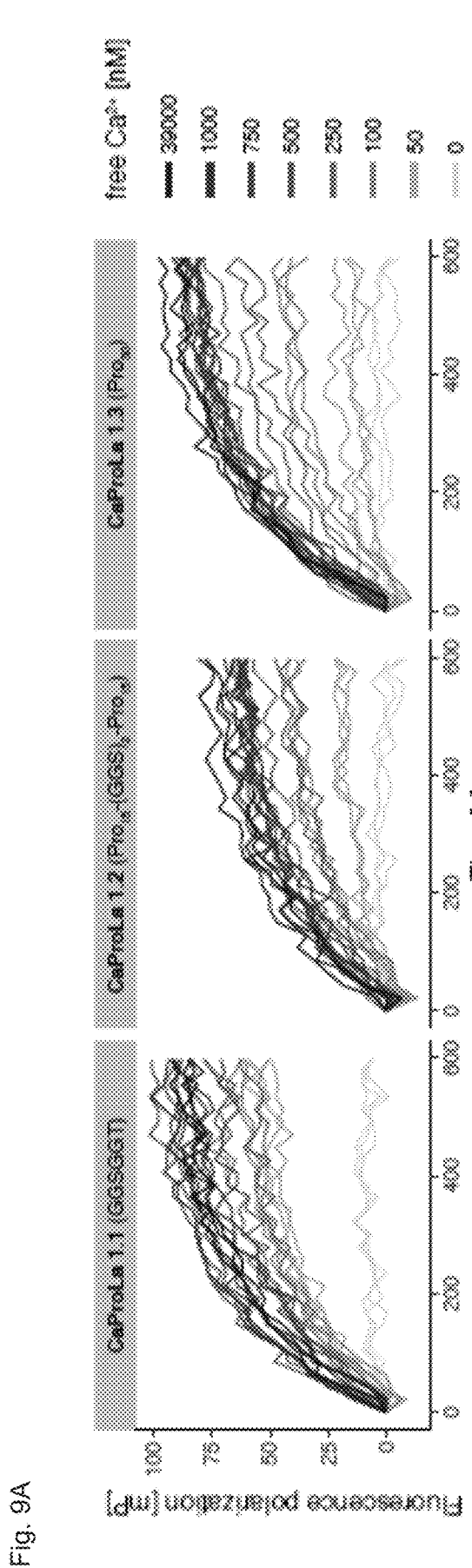
FIG. 9 Calcium responsivity of CaProLa constructs with different M13—CaM linkers: (A) The labeling reaction of CaProLa constructs was observed via FP at free calcium concentrations ranging from 0 nM to 39 μM. Curves were fitted to a second order rate equation and initial reaction rates were calculated from the fits. (B) Initial rates were plotted against the free calcium concentrations (0 nM calcium was adjusted to 0.01 nM to appear on the logarithmic scale) and a four-parameter logistic model was fitted to the data to determine the EC50 for each construct. These experiments relate to the intra-molecular ΔcpHalo linker between effector part 1 and effector part 2—not the intermodular linkers between sensor-effector. All experiments were performed in triplicates, error bars and uncertainties represent standard deviations. GGSGGT: SEQ ID NO 028.

The calcium dependence of CaProLa constructs with different M13-CaM linkers was characterized by measuring the calcium dependent EC50. Therefore, labelling at different calcium concentrations was monitored in an FP kinetic assay. To achieve defined calcium concentrations in the nanomolar range, a $K_2$EGTA-CaEGTA buffered system was used. Initial reaction rates were determined to calculate the calcium dependent EC50 (FIG. 9). Measured EC50 values are in the low nanomolar range (19 nM to 146 nM) and depend on the rigidity of the M13-CaM linker. Increased rigidity of the linker results in a higher $EC_{50}$. For comparison, the GCaMP6f with the same calmodulin-M13 couple presents an $EC_{50}$ of 375+/−14 nM.

Example 8: Tuning the Calcium Responsivity of CaProLa Constructs

The resting calcium concentration in neurons is reported to be 50 nM to 100 nM. As a consequence, the first generation of CaProLa was considered to be too sensitive towards calcium to be functional in neurons. Thus, a second generation of CaProLa was designed with the aim to generate different constructs exhibiting different calcium responsivities, especially with increased $EC_{50}$.

The calmodulin-M13 couple is highly studied and a large number of mutations were reported and used in sensors to modify the calcium responsivity. The inventors thus decided to base their design on yet unpublished versions of the calcium integrator CAMPARI2 deposited on Addgene (Schreiter, E. Addgene plasmids #101061, #101062 and #101064). These CAMPARI2 variants are annotated with $EC_{50}$ values ranging from 110 nM to 825 nM and were designed for a similar application.

Three of the modified M13 peptides were implemented in a second generation of CaProLa constructs (CaProLa 2.1-2.3). These constructs are all based on CaProLa 1.3 ($Pro_{30}$ M13-CaM linker) due to its low background. $EC_{50}$ values for the new CaProLa constructs were determined as described above (FIG. 10).

$EC_{50}$ values of CaProLa 2.1-2.3 are comparable to the values annotated for CAMPARI2 (table 2). CaProLa 2.1 and 2.2 both feature an $EC_{50}$ significantly higher than the version 1.4 which might be appropriate for the integration of neuronal calcium waves (500 nM-10 µM).

Figure 11:
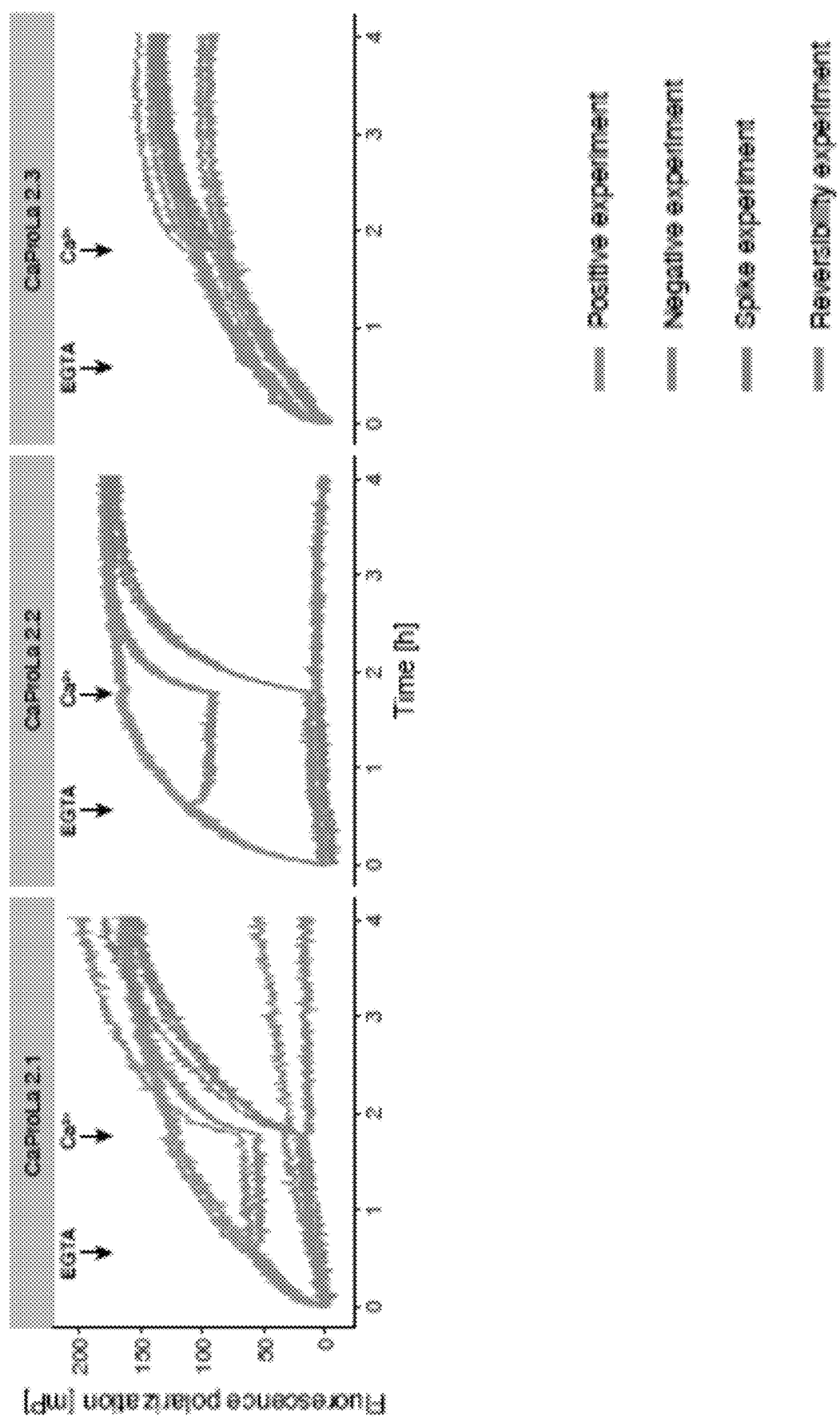
FIG. 11 Performance of second generation CaProLa constructs: A fluorescence polarization kinetic assays with Halo-TMR of CaProLa 2.1-2.3 were performed under four conditions: in the presence of calcium (red), in the absence of calcium (purple), in the absence of calcium but spiked with calcium after 1 h (cyan), in the presence of calcium, followed by an EGTA spike to stop the reaction, followed by a calcium spike (green). Small arrows indicate the EGTA and calcium spikes. Curves in the presence of calcium (red) were fitted to a second order reaction rate equation to determine the rate constants. All experiments were performed in triplicate.

Similar to the first generation, all new CaProLa constructs were tested regarding calcium induced kinetics, reversibility and background labelling in an FP kinetic experiment (FIG. 11). From the three tested constructs only CaProLa 2.2 performed as expected. While being a bit slower than the first CaProLa generation (rate constant of 2.3+/−0.014*10$^3$ s$^{-1}$M$^{-1}$), no background was observed during 4 h incubation and the labelling reaction was reversible. CaProLa 2.1 and especially 2.3 suffered from slightly slower kinetics (ca. 1*10$^3$ s$^{-1}$M$^{-1}$) and, more importantly, higher background labelling. However, these experiments will have to be repeated to rule out any experimental mistakes since all constructs performed well in the EC$_{50}$ measurements.

Figure 12:
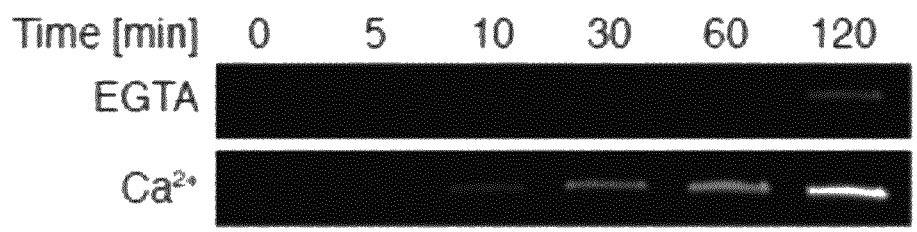
FIG. 12 Calcium dependent labelling of CaProLa 2.2 assayed via in gel kinetic: (A) CaProLa 2.2 was incubated with Halo-CPY in the presence of calcium or EGTA. Samples were taken after various incubation times and analyzed via SDS-PAGE followed by an in-gel fluorescence scan (gel is represented in false colors to highlight dim bands). (B) Fluorescence intensities were quantified and normalized to fully labelled HaloTag™ 7.
Figure 12:
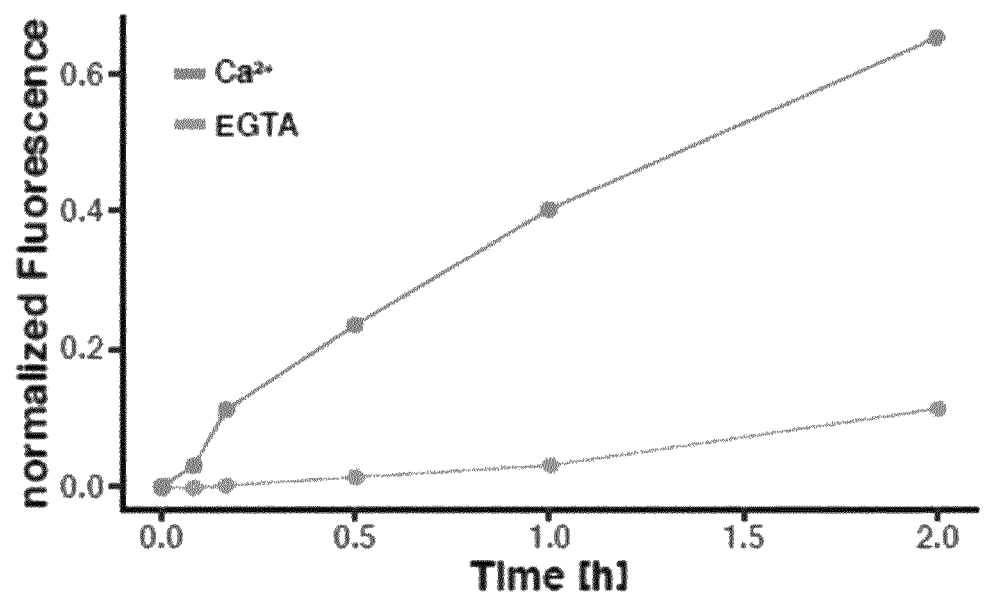

The CaProLa 2.2 construct was then tested in an in-gel fluorescence assay, to confirm the results obtained via FP assays (FIG. 12). The in-gel fluorescence assay was performed with Halo-CPY as a substrate and showed that with this fluorophore background starts to become noticeable after 2 hours. By the nature of its more direct readout (FP observing any binding), these results confirm the good functionality of CaProLa 2.2, facilitating its transfer in cellular assays.

Example 9: Fluorescence Polarization-Based Assay to Test the Performance of HaloTag™ 7 or Circular Permutations of HaloTag™ 7

Production and Purification of Proteins

Proteins (HaloTag™ 7-cpHalo variants or X-ProLa) fused to purification tags (His-tag and potentially Strep-tag™) are expressed in *Escherichia coli* BL21 (DE3)-pLysS strain and purified using classic IMAC (and potentially StrepTrap™ affinity chromatography method). After buffer exchange and concentration, if necessary (which is the case with the cpHalo variants) the N-terminal His-tag was removed by TEV cleavage and reverse IMAC purification. The buffer is exchanged to a suitable buffer (e.g. 50 mM NaCl, 50 mM HEPES, pH 7.3). If required, the proteins can be further purified by size exclusion chromatography in the same buffer.

Fluorescence Polarization Assay

Labelling kinetics are performed mixing 100 µL of protein at 400 nM with 100 µL of fluorescent HaloTag™ substrate (i.e. Halo-CPY) at 100 nM in a 96 well plate (black—not binding—flat bttom) in buffer 50 mM NaCl, 50 mM HEPES, pH 7.3, 0.5 mg/ml BSA. The increase in fluorescence polarization is recorded using a microplate reader with appropriate spectral filters/monochromators (TECAN Spark20). Since the kinetics of cpHalo variants and HaloTag™ 7 are usually extremely fast, it is mandatory to use a plate reader with internal injector to minimize the offset between mixing and the start of measurement. However, even with this equipment it might be impossible to observe the reaction that can complete in less than a second. In this case, a stopped flow setup capable of measuring fluorescence polarization with a high sampling rate is needed (e.g. BioLogic SFM). The decreased sensitivity of such instruments may require an increase in fluorescent substrate and protein concentrations (i.e. 1 µM substrate and 10 µM protein mixed 1:1).

Additionally, a fluorescence polarization time course without any protein is always recorded and subtracted from the data to account for dilution and evaporation effects. Obtained kinetic data is fitted to a second order reaction rate law (see equation below) to derive a second order rate constant (k). In order to estimate errors, the experiment should be performed at least in triplicate. To compare different variants, all assays need to be performed with the same concentrations and substrates.

$$FP = FP_{top} + \frac{FP_0 - FP_{top}}{A_0} * \frac{A_0(A_0 - B_0)e^{(A_0-B_0)kt}}{A_0 e^{(A_0-B_0)kt} - B_0} \qquad (2)$$

with:
t ::: time
FP$_0$ ::::: FP at t ::::: 0
FP$_{imp}$ ::::: upper plateau
k ::::: second order rate constant
A$_0$ ::::: starting concentration of reactant A
B$_0$ ::::: starting concentration of reactant B Generalization of the Assay for any X-ProLa Variant The fluorescence polarization assay is also used to test the performance of any X-ProLa variant. The general procedure is the same as above. However, since these constructs are often slower than HaloTag™ 7 or its CP variants, the plate reader assay may be sufficient. Also the respective metabolite/ion/small molecule that activate the sensor needs to be added in addition to the fluorescent substrate. By recording labelling kinetics with and without the metabolite, the signal over background can be measured and by titrating different metabolite concentrations, an EC$_{50}$ value of the X-ProLa can be derived (EC$_{50}$ is defined as the concentration at which the speed of labelling is half of the maximum speed of labelling).

Example 10: Protein-Protein Assaying System

Figure 13:
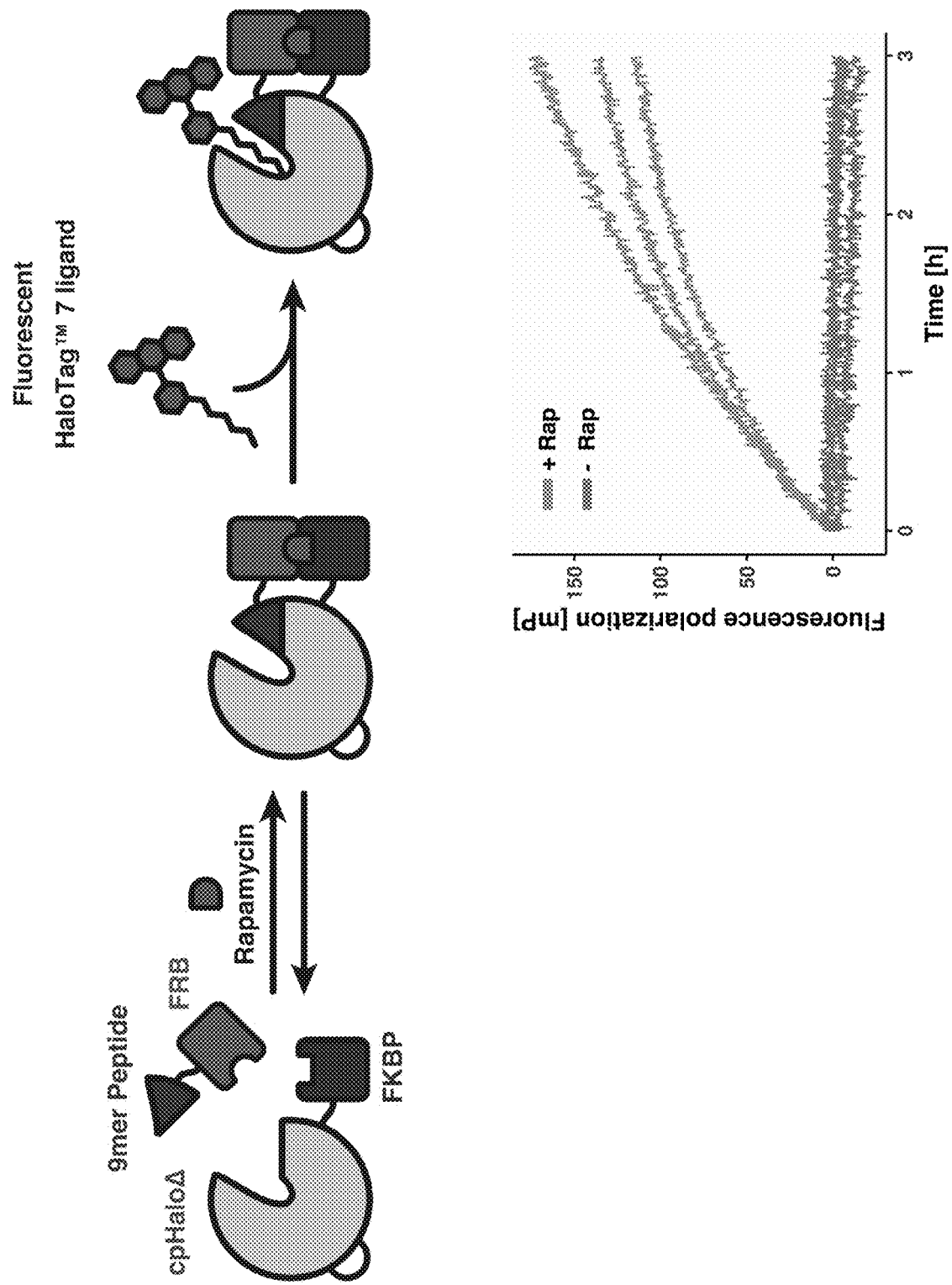
FIG. 13 Model system to test split HaloTag™ performance: Left: Scheme explaining the FKBP/FRB based model system. cpHaloΔ and the 9mer peptide are fused to FKBP and FRB, respectively, to render the split complementation and activity dependent on their rapamycin dependent interaction. Right: Labelling kinetics of the model system were followed via a fluorescence polarization assay in the presence or absence of rapamycin (Rap). Halo-TMR was used as substrate and each experiment was performed in triplicate.
Figure 14:
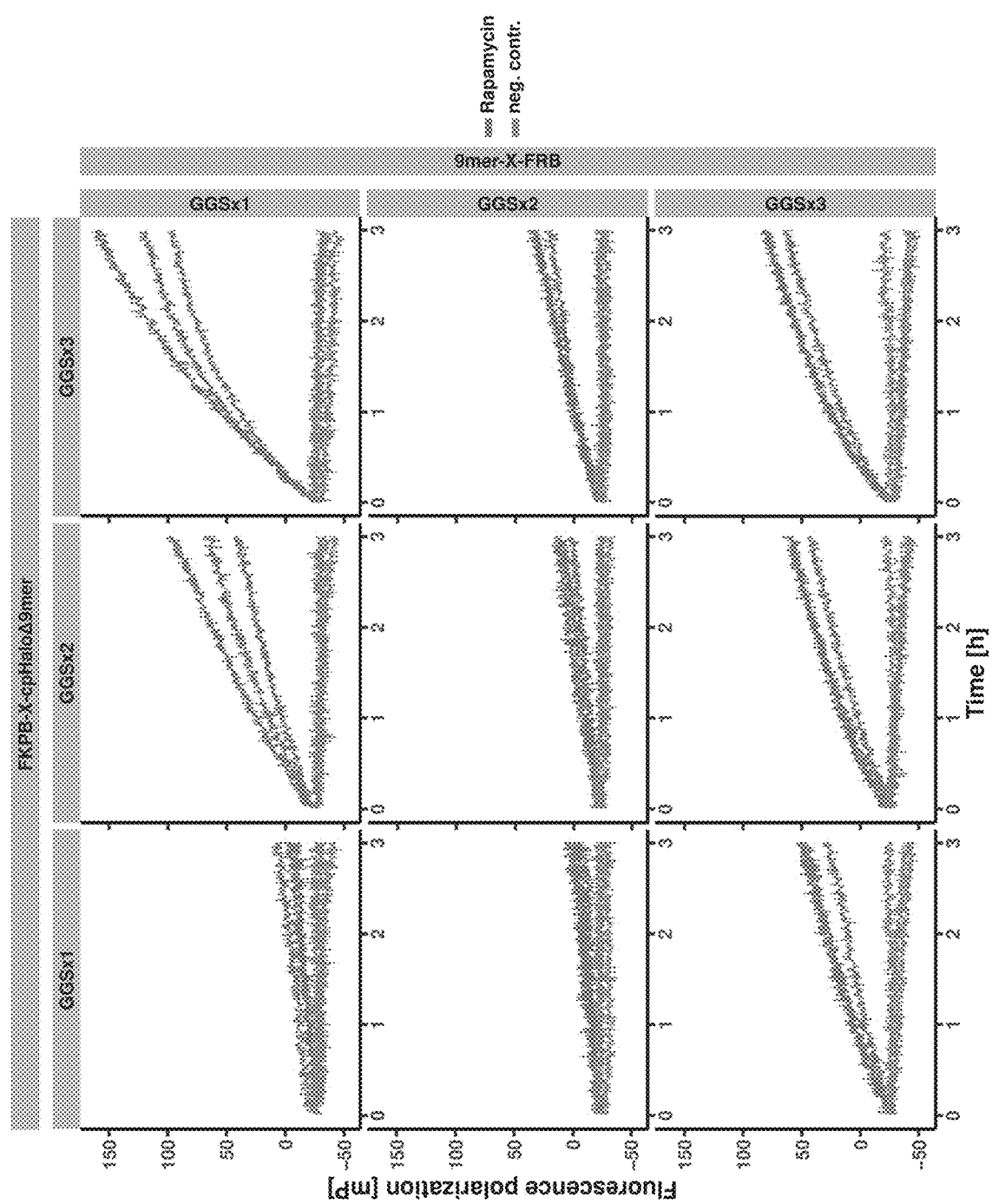
FIG. 14 Impact of different flexible linkers in the FKBP/FRB model system: Labelling kinetics of split HaloTag™ fused to FKBP and FRB using different flexible linkers were observed via a fluorescence polarization assay in the presence or absence of rapamycin. Halo-TMR was used as substrate and each experiment was performed in triplicate.
Figure 15:
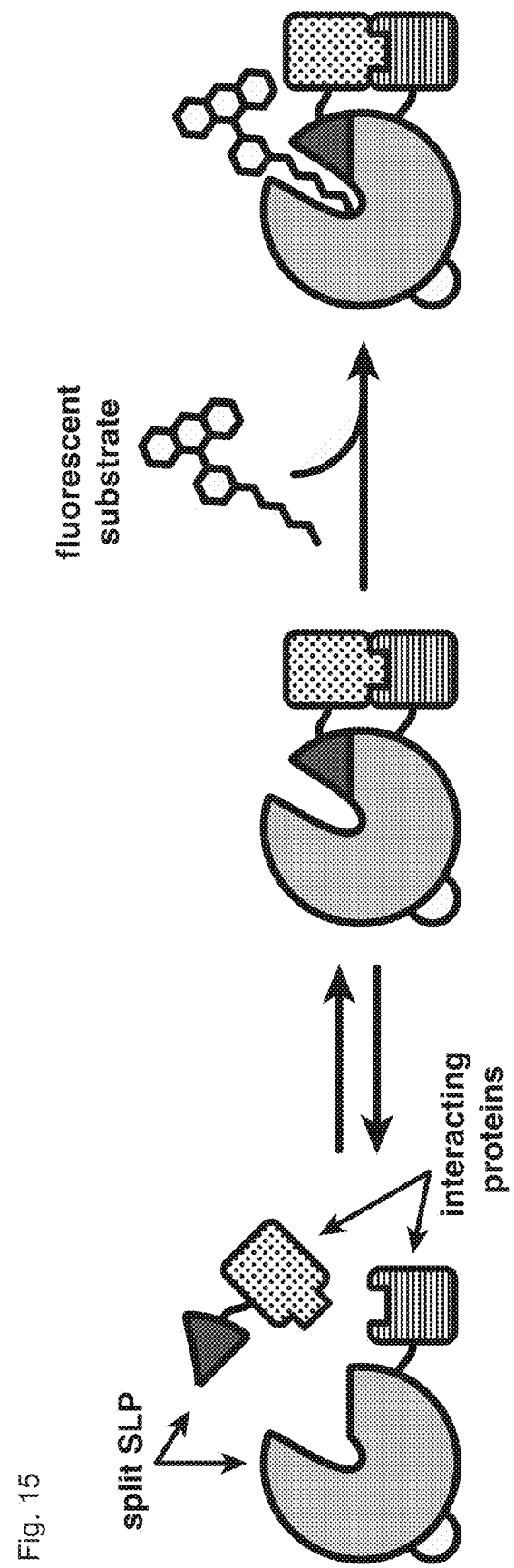
FIG. 15 shows a schematic representation of the split system (sensor module being split into two peptide chains, each connected to one part of the effector system).

The inventors further tested the performance of the split-HaloTag system of the invention for labelling protein-protein interactions in a simple model system. They used the strong interaction of the proteins FKBP and FRB, which is conditional on the presence of the small-molecule drug rapamycin. After fusing the split HaloTag™ fragments to FKBP and FRB labelling was observed only in the presence of rapamycin, showing that our strategy works in a model system (FIG. 13). Different flexible linkers (1-3 times GGS) were placed between the interacting proteins (FKBP/FRP) and the split HaloTag™ fragments to assess the effect of linker length and to find well performing linker combinations (FIG. 14). All linker combinations gave at least a minimal signal over noise, but certain combinations (FKBP-GGSx3-cpHaloΔ and 9mer-GGSx1-FRB) clearly showed a superior performance. These assays exemplify that the sensor can integrate protein-protein interactions and could potentially be used to record activity of signaling pathways in vitro or in vivo.

TABLE 1

Affinities of fluorescent ligands to the catalytically dead mutants HaloTag7$_{D106A}$ and cpHaloΔ9mer$_{D106A}$ K$_d$ values are given with the standard error resulting from the non-linear regression.

| Protein | Fluorescent ligand | K$_d$ [µM] |
|---|---|---|
| HaloTag7$_{D106A}$ | Halo-carbopyronine | 0.622 +/− 0.0037 |
| | Halo-tetramethylrhodamine | 6.68 +/− 0.16 |
| | Halo-tetramethylrhodamine-azetidine | 4.40 +/− 0.022 |
| | Halo-Oregon Green | 39.6 +/− 2.15 |
| | Halo-Alexa Fluor 488 | 94.0 +/− 2.01 |
| | Halo-silicon-rhodamine | 22.7 +/− 1.4 |

TABLE 1-continued

Affinities of fluorescent ligands to the catalytically dead mutants HaloTag7$_{D106A}$ and cpHaloΔ9mer$_{D106A}$ K$_d$ values are given with the standard error resulting from the non-linear regression.

| Protein | Fluorescent ligand | K$_d$ [µM] |
| --- | --- | --- |
| cpHaloΔ9mer$_{D106A}$ | Halo-silicon-rhodamine-azetidine (JF646) | 54.6 +/- 0.5 |
| | Halo-silicon-rhodamine-3-fluoroazetidin (JF635) | 172.2 +/- 8.2 |
| | Halo-carbopyronine | 90.5 +/- 1.8 |
| | Halo-tetramethylrhodamine | 115 +/- 1.8 |
| | Halo-tetramethylrhodamine-azetidine | 227 +/- 6.7 |

Example 11: Scanning the Mutation Tolerance on the Complementing Peptide

Experimental Procedure

Figure 16:
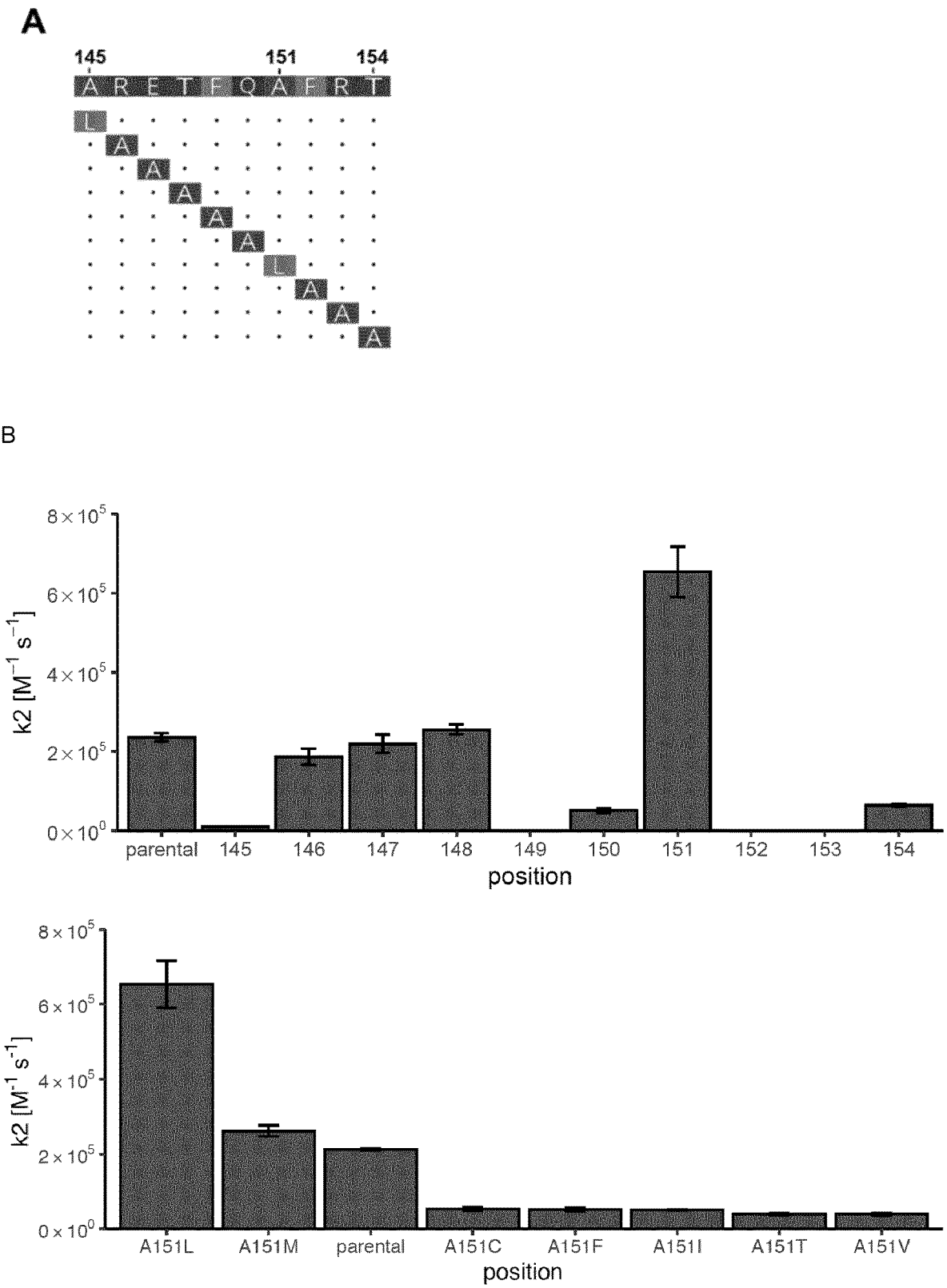
FIG. 16 Labeling kinetic study of an ALA-scan over the 10mer complementing peptide of cpHaloΔ. ARETFQAFRT: SEQ ID NO 029.

Kinetic by fluorescence polarization performed in buffer 50 mM NaCl, 50 mM HEPES, 100 UM EGTA, 0.5 g/l BSA, pH 7.3. Mix of 100 µl of 400 nM protein with 100 nM Halo-TMR in buffer in a black flat bottom 96 well plate equilibrated at 37° C. Reaction triggered by injecting 100 µl 10 mM CaCl$_2$ in buffer. Final concentrations: 200 nM Protein, 50 nM Halo-TMR, 5 mM CaCl$_2$). Additional background wells without protein added. Fluorescence polarization readout until plateau reached. Background values subtracted from measurements. Second order reaction rate fitted to obtain a k$_2^{app}$ Results Mutations on the 10mer peptide able to complement the activity of cpHaloΔ have a direct massive influence on the sequence conservation (%) as compared to the native sequence. The inventors therefore performed an alanine scanning over the peptide in the context of an already optimized CaProLa construction in order to evaluate the influence of peptide mutations on the overall labeling kinetics at calcium saturation (FIG. 16). This alanine scanning means that each residue was one by one mutated into alanine despite when an alanine was present, it was replaced by a leucine which the inventors consider to be the most "property conservative" in an α-helix context.

Side by side, labeling kinetics comparisons suggest that:
Ala145 mutation into Leucine affects the integrator kinetics. That can be explained by the tight hydrophobic packing in the area, the cumbersomeness of a leucine might rupture this packing, reduce the ability of the peptide to fold in an α-helix and/or interact with the substrate.
1 Arg146, Glu147 and Thr148 mutations into alanine were not detrimental for the integrator functioning. The inventors hypothesize that the ability to form an α-helix is only essential at this positions.
Phe149 and Gln150 mutations reduce drastically the integrator kinetics, especially in the case of the phenylalanine which participates in the hydrophobic heart of the substrate accommodation site. The Gln is more surface exposed but seems to cap the region and helps in the proper folding of the peptide.
A151 mutation into leucine unexpectedly led to an increase of labeling speed as compared to the parental protein (~ 3 fold). The inventors therefore further investigated mutations at this position and evaluated that while methionine mutation performed equivalently to the parental protein, all other tested modifications (Cys/Phe/11e/Thr/Val) were deleterious for the activity.
Phe152 and Arg153 mutation lead to a loss of protein ability to label. While Phe152 is part of the hydrophobic heart of the protein active site, the Arg153 interacts with multiple surrounding residues. They are most probably both crucial for the peptide proper α-helix folding.
Thr154 mutation also leads to a decrease in protein labeling velocity, this residue seems to lock the peptide in the proper orientation by interacting with a residue of the adjacent α-helix.

To summarize, Ala145, Phe149, Gln150, Phe152 and Arg153 seem not prone to modification in the CaProLa sensor context. On the other hand, Arg146, Glu147 and Thr148 modifications are less of an issue. Finally, A151 modification can even lead to an activity increase but it is highly dependent on the nature of the modification.

Example 12: Development of a Glutamate Integrator Based on cpHaloΔ/H-Peptide Experimental Procedure Fluorescent polarization kinetic experiments were performed in black flat bottom 96 well plates at 37 or 22° C. Buffer composition was 50 mM NaCl, 50 mM HEPES, 0.5 g/L BSA, pH 7.3. 150 µL of 400 nM protein and glutamate at 2× final concentration were equilibrated for half an hour, and reaction initiated by injection of 100 µL Halo-CPY in buffer. Final concentration of reagents was 200 nM protein and 50 nM Halo-CPY. Fluorescence polarization was read out until measurements reached a plateau. Curves were fit to a mono-exponential in Prism 8 (GraphPad). Saturation of glutamate is observed at 1 mM.

Results

Figure 17:
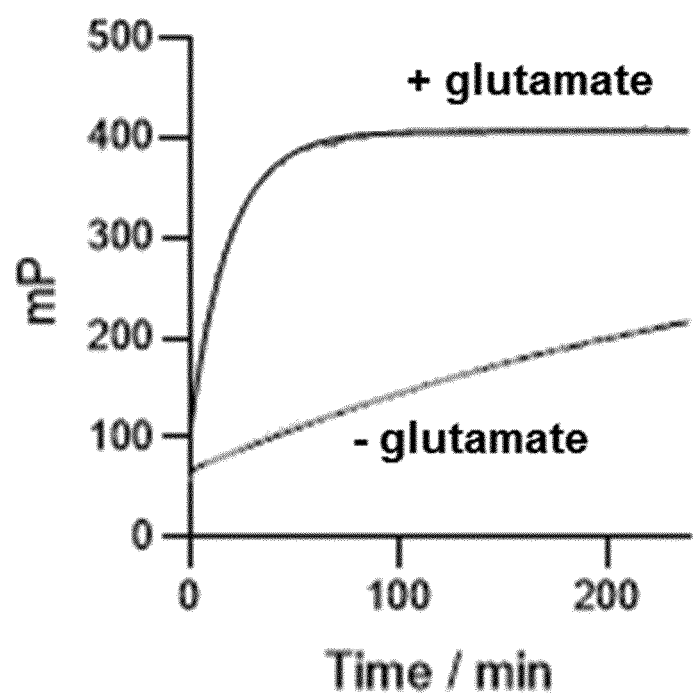
FIG. 17 Kinetic of labeling of dGluProLa followed by fluorescence polarization. Technical triplicate±S.E.M.

The inventors have successfully generated an integrator for glutamate (GluProLa: Glutamate dependent Protein Labeling), the primary excitatory neurotransmitter in the mammalian Central Nervous System (CNS). GluProLa is designed around the architecture of an existing real-time, intensiometric sensor of glutamate, iGluSnFR. iGluSnFR is derived from the bacterial periplasmic glutamate binding protein Gltl. Insertion of circularly permuted green fluorescent protein (cpGFP) into a flexible hinge in Gltl resulted in a green-fluorescent sensor which responds to changes in glutamate concentration with an increase in fluorescence intensity. As the N- and C-termini of Gltl are on the same face of Gltl, and mechanistic studies of iGluSnFR suggest that these positions should show glutamate-binding dependent changes in their relative distance and/or orientation, the inventors reasoned that these might be suitable sites for fusion to H-peptide and cpHaloΔ. The inventors therefore created GluProLa constructs linking H-peptide (SEQ ID NO 007 (PEP2)) to the N-terminus of iGluSnFR and cpHaloΔ (SEQ ID NO:004) to the C-terminus. The inventors cloned and purified a small family of constructs with flexible GGTGGS (SEQ ID NO 026) and/or Pro10 linkers between H-peptide and iGluSnFR and between iGluSnFR and cpHaloΔ. All constructs showed labeling in the presence of glutamate and a fluorescent HaloTag™ substrate, as determined by in vitro fluorescence polarization assays (e.g. FIG. 17). The inventors found that relative labelling kinetics in the presence or absence of glutamate could be tuned by varying the linker composition. A construct bearing a GGTGGS (SEQ ID NO 026) sequence at both the H-peptide/iGluSnFR and iGluSnFR/cpHaloΔ positions showed the lowest rate of non-specific labeling. The inventors introduced a point mutation (G67A) in cpGFP. This mutation prevents chromophore formation in wtGFP, gGluProLa (g standing for green) variants with the G67A mutation (dubbed as dGluProLas, for dark) were also found to be non-fluorescent. GluProLa variants showed glutamate concentration dependent labelling. While dGluProLa variants showed slower labelling kinetics than their parent gGlu-ProLa sequences, they maintained the same affinity for glutamate. The best construction highlights a 15-fold difference in term of labeling kinetic (i.e. activity) (FIG. 17).

TABLE 2

Summary of second generation CaProLa constructs, used CaM-M13 variants, $EC_{50}$ values reported for CaMPARI2 and $EC_{50}$ measured for CaProLa.

| CaProLa version | CaM-M13 origin | Reported $EC_{50}$ | Measured |
|---|---|---|---|
| CaProLa 1.4 (1. gen.) | CaMPARI | 111 | 146 ± 44.6 |
| CaProLa 2.1 | CaMPARI2 | 825 nM | 625 ± 25 nM |

TABLE 2-continued

Summary of second generation CaProLa constructs, used CaM-M13 variants, $EC_{50}$ values reported for CaMPARI2 and $EC_{50}$ measured for CaProLa.

| CaProLa version | CaM-M13 origin | Reported $EC_{50}$ | Measured |
|---|---|---|---|
| CaProLa 2.2 | CaMPARI2 | 360 nM | 448 ± 7 nM |
| CaProLa 2.3 | CaMPARI2 | 110 nM | 82.6 ± 4.5 nM |

Sequences

HaloTag™ 7 (see GenBank AQS79242); the cp version employed in creating the invention does not contain the C-terminal 27 amino acids of this sequence SEQ ID NO 001: HaloTag7 circular permutated sequence

```
SEQ ID NO 001: HaloTag7 circular permutated sequence
FARETFQAFRTTDVGRKLIIDQNVFIEGTLPMGVVRPLTEVEMDHYREPFLNPVDREPLWRF

PNELPIAGEPANIVALVEEYMDWLHQSPVPKLLFWGTPGVLIPPAEAARLAKSLPNCKAVDIG

PGLNLLQEDNPDLIGSEIARWLSTLEIGGTGGSGGTGGSGGSIGTGFPFDPHYVEVLGERM

HYVDVGPRDGTPVLFLHGNPTSSYVWRNIIPHVAPTHRCIAPDLIGMGKSDKPDLGYFFDDH

VRFMDAFIEALGLEEVVLVIHDWGSALGFHWAKRNPERVKGIAFMEFIRPIPTWDEW

SEQ ID NO 002: cpHaloΔ N-terminal sequence
DVGRKLIIDQNVFIEGTLPMGVVRPLTEVEMDHYREPFLNPVDREPLWRFPNELPIAGEPANI

VALVEEYMDWLHQSPVPKLLFWGTPGVLIPPAEAARLAKSLPNCKAVDIGPGLNLLQEDNP

DLIGSEIARWLSTLEI

SEQ ID NO 003: cpHaloΔ C-terminal sequence
IGTGFPFDPHYVEVLGERMHYVDVGPRDGTPVLFLHGNPTSSYVWRNIIPHVAPTHRCIAPD

LIGMGKSDKPDLGYFFDDHVRFMDAFIEALGLEEVVLVIHDWGSALGFHWAKRNPERVKGI

AFMEFIRPIPTWDEW

SEQ ID 004 cpHaloΔ full sequence
DVGRKLIIDQNVFIEGTLPMGVVRPLTEVEMDHYREPFLNPVDREPLWRFPNELPIAGEPANI

VALVEEYMDWLHQSPVPKLLFWGTPGVLIPPAEAARLAKSLPNCKAVDIGPGLNLLQEDNP

DLIGSEIARWLSTLEIGGTGGSGGTGGSGGSIGTGFPFDPHYVEVLGERMHYVDVGPRDGT

PVLFLHGNPTSSYVWRNIIPHVAPTHRCIAPDLIGMGKSDKPDLGYFFDDHVRFMDAFIEALG

LEEVVLVIHDWGSALGFHWAKRNPERVKGIAFMEFIRPIPTWDEW

SEQ ID 005 cpHaloΔ internal linker sequence:
GGTGGSGGTGGSGGS

SEQ ID NO 006 (PEP1): 9mer Peptide
145-ARETFQAFR-153

SEQ ID NO 007 (PEP2): 10mer Peptide (higher propensity to
complement the activity = faster kinetics)
145-ARETFQAFRT-154

SEQ ID NO 008 (M13)
RVDSSRRKFNKTGKALRAIGRLSSLE

SEQ ID NO 009 (CaM)
DQLTEEQIAEFKEAFSLFDKDGDGTITTKELGTVMRSLGQNPTEAELQDMINEVDADGDGTI

DFPEFLTMMARKMKDTDSEEEIREAFRVFDKDGNGYISAAELRHVMTNLGEKLTDEEVDEM

IREADIDGDGQVNYEEFVVMMTAK

SEQ ID NO 010 (SPLT1)
RVDSSRRKFNKTGKALRAIGRLSSLEGGSDVGRKLIIDQNVFIEGTLPMGVVRPLTEVEMDH

YREPFLNPVDREPLWRFPNELPIAGEPANIVALVEEYMDWLHQSPVPKLLFWGTPGVLIPPA

EAARLAKSLPNCKAVDIGPGLNLLQEDNPDLIGSEIARWLSTLEIGGTGGSGGTGGSGGSIG
```

-continued

TGFPFDPHYVEVLGERMHYVDVGPRDGTPVLFLHGNPTSSYVWRNIIPHVAPTHRCIAPDLI

GMGKSDKPDLGYFFDDHVRFMDAFIEALGLEEVVLVIHDWGSALGFHWAKRNPERVKGIAF

MEFIRPIPTWDEW

SEQ ID NO 011 (SPLT2)
ARETFQAFRGGSDQLTEEQIAEFKEAFSLFDKDGDGTITTKELGTVMRSLGQNPTEAELQD

MINEVDADGDGTIDFPEFLTMMARKMKDTDSEEEIREAFRVFDKDGNGYISAAELRHVMTNL

GEKLTDEEVDEMIREADIDGDGQVNYEEFVVMMTAK

SEQ ID NO 012 (SPLT3)
ARETFQAFRTGSDQLTEEQIAEFKEAFSLFDKDGDGTITTKELGTVMRSLGQNPTEAELQD

MINEVDADGDGTIDFPEFLTMMARKMKDTDSEEEIREAFRVFDKDGNGYISAAELRHVMTNL

GEKLTDEEVDEMIREADIDGDGQVNYEEFVVMMTAK

SEQ ID NO 013 (CONF1)
ARETFQAFRGGSDQLTEEQIAEFKEAFSLFDKDGDGTITTKELGTVMRSLGQNPTEAELQD

MINEVDADGDGTIDFPEFLTMMARKMKDTDSEEEIREAFRVFDKDGNGYISAAELRHVMTNL

GEKLTDEEVDEMIREADIDGDGQVNYEEFVVMMTAKEFPPPPPPPPPPPPPPPPPPPPPP

PPPPPPPGGSRVDSSRRKFNKTGKALRAIGRLSSLEGGSDVGRKLIIDQNVFIEGTLPMGVV

RPLTEVEMDHYREPFLNPVDREPLWRFPNELPIAGEPANIVALVEEYMDWLHQSPVPKLLF

WGTPGVLIPPAEAARLAKSLPNCKAVDIGPGLNLLQEDNPDLIGSEIARWLSTLEIGGTGGSG

GTGGSGGSIGTGFPFDPHYVEVLGERMHYVDVGPRDGTPVLFLHGNPTSSYVWRNIIPHVA

PTHRCIAPDLIGMGKSDKPDLGYFFDDHVRFMDAFIEALGLEEVVLVIHDWGSALGFHWAKR

NPERVKGIAFMEFIRPIPTWDEW

SEQ ID NO 014 (CONF2)
ARETFQAFFITGSDQLTEEQ1AEFKEAFSLFDKDGDGTITTKELGTVMRSLGQNPTEAELQD

MINEVDADGDGTIDFPEFLTMMARKMKDTDSEEEIREAFRVFDKDGNGYISAAELRHVMTNL

GEKLTDEEVDEMIREADIDGDGQVNYEEFVVMMTAKEFPPPPPPPPPPPPPPPPPPPPPP

PPPPPPPGGSRVDSSRRKFNKTGKALRAIGRLSSLEGGSDVGRKLIIDQNVFIEGTLPMGVV

RPLTEVEMDHYREPFLNPVDREPLWRFPNELPIAGEPANIVALVEEYMDWLHQSPVPKLLF

WGTPGVLIPPAEAARLAKSLPNCKAVDIGPGLNLLQEDNPDLIGSEIARWLSTLEIGGTGGSG

GTGGSGGSIGTGFPFDPHYVEVLGERMHYVDVGPRDGTPVLFLHGNPTSSYVWRNIIPHVA

PTHRCIAPDLIGMGKSDKPDLGYFFDDHVRFMDAFIEALGLEEVVLVIHDWGSALGFHWAKR

NPERVKGIAFMEFIRPIPTWDEW

SEQ ID NO 015 (FKBP)
MGVQVETISPGDGRTFPKRGQTCVVHYTGMLEDGKKFDSSRDRNKPFKFMLGKQEVIRGW

EEGVAQMSVGQRAKLTISPDYAYGAIGHPGIIPPHATLVFDVELLKLE

SEQ ID NO 016 (FRB)
AILWHEMWHEGLEEASRLYFGERNVKGMFEVLEPLHAMMERGPQTLKETSFNQAYGRDL

MEAQEWCRKYMKSGNVKDLLQAWDLYYHVFRRISK

SEQ ID NO 017 (RAPIND1)
MGVQVETISPGDGRTFPKRGQTCVVHYTGMLEDGKKFDSSRDRNKPFKFMLGKQEVIRGW

EEGVAQMSVGQRAKLTISPDYAYGAIGHPGIIPPHATLVFDVELLKLEGSGGTGGSGDVGR

KLIIDQNVFIEGTLPMGVVRPLTEVEMDHYREPFLNPVDREPLWRFPNELPIAGEPANIVALV

EEYMDWLHQSPVPKLLFWGTPGVLIPPAEAARLAKSLPNCKAVDIGPGLNLLQEDNPDLIGS

EIARWLSTLEIGGTGGSGGTGGSGGSIGTGFPFDPHYVEVLGERMHYVDVGPRDGTPVLFL

```
HGNPTSSYVWRNIIPHVAPTHRCIAPDLIGMGKSDKPDLGYFFDDHVRFMDAFIEALGLEEV

VLVIHDWGSALGFHWAKRNPERVKGIAFMEFIRPIPTWDEW

SEQ ID NO 018 (RAPIND2)
ARETFQAFRGGSAILWHEMWHEGLEEASRLYFGERNVKGMFEVLEPLHAMMERGPQTLK

ETSFNQAYGRDLMEAQEWCRKYMKSGNVKDLLQAWDLYYHVFRRISK

SEQ ID NO 019 (RAPIND3)
ARETFQAFRTGSAILWHEMWHEGLEEASRLYFGERNVKGMFEVLEPLHAMMERGPQTLKE

TSFNQAYGRDLMEAQEWCRKYMKSGNVKDLLQAWDLYYHVFRRISK

SEQ ID NO 020 (GLT1)
AAGSTLDKIAKNGVIVVGHRESSVPFSYYDNQQKVVGYSQDYSNAIVEAVKKKLNKPDLQV

KLIPITSQNRIPLLQNGTFDFECGSTTNNVERQKQAAFSDTIFVVGTRLLTKKGGDIKDFANLK

DKAVVVTSGTTSEVLLNKLNEEQKMNMRIISAKDHGDSFRTLESGRAVAFMMDDVLLAGER

AKAKKPDNWEIVGKPQSQEAYGCMLRKDDPQFKKLMDDTIAQVQTSGEAEKWFDKWFKNP

ILV

SEQ ID NO 021 (GLT2)
NPLNMNFELSDEMKALFKEPNDKALK

SEQ ID NO 022 (GLT3)
AAGSTLDKIAKNGVIVVGHRESSVPFSYYDNQQKVVGYSQDYSNAIVEAVKKKLNKPDLQV

KLIPITSQNRIPLLQNGTFDFECGSTTNNVERQKQAAFSDTIFVVGTRLLTKKGGDIKDFANLK

DKAVVVTSGTTSEVLLNKLNEEQKMNMRIISAKDHGDSFRTLESGRAVAFMMDDVLLAGER

AKAKKPDNWEIVGKPQSQEAYGCMLRKDDPQFKKLMDDTIAQVQTSGEAEKWFDKWFKNP

ILVSHNVYIMADKQRNGIKANFKIRHNIEDGGVQLAYHYQQNTPIGDGPVLLPDNHYLSTQSK

LSKDPNEKRDHMVLLEFVTAAGITLGMDELYKGGTGGSMVSKGEELFTGVVPILVELDGDV

NGHKFSVSGEGEGDATYGKLTLKFICTTGKLPVPWPTLVTTLTYGVQCFSRYPDHMKQHDFF

KSAMPEGYIQERTIFFKDDGNYKTRAEVKFEGDTLVNRIELKGIDFKEDGNILGHKLEYNFNN

PLNMNFELSDEMKALFKEPNDKALK

SEQ ID NO 023 (GLTIND1)
ARETFQAFRTGGTGGSAAGSTLDKIAKNGVIVVGHRESSVPFSYYDNQQKVVGYSQDYSNAI

VEAVKKKLNKPDLQVKLIPITSQNRIPLLQNGTFDFECGSTTNNVERQKQAAFSDTIFVVGTRL

LTKKGGDIKDFANLKDKAVVVTSGTTSEVLLNKLNEEQKMNMRIISAKDHGDSFRTLESGRA

VAFMMDDVLLAGERAKAKKPDNWEIVGKPQSQEAYGCMLRKDDPQFKKLMDDTIAQVQTS

GEAEKWFDKWFKNPILV

SEQ ID NO 024 (GLTIND2)
NPLNMNFELSDEMKALFKEPNDKALKGGTGGSDVGRKLIIDQNVFIEGTLPMGVVRPLTEVE

MDHYREPFLNPVDREPLWRFPNELPIAGEPANIVALVEEYMDWLHQSPVPKLLFWGTPGVLIP

PAEAARLAKSLPNCKAVDIGPGLNLLQEDNPDLIGSEIARWLSTLEIGGTGGSGGTGGSGGSIG

TGFPFDPHYVEVLGERMHYVDVGPRDGTPVLFLHGNPTSSYVWRNIIPHVAPTHRCIAPDLIG

MGKSDKPDLGYFFDDHVRFMDAFIEALGLEEVVLVIHDWGSALGFHWAKRNPERVKGIAFM

EFIRPIPTWDEW

SEQ ID NO 025 (GLTIND3)
ARETFQAFRTGGTGGSAAGSTLDKIAKNGVIVVGHRESSVPFSYYDNQQKVVGYSQDYSNAI

VEAVKKKLNKPDLQVKLIPITSQNRIPLLQNGTFDFECGSTTNNVERQKQAAFSDTIFVVGTRL

LTKKGGDIKDFANLKDKAVVVTSGTTSEVLLNKLNEEQKMNMRIISAKDHGDSFRTLESGRA

VAFMMDDVLLAGERAKAKKPDNWEIVGKPQSQEAYGCMLRKDDPQFKKLMDDTIAQVQTS

GEAEKWFDKWFKNPILVSHNVYIMADKQRNGIKANFKIRHNIEDGGVQLAYHYQQNTPIGD
```

-continued

GPVLLPDNHYLSTQSKLSKDPNEKRDHMVLLEFVTAAGITLGMDELYKGGTGGSMVSKGEE

LFTGVVPILVELDGDVNGHKFSVSGEGEGDATYGKLTLKFICTTGKLPVPWPTLVTTLTYGVQ

CFSRYPDHMKQHDFFKSAMPEGYIQERTIFFKDDGNYKTRAEVKFEGDTLVNRIELKGIDFKE

DGNILGHKLEYNFNNPLNMNFELSDEMKALFKEPNDKALKGGTGGSDVGRKLIIDQNVFIEG

TLPMGVVRPLTEVEMDHYREPFLNPVDREPLWRFPNELPIAGEPANIVALVEEYMDWLHQSP

VPKLLFWGTPGVLIPPAEAARLAKSLPNCKAVDIGPGLNLLQEDNPDLIGSEIARWLSTLEIGG

TGGSGGTGGSGGSIGTGFPFDPHYVEVLGERMHYVDVGPRDGTPVLFLHGNPTSSYVWRNIIP

HVAPTHRCIAPDLIGMGKSDKPDLGYFFDDHVRFMDAFIEALGLEEVVLVIHDWGSALGFHW

AKRNPERVKGIAFMEFIRPIPTWDEW

---

The invention claimed is:

1. A modular polypeptide comprising or consisting essentially of a first partial effector sequence comprising or consisting essentially of
an N-terminal first effector sequence part comprising SEQ ID NO: 002 or by a sequence at least (≥) 90% identical to SEQ ID NO: 002,
a C-terminal first effector sequence part comprising SEQ ID NO: 003 or by a sequence at least (≥) 90% identical to SEQ ID NO: 003,
an internal linker consisting of 10 to 35 amino acids, wherein the internal linker connects the C-terminus of the N-terminal first effector sequence part to the N-terminus of the C-terminal first effector sequence part; connected to
a sensor module sequence, which is connected to
a second partial effector sequence comprising or consisting essentially of a sequence selected from SEQ ID NO: 006 (PEP1), SEQ ID NO: 007 (PEP2), and a sequence at least (≥) 75% identical to SEQ ID NO: 007 (PEP2),
wherein said sequence at least (2) 75% identical to SEQ ID NO: 007 (PEP2) has at least one mutation at position A151, R146, E147, T148, or T154 with respect to SEQ ID NO: 007 (PEP2),
wherein
the first and second partial effector sequences together constitute a circularly permuted haloalkane dehalogenase, and are capable, when brought into close proximity of each other, to effect covalent attachment of a halogen alkane moiety, and wherein
the sensor module sequence is selected from
a) a single sensor polypeptide capable of undergoing conformational change from a first confirmation to a second confirmation depending on the presence or concentration of an analyte compound, wherein in the first conformation, the first and second partial effector sequences are in close proximity, and in the second conformation, the first and second partial effector sequences are not in close proximity, wherein the first partial effector sequence is attached to the C-terminus of the sensor module sequence and the second partial effector sequence is attached to the N-terminus of the sensor module sequence,
and
b) a sensor polypeptide pair comprising a first sensor polypeptide and a second sensor polypeptide, wherein the first sensor polypeptide is covalently attached through a peptide bond to the first partial effector sequence and the second sensor polypeptide is covalently attached to the second partial effector sequence, the first sensor polypeptide and the second sensor polypeptide are capable of specific molecular interaction, and the first and second sensor polypeptides are part of separate polypeptide chains.

2. The modular polypeptide of claim 1, wherein the first partial effector sequence and the second partial effector sequence, when brought into close proximity of each other, comprise an activity of $10^2 s^{-1} M^{-1}$ in a fluorescence polarization assay using N-(10-(2-carboxy-5-((2-(2-((6-chlorohexyl)oxy) ethoxy)ethyl) carbamoyl)phenyl)-7-(dimethylamino)-9,9-dimethylanthracen-2 (9H)-ylidene)-N-methylmethanaminium as the substrate.

3. The modular polypeptide of claim 1, wherein the first partial effector sequence and the second partial effector sequence, when brought into close proximity of each other, have at least 0.5% of the activity of SEQ ID NO: 001.

4. The modular polypeptide according to claim 1, wherein the internal linker comprises or consists of the amino acids G, A, J, S, T, P, C, V, M.

5. The modular polypeptide according claim 1, wherein the first partial effector sequence comprises or consists essentially of
a) SEQ ID NO: 004, or
b) a sequence at least (≥) 90% identical to SEQ ID NO: 4, or
c) a sequence at least (≥) 90% identical to construct consisting of SEQ ID NO: 002 joined by a linker to SEQ ID NO: 003,
wherein the first and second partial effector sequences together comprise at least 0.5% of the activity of SEQ ID NO: 004 together with SEQ ID NO: 007 (PEP2).

6. The modular polypeptide according to claim 1, wherein the first partial effector sequence is connected to the sensor module sequence by a first intermodular linker sequence, and/or the second partial effector sequence is connected to the sensor module sequence by a second intermodular linker sequence.

7. The modular polypeptide according to claim 1, wherein the sensor module sequence is a single sensor polypeptide that consists of an N-terminal first partial sensor sequence and a C-terminal second partial sensor sequence connected by a sensor linker sequence.

8. The modular polypeptide according to claim 7, wherein the first partial sensor sequence is a calmodulin polypeptide and the second partial sensor sequence is a calmodulin-binding peptide, wherein the calmodulin polypeptide is or comprises SEQ ID NO: 009 (CaM), or a sequence at least 90% identical to SEQ ID NO: 009 (CaM) and having the same biological activity, and the calmodulin-binding peptide is or comprises SEQ ID NO: 008 (M13).

9. The modular polypeptide according to claim 8, wherein the modular polypeptide comprises a first polypeptide sequence consisting or comprising SEQ ID NO: 010 (SPLT1) or a sequence at least 90% identical to SEQ ID NO: 010 (SPLT1), and a second polypeptide sequence SEQ ID NO: 011 (SPLT2) or a sequence at least 90% identical to SEQ ID NO: 011 (SPLT2), wherein the first and the second polypeptide sequence have at least 0.5%, of the activity of the combination of SEQ ID NO: 010 (SPLT1) and SEQ ID NO: 011 (SPLT2).

10. The modular polypeptide according to claim 8, wherein the sensor module sequence is constituted by a single sensor polypeptide, comprising, from N to C-terminus,
  a) a calmodulin polypeptide wherein the calmodulin polypeptide is SEQ ID NO: 009 (CaM), or a sequence at least 90% identical to SEQ ID NO: 009 (CaM) and having the same biological activity;
  b) a peptide linker, wherein the peptide linker is a polyproline-type rigid helix or a $P_n$ proline polypeptide wherein n is selected rom an integer from 15 to 35, optionally flanked by 1-4 amino acids; and
  c) a calmodulin binding peptide wherein the calmodulin binding peptide is a sequence comprising or consisting of SEQ ID NO: 008 (M13).

11. The modular polypeptide according to claim 1, wherein the sensor module sequence comprises or consisting essentially of
  a) an N-terminal part of a glutamate binding protein, wherein the first sensor polypeptide is or comprises SEQ ID NO: 020 (GLT1), or a sequence at least 90% identical to SEQ ID NO: 020 (GLT1), and
  a C-terminal part of a glutamate binding protein, wherein the second sensor polypeptide is or comprises SEQ ID NO: 021 (GLT2), or a sequence at least 90% identical to SEQ ID NO: 021 (GLT2) and having substantially the same biological activity;
  wherein the combination of the first sensor polypeptide and the second sensor polypeptide and have substantially the same biological activity as a combination of SEQ ID NO: 020 (GLT1) and SEQ ID NO: 021 (GLT2);
  or
  b) a sequence at least ($\geq$) 90% identical to a construct consisting of SEQ ID NO: 020 (GLT1) joined by a polypeptide linker to SEQ ID NO: 021 (GLT2).

12. The modular polypeptide according to claim 1, wherein the sensor module sequence is constituted by a sensor polypeptide pair comprising:
  a) a first sensor polypeptide that is or comprises an FKBP12 polypeptide, wherein the FKBP12 polypeptide is or comprises SEQ ID NO: 015 (FKBP), or a sequence at least 90% identical to SEQ ID NO: 015 (FKBP) and having substantially the same biological activity,
  b) and a second sensor polypeptide that is or comprises a FRB peptide, wherein the FRB peptide is or comprises SEQ ID NO: 016 (FRB), or a sequence at least 90% identical to SEQ ID NO: 016 (FRB) and having substantially the same biological activity,
  wherein the first sensor polypeptide is covalently attached through a peptide bond to the first partial effector sequence and the second sensor polypeptide is covalently attached to the second partial effector sequence, and the first and second sensor polypeptides are part of separate polypeptide chains,
  wherein the first partial effector sequence is connected to the C-terminus of the first sensor polypeptide by a first intermodular linker sequence having 2 to 9 amino acids, and/or the second partial effector sequence is connected to the N-terminus of the second sensor polypeptide by a second intermodular linker having 2 to 9 amino acids.

13. The modular polypeptide according to claim 12, wherein the modular polypeptide comprises a first polypeptide sequence consisting or comprising SEQ ID NO: 017 (RAPIND1) or a sequence at least 90% identical to SEQ ID NO: 017 (RAPIND1) and a second polypeptide sequence selected from SEQ ID NO: 018 (RAPIND2) and SEQ ID NO: 019 (RAPIND3) or a sequence at least 90% identical to SEQ ID NO: 018 (RAPIND2), wherein the first and the second polypeptide sequence together have at least 50% of the activity of the combination of SEQ ID NO: 017 (RAPIND1) and SEQ ID NO: 018 (RAPIND2).

14. A nucleic acid sequence, or a plurality of nucleic acid sequences, encoding a modular polypeptide according to claim 1.

15. A combination of nucleic acid sequences comprising
  a) a first nucleic acid sequence encoding a first partial effector sequence, wherein the encoded first partial effector sequence comprises, from N to C-terminus,
    i) SEQ ID NO: 002, or a sequence at least ($\geq$) 90% identical to SEQ ID NO: 002,
    ii) a polypeptide linker sequence having 10-35 amino acids,
    iii) SEQ ID NO: 003 or a sequence at least ($\geq$) 90% identical to SEQ ID NO: 003;
  b) a second nucleic acid sequence encoding a second partial effector sequence comprising SEQ ID NO: 006 (PEP1) or 007 (PEP2), or encoding a sequence at least ($\geq$) 95% identical to SEQ ID NO: 006 (PEP1),
  wherein the first and second partial effector sequences together constitute a circularly permuted haloalkane dehalogenase, and are capable, when brought into close proximity of each other, to effect covalent attachment of a halogen alkane moiety.

16. A nucleic acid expression system comprising
  a) the nucleic acid sequence according to claim 14, or
  b) a first nucleic acid sequence encoding a first partial effector sequence, wherein the encoded first partial effector sequence comprises, from N to C-terminus,
    SEQ ID NO: 002, or a sequence at least ($\geq$) 90% identical to SEQ ID NO: 002,
    a polypeptide linker sequence having 10-35 amino acids, and
    SEQ ID NO: 003 or a sequence at least ($\geq$) 90% identical to SEQ ID NO: 003; and a second nucleic acid sequence encoding a second partial effector sequence comprising by SEQ ID NO: 006 (PEP1) or 007 (PEP2), or encoding a sequence at least (≥) 95% identical to SEQ ID NO: 006 (PEP1), wherein the first and second partial effector sequences together constitute a circularly permuted haloalkane dehalogenase, and are capable, when brought into close proximity of each other, to effect covalent attachment of a halogen alkane moiety, and wherein, each of nucleic acid sequences a) and b) are under control of a promoter sequence.

17. A cell comprising the nucleic acid expression system according to claim 16, wherein the promoter is operable in said cell.

18. A non-human transgenic animal or plant comprising the nucleic acid expression system according to claim 16.

19. A kit comprising a nucleic acid sequence according to claim 14 and a substrate.

20. The modular polypeptide according to claim 8, wherein the sensor module sequence is constituted by a sensor polypeptide pair comprising:
   a) a first sensor polypeptide that is or comprises a calmodulin binding peptide, wherein the calmodulin-binding peptide is or comprises SEQ ID NO: 008 (M13),
   b) and a second sensor polypeptide that is or comprises a calmodulin polypeptide, wherein the calmodulin polypeptide is or comprises SEQ ID NO: 009 (CaM), or a sequence at least 90% identical to SEQ ID NO: 009 (CaM) and having substantially the same biological activity,
   wherein the first sensor polypeptide is covalently attached through a peptide bond to the first partial effector sequence and the second sensor polypeptide is covalently attached to the second partial effector sequence, and the first and second sensor polypeptides are part of separate polypeptide chains,
   wherein the first partial effector sequence is connected to the C-terminus of the first sensor polypeptide by a first intermodular linker sequence having 2 to 6 amino acids, and/or the second partial effector sequence is connected to the N-terminus of the second sensor polypeptide by a second intermodular linker having 2 to 6 amino acids.

21. The modular polypeptide according to claim 10, wherein the modular polypeptide comprises or consists of a sequence selected from SEQ ID NO: 013 (CONF1) and SEQ ID NO: 014 (CONF2), or a sequence at least 90% identical to SEQ ID NO: 013 (CONF1) or SEQ ID NO: 014 (CONF2), and having at least 0.5% of the activity of SEQ ID NO: 013 (CONF1).

22. The modular polypeptide according to claim 11, wherein the sensor module sequence is or comprises SEQ ID NO: 022 (GLT3), or a sequence at least 90% identical to SEQ ID NO: 022 (GLT3) and having the same biological activity.

23. The modular polypeptide according to claim 11, wherein the modular polypeptide comprises a first polypeptide sequence consisting of or comprising SEQ ID NO: 023 (GLTIND1), or a sequence at least 90% identical to SEQ ID NO: 023 (GLTIND1), and a second polypeptide sequence SEQ ID NO: 024 (GLTIND2) or a sequence at least 90% identical to SEQ ID NO: 024 (GLTIND2).

\* \* \* \* \*